US012297165B2

(12) United States Patent
Alabi et al.

(10) Patent No.: US 12,297,165 B2
(45) Date of Patent: May 13, 2025

(54) OLIGOTHIOETHERAMIDES (OLIGOTEAS) AS ANTI-MICROBIAL AND ANTI-BACTERIAL AGENTS

(71) Applicant: Cornell University, Ithaca, NY (US)

(72) Inventors: Christopher Akinleye Alabi, Ithaca, NY (US); Ngoc Nhu Phan, Ithaca, NY (US)

(73) Assignee: Cornell University, Ithaca, NY (US)

( * ) Notice: Subject to any disclaimer, the term of this patent is extended or adjusted under 35 U.S.C. 154(b) by 485 days.

(21) Appl. No.: 16/639,896

(22) PCT Filed: Aug. 17, 2018

(86) PCT No.: PCT/US2018/046870
§ 371 (c)(1),
(2) Date: Feb. 18, 2020

(87) PCT Pub. No.: WO2019/036585
PCT Pub. Date: Feb. 21, 2019

(65) Prior Publication Data

US 2020/0361861 A1 Nov. 19, 2020

Related U.S. Application Data

(60) Provisional application No. 62/546,905, filed on Aug. 17, 2017.

(51) Int. Cl.

*C07C 279/12* (2006.01)
*A61P 31/04* (2006.01)
*C07C 303/00* (2006.01)
*C07C 323/60* (2006.01)

(52) U.S. Cl.
CPC ............ *C07C 279/12* (2013.01); *A61P 31/04* (2018.01)

(58) Field of Classification Search
CPC ... C07C 279/12; C07C 323/60; C07C 303/00; A61P 31/04
See application file for complete search history.

(56) References Cited

U.S. PATENT DOCUMENTS

2016/0075831 A1 3/2016 Alabi et al.

FOREIGN PATENT DOCUMENTS

WO 2006079568 A2 1/2006
WO 2012149352 A1 11/2012

OTHER PUBLICATIONS

Artim et al., 2018, caplus an 2018:932075.*
Artim et al. abstract, 2018, abstract of ACS Infect. Diseases, 4, 8, 1257-1263.*
Porel, et al., "Sequence-Defined Backbone Modifications Regulate Antibacterial Activity of OligoTEAs," ACS Chem. Biol. vol. 12, 2017, all enclosed pages cited.
Artim, et al., "Effect of Composition on Antibacterial Activity of Sequence-Defined Cationic Oligothioetheramides," ACS Infect., 10.1021/acsinfecdis.8b00079 (2018), all enclosed pages cited.
Brown, et al., " Synthesis and Solution-Phase Characterization of Sulfonated Oligothioetheramides," Macromolecules, 10.1021/acs.macromol.7b01915 (2017), all enclosed pages cited.
Higgins, et al., "C-Peptide inhibitors of Ebola virus glycoprotein-mediated cell entry: Effects of conjugation to cholesterol and side chain-side chain crosslinking," Bioorganic & Medicinal Chemistry Letters, http://dx.doi.org/10.1016/j.bmcl.2013.07.056 (2013), all enclosed pages cited.
Pacherille, "Synthesis and Analysis of Antibacterial Oligothioetheramides," 2017, all enclosed pages cited.
Phan, et al., "Intracellular Delivery via Non-Charged Sequence-Defined Cell-Penetrating Oligomers," Bioconjugate Chemistry, 10.1021/acs.bioconjchem.8b00336 (2018), all enclosed pages cited.
Porel, et al., "Sequence-Defined Polymers via Orthogonal Allyl Acrylamide Building Blocks," J. Am. Chem. Soc. 2014, 136, all enclosed pages cited.
Porel, et al., "Sequence-Defined Oligothioetheramides," Synlett 2015, 26, A-G, all enclosed pages cited.
Porel, et al., "Sequence-defined bioactive macrocycles via an acid-catalysed cascade reaction," Nature Chemistry, 10.1038/NCHEM.2508 (2016) all enclosed pages cited.
Sorkin, et al., "Versatile Platform for the Synthesis of Orthogonally Cleavable Heteromultifunctional Cross-Linkers," Bioconjugate Chem., 10.1021/acs.bioconjchem.7b00033, (2017), all enclosed pages cited.

* cited by examiner

*Primary Examiner* — Sun Jae Yoo
(74) *Attorney, Agent, or Firm* — Hodgson Russ LLP

(57) ABSTRACT

Provided are oligothioetheramides (oligoTEAs) having a plurality of cationic groups, such as, for examples, cationic groups having guanidinium groups. The cationic oligoTEAs exhibit activity against gram-positive and gram-negative bacteria. The compounds can be used as antibacterial compounds against the same.

14 Claims, 43 Drawing Sheets

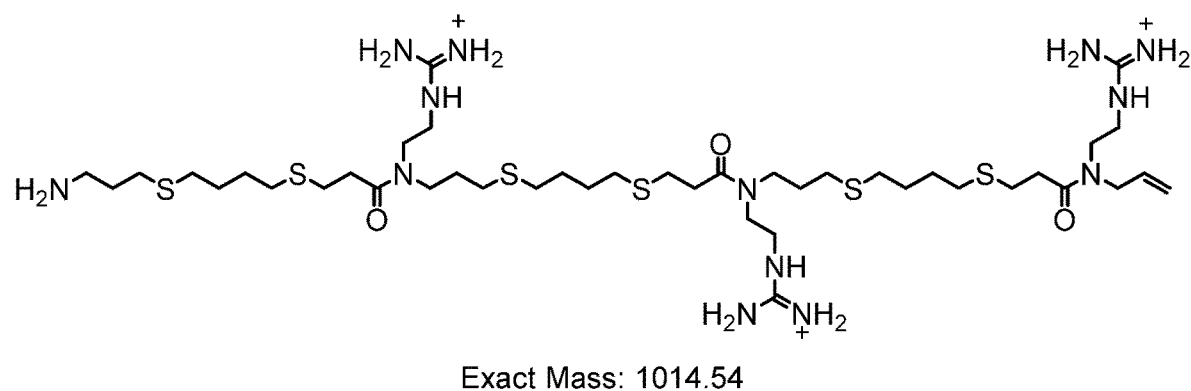
Exact Mass: 1014.54
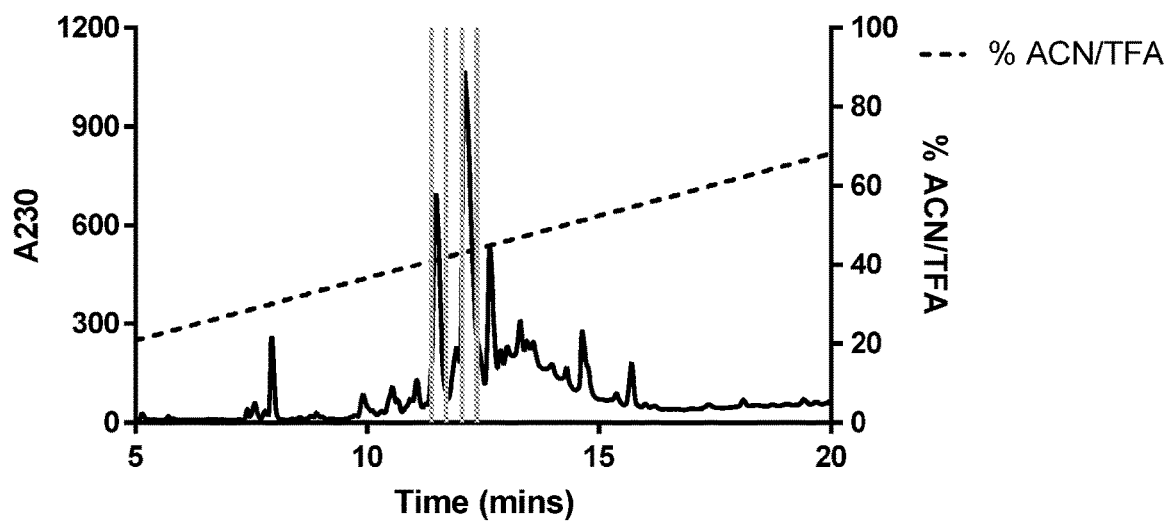
Figure 8

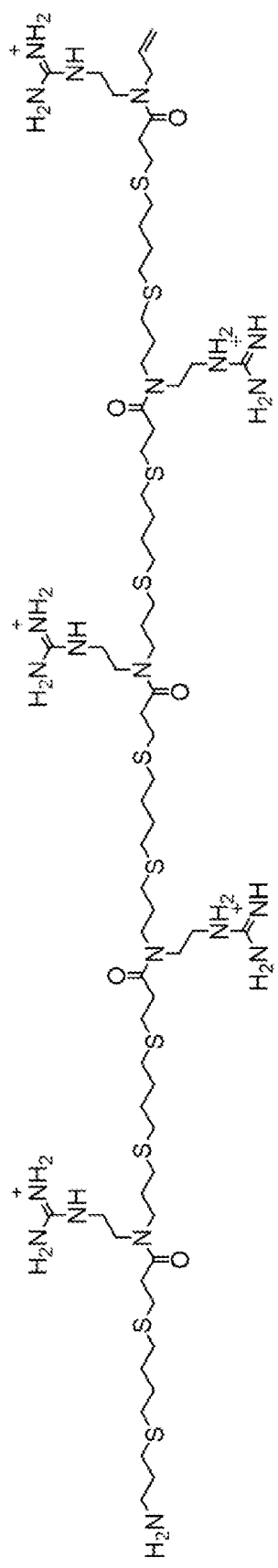
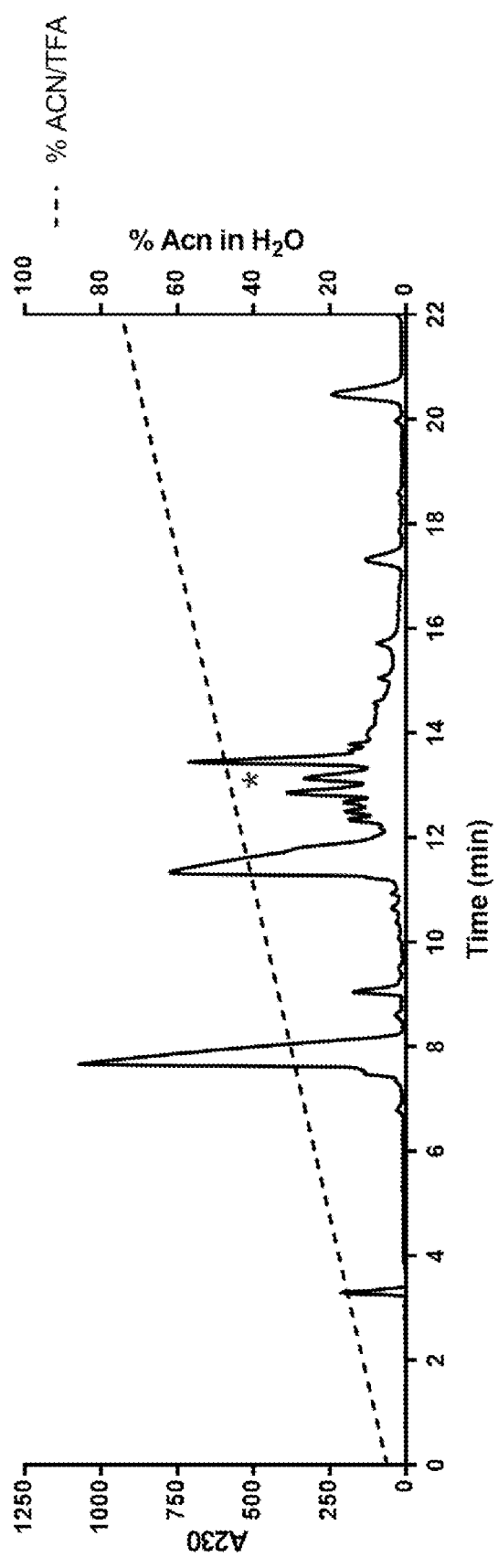
Figure 11

Investigational compound: BDG-4
Concentration range tested: 0.06 – 32 mcg/ml

| Isolate # | Organism ID | Phenotype | Date Tested | MIC (µg/ml) Vancomycin | MIC (µg/ml) Daptomycin | MIC (µg/ml) Meropenem | MIC (µg/ml) BDG-4 |
|---|---|---|---|---|---|---|---|
| ATCC 29213 | S. aureus | CLSI control | 3/13/17 | 0.5 | --- | --- | 2 |
| 6215 | MRSA | USA 100 | 3/13/17 | 1 | --- | --- | 2 |
| 6229 | MRSA | USA 300 | 3/13/17 | 0.5 | --- | --- | 2 |
| ATCC 29212 | E. faecalis | CLSI control | 3/13/17 | --- | 4 | --- | 2 |
| 1593 | E. faecium | VanA | 3/13/17 | --- | 4 | --- | 4 |
| 1788 | E. faecalis | VanB | 3/13/17 | --- | 1 | --- | 4 |
| ATCC 49619 | S. pneumoniae | CLSI control | 3/13/17 | 0.25 | --- | --- | >32 |
| MD77773 | S. pneumoniae | R: Pen | 3/13/17 | 0.25 | --- | --- | >32 |
| CC314937 | S. pneumoniae | R: Levo | 3/13/17 | 0.25 | --- | --- | 4 |
| 2006-41 | K. pneumoniae | ESBL, SHV-12 | 3/13/17 | --- | --- | ≤0.125 | 4 |
| 2008-16 | K. pneumoniae | ESBL, FQR | 3/13/17 | --- | --- | ≤0.125 | 2 |
| J4152 | K. pneumoniae | KPC-2 | 3/13/17 | --- | --- | 32 | 16 |
| ATCC 27853 | P. aeruginosa | CLSI Control | 3/13/17 | --- | --- | 0.5 | 8 |
| BB2013-100 | P. aeruginosa | FQR | 3/13/17 | --- | --- | 1 | 16 |
| J4228 | P. aeruginosa | R: Mero | 3/13/17 | --- | --- | >64 | 16 |
| 2004-51 | E. coli | FQR | 3/13/17 | --- | --- | ≤0.125 | 2 |
| J4243 (MVAST 072) | E. coli | --- | 3/13/17 | --- | --- | ≤0.125 | 2 |
| J4244 (J1886) | E. coli | --- | 3/13/17 | --- | --- | ≤0.125 | 2 |

*Streptococcus isolates tested in CA-MHB with 5% LHB

Figure 21

| Organism | MIC[1], μg/mL | | |
|---|---|---|---|
| | PDT-4G | BDT-4G | BDT-3G |
| MRSA (ATCC 33591™) | 1.0 | 0.5 | 2.0 |
| MRSA (ATCC 33591™) + serum | 0.75 | 1.0 | 3.0 |
| USA300 | 1.0 | 1.0 | 2.0 |
| USA300 + serum | 0.75 | 0.5 | 1.0 |
| E. coli O157:H7 | 2.0 | 2.0 | - |
| A. baumannii Lac-4 | 2.0 | 2.0 | - |

[1]MIC assays per NCLS guidelines in cation-adjusted MHB and TS

OLIGOTHIOETHERAMIDES (OLIGOTEAS) AS ANTI-MICROBIAL AND ANTI-BACTERIAL AGENTS

CROSS REFERENCE TO RELATED APPLICATIONS

This application claims priority to U.S. Provisional Application No. 62/546,905, filed on Aug. 17, 2017, the disclosure of which is hereby incorporated by reference.

STATEMENT REGARDING FEDERALLY SPONSORED RESEARCH

This invention was made with government support under contract no. CHE-1554046 awarded by the National Science Foundation. The government has certain rights in the invention.

FIELD OF THE DISCLOSURE

The disclosure generally relates to oligothioetheramides. More particularly the disclosure relates to cationic oligothioetheramides having antibacterial efficacy.

BACKGROUND OF THE DISCLOSURE

The natural ability of bacteria to evolve and develop resistance to the current suite of antibiotics is occurring at an alarming rate and posing a significant threat to public health and national security. The recent decline in the rate of new antibiotic development can be attributed to difficulties associated with their mode of discovery, structural complexity, and ability to access targets. Soil organisms, the traditional source of antibiotics, are mostly depleted due to over mining and synthetic medicinal approaches have been unable to keep pace with antibiotic need in part due to the structural complexity of these natural products. Finally, antibiotics that derive their specificity by targeting bacteria specific intracellular proteins and nucleic acids are difficult to develop due to poor intracellular penetration of organic compounds.

Antimicrobial peptides (AMPs) are small amphiphilic peptides (12-50 residues) composed of spatially segregated hydrophobic and cationic residues. AMPs are natural components of the innate host defense system and are capable of modulating host immune response as well as disrupting the lipid bilayer in the bacterial cell membrane. Bilayer disruption is the primary mode of cell death and occurs via nonspecific interactions with the bacterial membrane leading to membrane permeabilization and cell death. Additional events following bilayer disruption that may contribute to cell death include membrane depolarization and binding to cytoplasmic components. AMP specificity for bacteria over mammalian cells has been attributed to differences in surface charge and the large amount of cholesterol in the mammalian cell membrane, which has been shown to suppress bilayer disruption. Furthermore, since membrane permeabilization is driven by nonspecific AMP interaction with several essential lipids in the cell membrane, development of target resistance against this mechanism is expected to be very slow. Based on these promising attributes including their broad-spectrum activity and ease of preparation, AMPs have emerged as viable alternatives to conventional antibiotics. However, unlike traditional antibiotics, their potency and promise is attenuated due to their susceptibility to proteolytic degradation, toxicology profile and high preparation costs.

Towards this end, peptidomimetics with modified peptide backbones that are resistant to proteolysis such as β-peptides, α-AApeptides, γ-AApeptides, oligo-acyl-lysines, peptoids and others have been designed with helical, hydrophobic and amphiphilic properties requisite for antimicrobial activity. Furthermore, a wide variety of non-degradable synthetic polymers including polynorbornenes, lipid modified cyclobutene copolymers, Nylon-3 copolymers, poly (methacrylates), poly(arylamides), and other polymers as well as small molecular variants, have been created to mimic the properties and antibacterial activities of AMPs. Although these synthetic constructs are simpler and inexpensive to synthesize, they lack the precise sequence-definition of peptides and peptidomimetics.

In response to the urgent need for new antibiotic development strategies, antimicrobial peptides (AMPs) and other synthetic polymers are being actively investigated as promising alternatives to traditional antibiotics. Although most AMPs display lytic activity against several types of bacteria, they have poor toxicology profiles and are susceptible to proteolysis in vivo. While many synthetic variants have been created to mimic AMPs by tuning the hydrophobic to cationic ratio of the side-chain groups, few have decoupled the effects of charge from hydrophobicity in discrete systems, and none have investigated the effect of backbone hydrophobicity.

As a result, combating the decline in the rate of antibiotic development requires new modes of antibiotic discovery, preparation, and extracellular targets. Thus, there is a long-felt and unmet need for an effective, non-peptidic, and non-traditional antibiotic.

SUMMARY OF THE DISCLOSURE

The present disclosure provides compounds comprising alkyl thioethers and tertiary amides. The tertiary amides further comprise cationic groups, alkyl groups, aromatic groups, and heterocyclic groups. The cationic groups can be guanidinium groups. Such compounds can selectively can be used as antibacterial agents (e.g., an antibiotic) and antimicrobial compounds.

The compounds of the present disclosure are a new class of sequence-defined antimicrobial agents that selectively kills bacterial cells over mammalian cells by disrupting their membrane structure. The sequence defined agents (e.g., compounds) are based on oligothioetheramide (oligoTEA) chemistry and contain cationic and hydrophobic domains. The oligoTEAs are resistant to protease activity. The oligoTEA assembly scheme allows direct access to the oligomer backbone, which enables precise tuning of oligoTEA hydrophobicity while keeping charge constant. OligoTEAs of the present disclosure can be referred to as compounds.

In an aspect, the present disclosure provides compounds (e.g., oligoTEAs (e.g., an oligoTEA having a plurality of cationic groups)). The compounds comprise alkyl thioethers and tertiary amides. The tertiary amides further comprise cationic groups, alkyl groups, aromatic groups, and heterocyclic groups. The compounds can have end groups, which may be cleavable (e.g., cleavable by a trigger, such as, for example, a protease (e.g., a bacterial protease)).

The present disclosure provides compounds (e.g., oligoTEAs, such as, for example, an oligoTEA having a plurality of cationic groups) having the following structure:

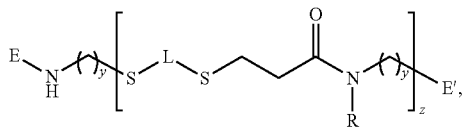

where z is 2-7, including all integer values and ranges therebetween (e.g., 2, 3, 4, 5, 6, 7); y independently at each occurrence is 2-10, including all integer values and ranges therebetween (e.g., 2, 3, 4, 5, 6, 7, 8, 9, 10); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

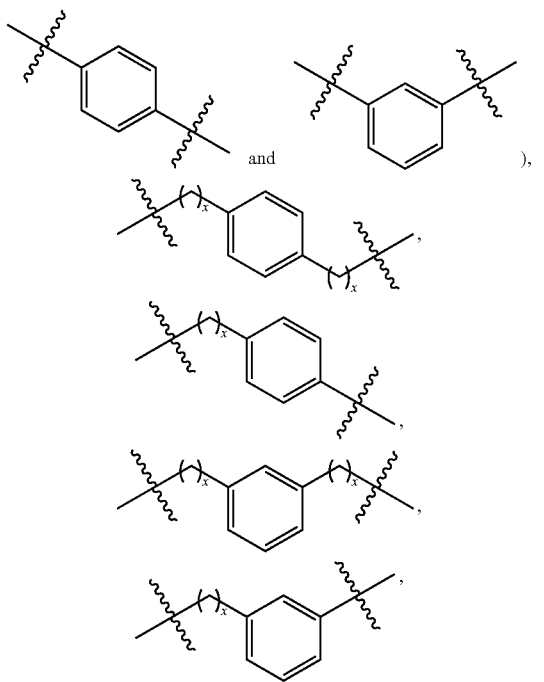

and the like, where x is 1-10, including all integer values and ranges therebetween (e.g., 1, 2, 3, 4, 5, 6, 7, 8, 9, 10)); E is a first end group chosen from H, a polymeric group (e.g., a hydrophilic polymeric group, such as, for example, derivatives of a polyethylene glycol (PEG) group, derivatives of a poly(vinyl alcohol) group, derivatives of a poly(N-vinyl pyrrolidone) group, derivatives of a poly(2-oxazoline) group, and the like, or a zwitterionic polymeric group, such as, for example, derivatives of a polysulfobetaine group, derivatives of a polycarboxybetaine group, derivatives of a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and

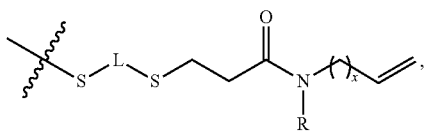

where x' is 0-6, including all integer values and ranges therebetween (e.g., 0, 1, 2, 3, 4, 5, 6). The compound has at least two cationic groups that are the same or different (e.g., the compound has two alkyl guanidinium groups, such as, for example,

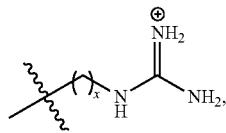

where x is 1, 2, 3, 4, 5, or 6). In an example, the compound has two alkyl guanidinium groups having the following structure:

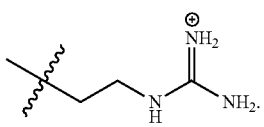 [SMILES: *CCNC(N)=[NH2+]]

In an aspect, the present disclosure provides compounds (e.g., oligoTEAs, such as, for example an oligoTEA having a plurality of cationic groups) having the following structure:

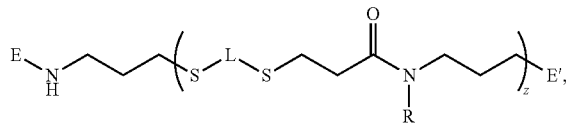

where z is 2-7, including all integer values and ranges therebetween (e.g., 2, 3, 4, 5, 6, 7); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

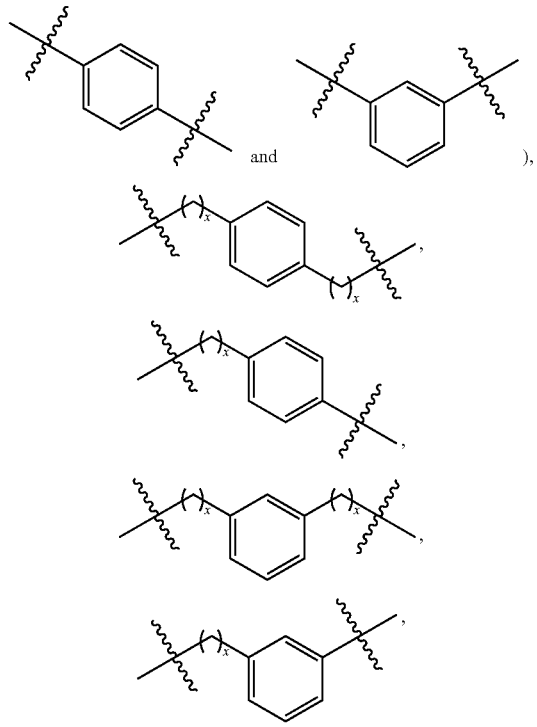

and the like, where x is 1-10, including all integer values and ranges therebetween (e.g., 1, 2, 3, 4, 5, 6, 7, 8, 9, 10)); E is a first end group chosen from H, a polymeric group (e.g., a hydrophilic polymeric group, such as, for example, derivatives of a polyethylene glycol (PEG) group, derivatives of a poly(vinyl alcohol) group, derivatives of a poly(N-vinyl pyrrolidone) group, derivatives of a poly(2-oxazoline) group, and the like, or a zwitterionic polymeric group, such as, for example, derivatives of a polysulfobetaine group, derivatives of a polycarboxybetaine group, derivatives of a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and

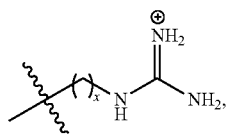

where x' is 0-6, including all integer values and ranges therebetween (e.g., 0, 1, 2, 3, 4, 5, 6). The compound has at least two cationic groups that are the same or different (e.g., the compound has two alkyl guanidinium groups, such as, for example

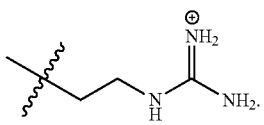

where x is 1, 2, 3, 4, 5, or 6). In an example, the compound has two alkyl guanidinium groups having the following structure In an aspect, the present disclosure provides compositions comprising at least one compound of the present disclosure. The compositions may further comprise one or more pharmaceutically acceptable carrier.

In an aspect, the present disclosure provides methods involving compounds of the present disclosure. Methods of the present disclosure may involve administering a compound of the present disclosure to a subject in need of treatment who has been diagnosed with or is suspected of having a bacterial infection (i.e., therapeutic use). A method can be carried out in a subject in need of prophylaxis for bacterial infections/illnesses. (e.g., a bacterial infection/illness caused by a gram positive and/or gram negative bacteria)

BRIEF DESCRIPTION OF THE FIGURES

For a fuller understanding of the nature and objects of the disclosure, reference should be made to the following detailed description taken in conjunction with the accompanying figures.

FIG. 8 shows (top) the structure of BDT-3G (composed of three 1,4 butanedithiol monomers and three guanidinium-based N-allylacrylamide monomers in a defined sequence) and (bottom) an HPLC trace of the cleavage reaction of Ftag-BDT-3G. The peaks at 11.5 and 12.2 min were collected, dried and checked by LC-MS.

FIG. 11 shows (top) the structure of BDT-5G (composed of five 1,4 butanedithiol monomers and five guanidinium-based N-allylacrylamide monomers in a defined sequence) and (bottom) an HPLC trace of the cleavage reaction of Ftag-BDT-5G. The peak at 13.4 min was collected, dried and checked by LC-MS.

FIG. 21 shows antibacterial activity data against a variety of gram positive and gram negative pathogens, measured as the minimum concentration required inhibit the growth of all bacteria (MIC100), of BDT-4G (referred to in this chart as BDG-4), Vancomycin, Daptomycin and Meropenem. BDG-4 is the same compound as BDT-4G.

DETAILED DESCRIPTION OF THE DISCLOSURE

Figure 1:
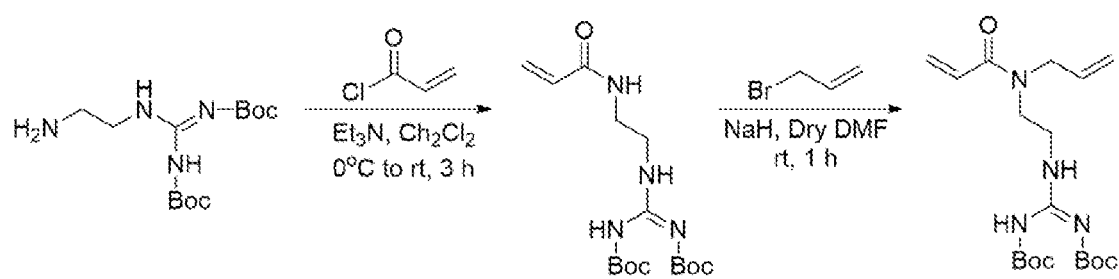
FIG. 1 shows a synthetic scheme of a Boc-protected guanidine monomer.

Although claimed subject matter will be described in terms of certain embodiments, other embodiments, including embodiments that do not provide all of the benefits and features set forth herein, are also within the scope of this disclosure. Various structural, logical, and process step, changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise stated, the term "group" refers to a chemical entity that has one terminus that can be covalently bonded to other chemical species. Examples of groups include, but are not limited to:

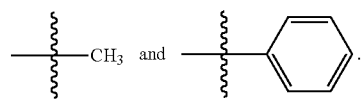

As used herein, unless otherwise stated, the term "moiety" refers to a chemical entity that has two or more termini that can be covalently bonded to other chemical species. Examples of moieties include, but are not limited to:

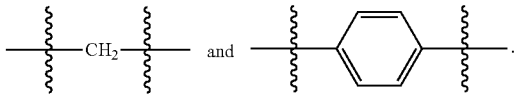

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic groups/moieties are a $C_1$ to $C_{40}$ aliphatic group/moiety, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, and $C_{40}$). The aliphatic group/moiety can be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, nitro groups, carboxylate groups, carboxylic acids, ether groups, alcohol groups, alkyne groups (e.g., acetylenyl groups and the like), and the like, and combinations thereof.

As used herein, unless otherwise indicated, the term "alkyl" refers to branched or unbranched, linear saturated hydrocarbon groups/moieties and/or cyclic hydrocarbon groups/moieties. Examples of alkyl groups/moieties include, but are not limited to, methyl groups/moieties, ethyl groups/moieties, propyl groups/moieties, butyl groups/moieties, isopropyl groups/moieties, tert-butyl groups/moieties, cyclopropyl groups/moieties, cyclopentyl groups/moieties, cyclohexyl groups/moieties, and the like. Alkyl groups/moieties are saturated groups/moieties, unless it is a cyclic group/moiety. For example, the alkyl groups/moieties are a $C_1$ to $C_{40}$ alkyl group/moiety, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, and $C_{40}$). The alkyl group/moiety can be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, nitro groups, carboxylate groups, carboxylic acids, ether groups, alcohol groups, alkyne groups (e.g., acetylenyl groups and the like), and the like, and combinations thereof.

As used herein, unless otherwise indicated, the term "aromatic" refers to $C_5$ to $C_{30}$, including all integer numbers of carbons and ranges of numbers of carbons therebetween (e.g., $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$), aromatic or partially aromatic carbocyclic groups/moieties. An aromatic group/moiety can also be referred to as an aromatic group/moiety. The aromatic groups/moieties can comprise polyaryl moieties such as, for example, fused ring or biaryl moieties. The aromatic group/moiety can be unsubstituted or substituted with one or more substituent. Examples of substituents include, but are not limited to, substituents such as, for example, halogens (—F, —Cl, —Br, and —I), aliphatic groups (e.g., alkenes, alkynes, and the like), aryl groups, alkoxides, carboxylates, carboxylic acids, ether groups, and the like, and combinations thereof. Examples of aromatic groups/moieties include, but are not limited to, phenyl groups/moieties, biaryl groups/moieties (e.g., biphenyl groups/moieties and the like), and fused ring groups/moieties (e.g., naphthyl groups/moieties and the like).

As used herein, unless otherwise indicated, the term "heterocyclic group" refers to $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) cyclic groups containing one or more heteroatoms (e.g., N, O, S, or the like) as part of the ring structure. The heterocyclic groups may be substituted or unsubstituted and/or have additional degrees of unsaturation. The heterocyclic group can be a fused ring (e.g., a pyrrolizidinyl group). Non-limiting examples of heterocyclic groups include furanyl groups, oxazolyl groups, isothiazolyl groups, thiazolyl groups, tetrahydropyranyl groups, piperazinyl groups, dioxanyl groups, pyrrolidinyl groups, tetrahydrothiophenyl groups, tetrahydrofuranyl groups, quinuclidinyl groups, azaadamantanyl groups, decahydroquinolinyl groups, and the like.

As used herein, unless otherwise indicated, the term "cationic group" refers to a group having at least one positive charge or capable of having a positive charge at a protonated group. In an illustrative example, a guanidinium group is protonated such that is has a positive charge at a pH of and up to about 13. Non-limiting examples of a cationic groups include guanidinium groups (e.g.,

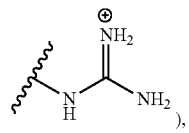 [SMILES: *NC(N)=[NH2+]]

), ammonium groups (e.g., protonated primary, secondary, or tertiary amines), quaternary amine groups, phosphonium groups, sulfonium groups, imidazolium groups, thiazolium groups, pyrazolium groups, and the like. Cationic groups also refer to cationic groups attached (e.g., covalently bonded to) aliphatic moieties. Thus, cationic groups further include, but are not limited to, aliphatic (e.g., alkyl) guanidinium groups, aliphatic ammonium groups (e.g., protonated primary, secondary, or tertiary amines), aliphatic quaternary amine groups, aliphatic phosphonium groups, aliphatic sulfonium groups, aliphatic imidazolium groups, aliphatic thiazolium groups, aliphatic pyrazolium groups, and the like. For example, a guanidinium group is an aliphatic (e.g., alkyl) guanidinium group of the present disclosure and has the following structure:

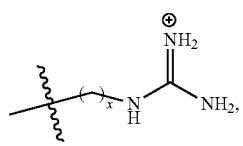

where x is 1, 2, 3, 4, 5, or 6. In an example, the aliphatic (e.g., alkyl) guanidinium group is

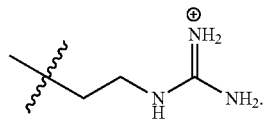 [SMILES: *CCNC(N)=[NH2+]]

As used herein, unless otherwise indicated, the term "linking moiety" refers to a moiety linking two atoms, such as, for example, two sulfur atoms. Non-limiting examples of linking moieties include aliphatic moieties (e.g., alkylene moieties, such as, for example, methylene, ethylene, propylene, butylene, and the like; alkenylene moieties; and alkynylene moieties), aromatic moieties (e.g., phenylene, such as, for example

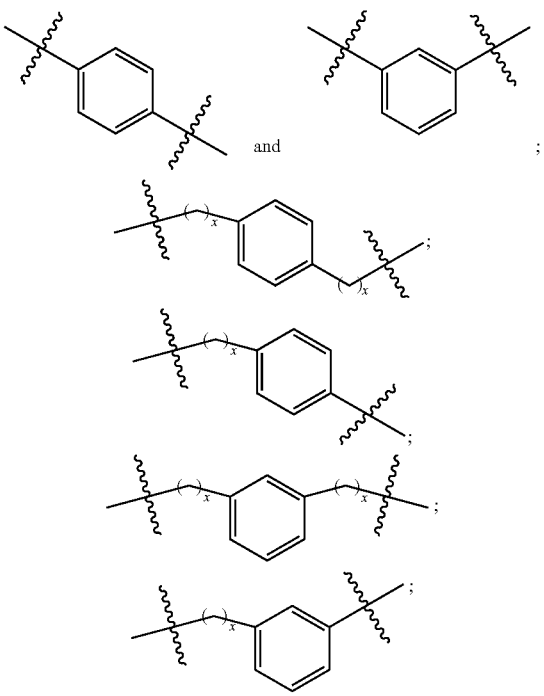

and the like, where x is 1-10, including all integer values and ranges therebetween (e.g., 1, 2, 3, 4, 5, 6, 7, 8, 9, and 10), and the like.

As used herein, unless otherwise indicated, the term "monomer" refers to molecule having two electrophilic groups (e.g., two olefins) and a cationic group, an alkyl group, an aromatic group, or heterocyclic group, such as, for example, an N-allylacrylamide having a cationic group, an alkyl group, an aromatic group, or heterocyclic group on the amide nitrogen (e.g., a Boc-protected guanidine monomer, such as in FIG. 1). For example, the cationic monomer has the following structure:

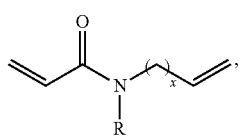

where x is 0-6, including all integer values and ranges therebetween (e.g., 0, 1, 2, 3, 4, 5, 6); R is chosen from a cationic group, a linear or branched aliphatic group (e.g., a linear or branched alkyl group), an aromatic group, or heterocyclic group.

As used herein, unless otherwise indicated, the term "dithiol" refers to a molecule having two thiol groups. Non-limiting examples of dithiols include alkyl dithiols (e.g.,

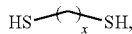

where x is 1-10, including all integer values and ranges therebetween (e.g., 1, 2, 3, 4, 5, 6, 7, 8, 9, and 10)) and aromatic dithiols (e.g.,

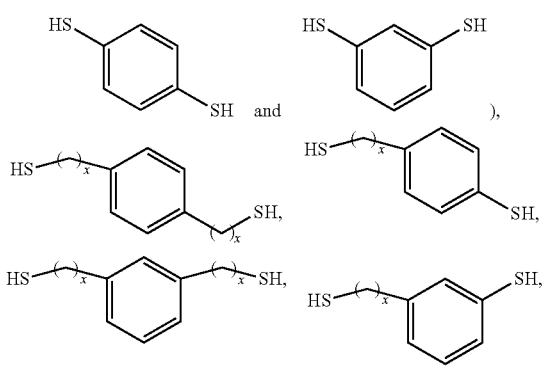

where x is 1-10, including all integer values and ranges therebetween (e.g., 1, 2, 3, 4, 5, 6, 7, 8, 9, and 10)) and the like.

As used herein, unless otherwise indicated, the term "end group" refers to a terminal group on a compound of the present disclosure. Non-limiting examples of end group are H, a polymeric group (e.g., derivatives of hydrophilic polymeric groups, such as, for example, derivatives of polyethylene glycol (PEG) group, derivatives of poly(vinyl alcohol) group, derivatives of poly(N-vinyl pyrrolidone) group, derivatives of poly(2-oxazoline) group, and the like, or derivatives of zwitterionic polymeric groups, such as, for example, derivatives of polysulfobetaine group, derivatives of polycarboxybetaine group, derivatives of polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), a cationic group, alkyl group, aromatic group, and a heterocyclic group, and

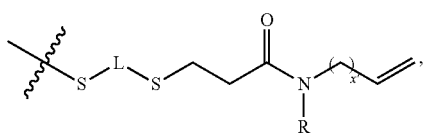

where x' is 0-6, including all integer values and ranges therebetween (e.g., 0, 1, 2, 3, 4, 5, 6). End groups can comprise polymeric groups attached (e.g., covalently bonded) to cleavable moieties (e.g., cleavable peptides). End groups can be cleavable (e.g., cleaved from the compound by a trigger, such as, for example, cleaved by a protease, such as, for example, a bacterial protease, such as, for example, Sortase A, aureolysin, glutamyl endopeptidase I, and/or the like). Compounds having a cleavable end group can be prodrugs prior to the cleavage of the cleavable end group.

As used herein, unless otherwise indicated, the term "polymeric group" refers to a group having a repeating structure. Polymeric groups can be end groups. Polymeric groups may further be cleaved under specific conditions. Examples of polymeric groups include, but are not limited to derivatives of hydrophilic polymeric groups, such as, for example, derivatives of polyethylene glycol (PEG) group (e.g.,

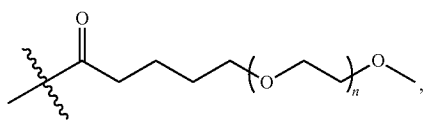

where n is 1-250, including all integer values and ranges therebetween), derivatives of poly(vinyl alcohol) group, derivatives of poly(N-vinyl pyrrolidone) group, derivatives of poly(2-oxazoline) group, and the like, or derivatives of zwitterionic polymeric groups, such as, for example, derivatives of polysulfobetaine group, derivatives of polycarboxybetaine group, derivatives of polyphosphorylcholine group, and the like. In an example, a polymeric group (e.g., a PEG group) is attached (e.g., covalently bonded) to a cleavable moiety (e.g., a cleavable peptide, such as, for example, a peptide cleavable by a protease such as, for example, by a bacterial protease, such as, for example, Sortase A, aureolysin, glutamyl endopeptidase I, and/or the like), that is attached (e.g., covalently bonded) to the compound.

The present disclosure provides compounds comprising alkyl thioethers and tertiary amides. The tertiary amides further comprise cationic groups, alkyl groups, aromatic groups, and heterocyclic groups. The cationic groups can be guanidinium groups. Such compounds can selectively can be used as antibacterial agents (e.g., an antibiotic) and antimicrobial compounds.

In an aspect, the present disclosure provides compounds (e.g., oligoTEAs (e.g., an oligoTEA having a plurality of cationic groups)). The compounds comprise alkyl thioethers and tertiary amides. The tertiary amides further comprise cationic groups, alkyl groups, aromatic groups, and heterocyclic groups. The compounds can have end groups, which may be cleavable (e.g., cleavable by a trigger, such as, for example, an enzyme).

The present disclosure provides compounds (e.g., oligoTEAs, such as, for example, an oligoTEA having a plurality of cationic groups) having the following structure:

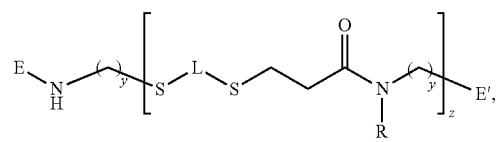

where z is 2-7, including all integer values and ranges therebetween (e.g., 2, 3, 4, 5, 6, 7); y independently at each occurrence is 2-10, including all integer values and ranges therebetween (e.g., 2, 3, 4, 5, 6, 7, 8, 9, 10); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

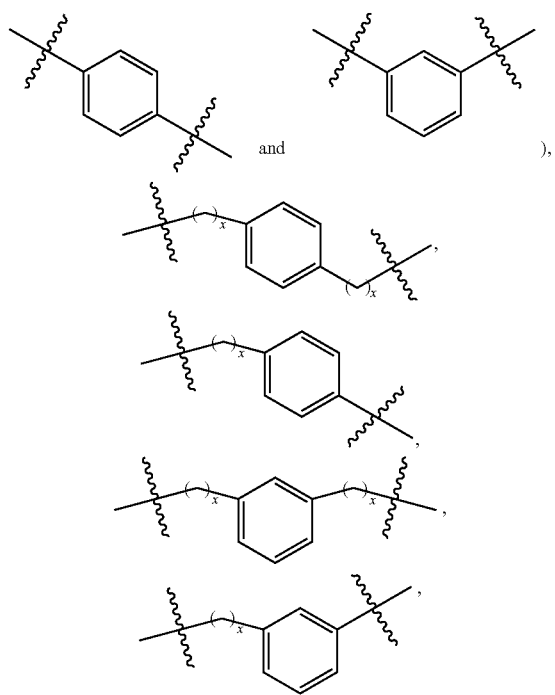

and the like, where x is 1-10, including all integer values and ranges therebetween (e.g., 1, 2, 3, 4, 5, 6, 7, 8, 9, 10)); E is a first end group chosen from H, a polymeric group (e.g., a hydrophilic polymeric group, such as, for example, derivatives of a polyethylene glycol (PEG) group, derivatives of a poly(vinyl alcohol) group, derivatives of a poly(N-vinyl pyrrolidone) group, derivatives of a poly(2-oxazoline) group, and the like, or a zwitterionic polymeric group, such as, for example, derivatives of a polysulfobetaine group, derivatives of a polycarboxybetaine group, derivatives of a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and

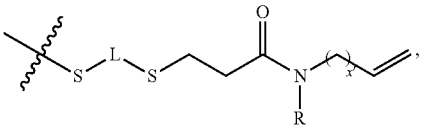

where x' is 0-6, including all integer values and ranges therebetween (e.g., 0, 1, 2, 3, 4, 5, 6). The compound has at least two cationic groups that are the same or different (e.g., the compound has two alkyl guanidinium groups, such as, for example,

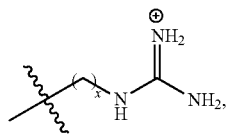

where x is 1, 2, 3, 4, 5, or 6). In an example, the compound has two alkyl guanidinium groups having the following structure:

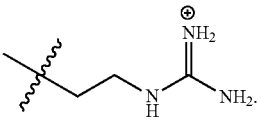 [SMILES: *CCNC(N)=[NH2+]]

In an aspect, the present disclosure provides compounds (e.g., oligoTEAs, such as, for example an oligoTEA having a plurality of cationic groups) having the following structure:

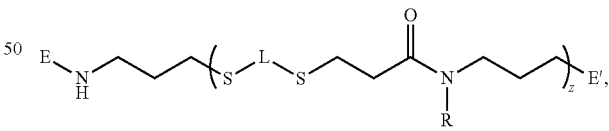

where z is 2-7, including all integer values and ranges therebetween (e.g., 2, 3, 4, 5, 6, 7); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

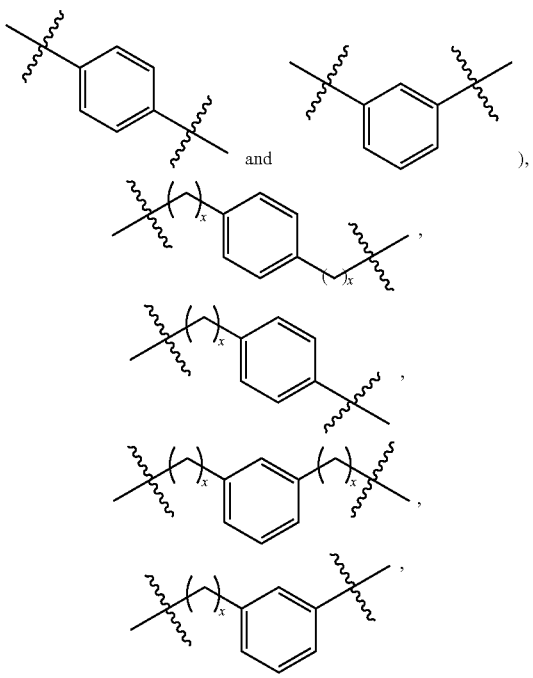

and the like, where x is 1-10, including a integer values an ranges therebetween e.g., 1, 2, 3, 4, 5, 6, 7, 8, 9, 10)); E is a first end group chosen from H, a polymeric group (e.g., a hydrophilic polymeric group, such as, for example, derivatives of a polyethylene glycol (PEG) group, derivatives of a poly(vinyl alcohol) group, derivatives of a poly(N-vinyl pyrrolidone) group, derivatives of a poly(2-oxazoline) group, and the like, or a zwitterionic polymeric group, such as, for example, derivatives of a polysulfobetaine group, derivatives of a polycarboxybetaine group, derivatives of a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and

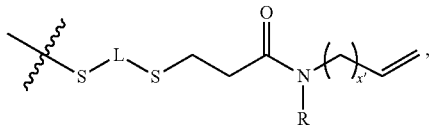

where x' is 0-6, including all integer values and ranges therebetween (e.g., 0, 1, 2, 3, 4, 5, 6). The compound has at least two cationic groups that are the same or different (e.g., the compound has two alkyl guanidinium groups, such as, for example,

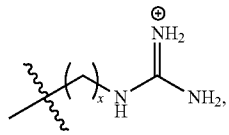

where x is 1, 2, 3, 4, 5, or 6). In an example, the compound has two alkyl guanidinium groups having the following structure:

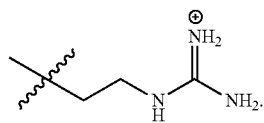 [SMILES: *CCNC(N)=[NH2+]]

In an example, the compounds have the following structure:

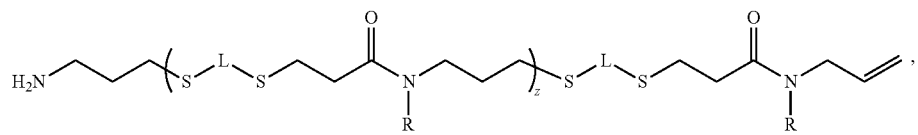

where z independently at each occurrence is 1-7 (e.g., 1, 2, 3, 4, 5, 6, 7), including all integer values and ranges therebetween; R independently at each occurrence is defined as herein; and L independently at each occurrence is defined as herein. The compound has at least two cationic groups that are the same or different. In an example, both of the cationic groups comprise guanidinium groups (e.g., a cationic group having the structure:

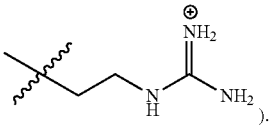 [SMILES: *CCNC(N)=[NH2+]]

In another example, L is

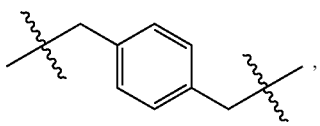

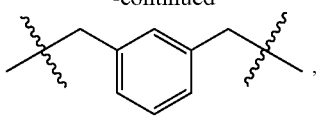, or a combination thereof.

In an example, the compounds have the following structure:

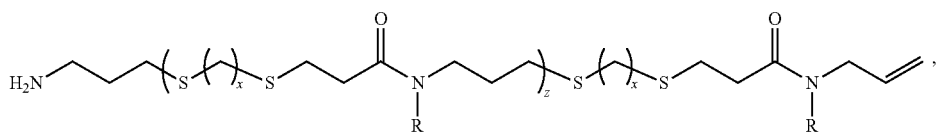

where x independently at each occurrence is 2-10, including all integer values and ranges therebetween (e.g., 2, 3, 4, 5, 6, 7, 8, 9, 10); z is 1-7, including all integer values and ranges therebetween (e.g., 1, 2, 3, 4, 5, 6, 7); and R independently at each occurrence is defined as herein. The compound has at least two cationic groups that are the same or different. In an example, both of the cationic groups comprise guanidinium groups (e.g., a cationic group having the structure:

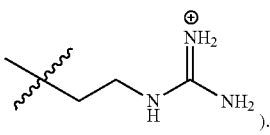).

In an example, the compounds have the following structure:

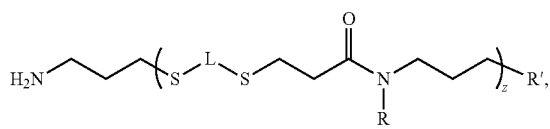

where z independently at each occurrence is 2-7, including all integer values and ranges therebetween (e.g., 2, 3, 4, 5, 6, 7); R independently at each occurrence defined as herein; R' is defined as herein; and L independently at each occurrence is defined as herein. The compound has at least two cationic groups that are the same or different. In an example, both of the cationic groups comprise guanidinium groups (e.g., a cationic group having the structure:

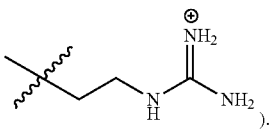).

In another example, L is

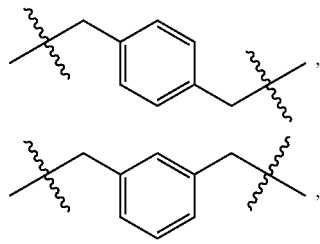, or a combination thereof. In another example, R' is a methyl group.

In an example, the compounds have the following structure:

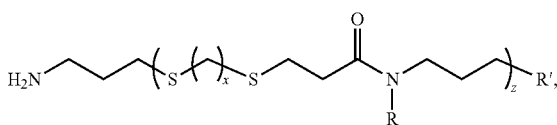, where x independently at each occurrence is 2-10, including all integer values and ranges therebetween (e.g., 2, 3, 4, 5, 6, 7, 8, 9, 10); z is 2-7, including all integer values and ranges therebetween (e.g., 2, 3, 4, 5, 6, 7); R independently at each occurrence is defined as herein; and R' is defined as herein. The compound has at least two cationic groups that are the same or different. In an example, both of the cationic groups comprise guanidinium groups (e.g., a cationic group having the structure:

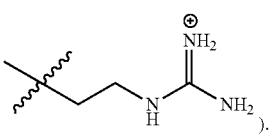 [SMILES: *CCNC(N)=[NH2+]]).

In another example, R' is a methyl group.

In an example, the compounds have the following structure:

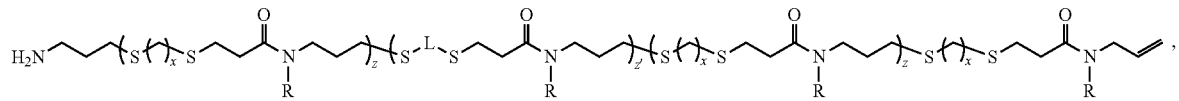

where x independently at each occurrence is 2-10, including a integer values an ranges therebetween (e.g., 2, 3, 4, 5, 6, 7, 8, 9, 10); z independently at each occurrence is 0-7, including all integer values and ranges therebetween (e.g., 0, 1, 2, 3, 4, 5, 6, 7); z' independently at each occurrence is 1-7, including all integer values and ranges therebetween (e.g., 1, 2, 3, 4, 5, 6, 7); R independently at each occurrence is defined as herein; and L independently at each occurrence is defined as herein. The compound has at least two cationic groups that are the same or different. In an example, both of the cationic groups comprise guanidinium groups (e.g., a cationic group having the structure:

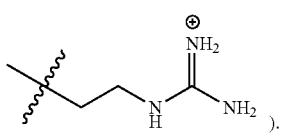 [SMILES: *CCNC(N)=[NH2+]]

In an example, the compounds have the following structure:

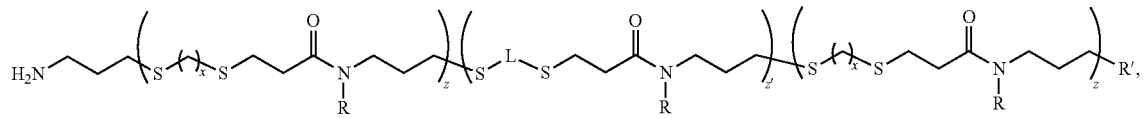

where x independently at each occurrence is 2-10, including all integer values and ranges therebetween (e.g., 2, 3, 4, 5, 6, 7, 8, 9, 10); z independently at each occurrence is 0-7, including all integer values and ranges therebetween (e.g., 0, 1, 2, 3, 4, 5, 6, 7); z' independently at each occurrence is 1-7, including all integer values and ranges therebetween (e.g., 1, 2, 3, 4, 5, 6, 7), where the sum of z and z' is at least 2; R independently at each occurrence is defined as herein; R' is defined as herein; and L independently at each occurrence is defined as herein. The compound has at least two cationic groups that are the same or different. In an example, both of the cationic groups comprise guanidinium groups (e.g., a cationic group having the structure:

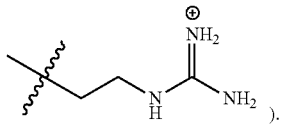

In another example, R' is a methyl group.
In an example, the compounds have the following structure:

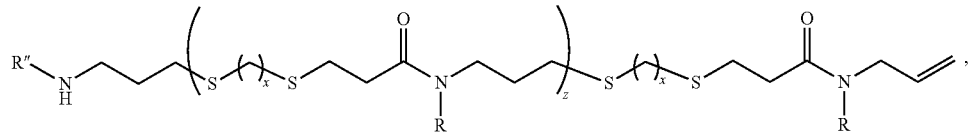

where x independently at each occurrence is 2-10, including all integer values and ranges therebetween (e.g., 2, 3, 4, 5, 6, 7, 8, 9, 10); z is 1-7, including all integer values and ranges therebetween (e.g., 1, 2, 3, 4, 5, 6, 7); R independently at each occurrence is defined as herein; and R" is chosen from a polymeric group (e.g., a hydrophilic polymeric group, such as, for example, a polyethylene glycol (PEG) group, a poly(vinyl alcohol) group, a poly(N-vinyl pyrrolidone) group, a poly(2-oxazoline) group, and the like, or a zwitterionic polymeric group, such as, for example, a polysulfobetaine group, a polycarboxybetaine group, a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like). The compound has at least two cationic groups that are the same or different. In an example, both of the cationic groups comprise guanidinium groups (e.g., a cationic group having the structure:

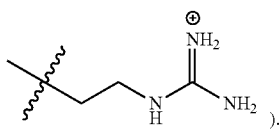 [SMILES: *CCNC(N)=[NH2+]]

In an example, the compounds have the following structure:

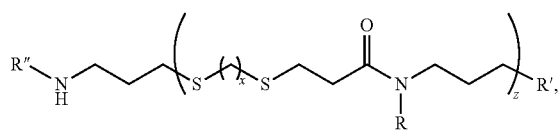

where x independently at each occurrence is 2-10, including all integer values and ranges therebetween (e.g., 2, 3, 4, 5, 6, 7, 8, 9, 10); z is 1-7, including all integer values and ranges therebetween (e.g., 1, 2, 3, 4, 5, 6, 7); R independently at each occurrence is defined as herein; R' is defined as herein; and R" is defined as herein. The compound has at least two cationic groups that are the same or different. In an example, both of the cationic groups comprise guanidinium groups (e.g., a cationic group having the structure:

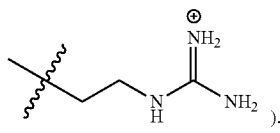 [SMILES: *CCNC(N)=[NH2+]]

In another example, R' is a methyl group.

In an example, the compounds have the following structure:

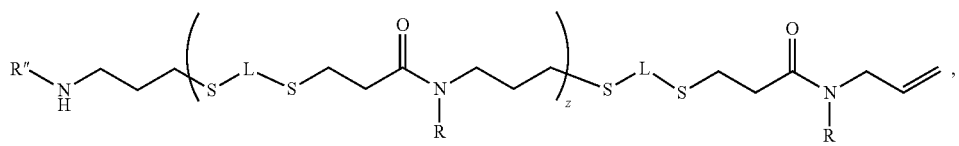

where z independently at each occurrence is 1-7, including all integer values and ranges therebetween (e.g., 1, 2, 3, 4, 5, 6, 7); R independently at each occurrence is defined as herein; R" is defined as herein; and L independently at each occurrence is defined as herein. The compound has at least two cationic groups that are the same or different. In an example, both of the cationic groups comprise guanidinium groups (e.g., a cationic group having the structure:

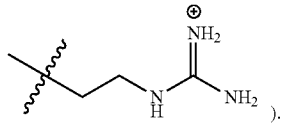

In another example, L is

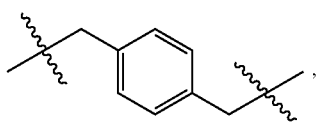

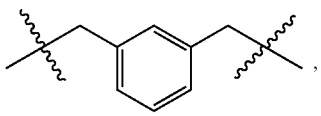

or a combination thereof. In another example, R" is

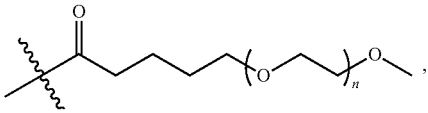

where n is 1-250 including all integer values and ranges therebetween.

In an example, the compounds have the following structure:

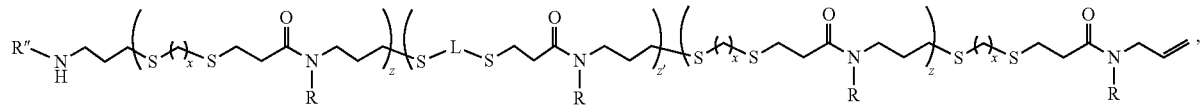

where x independently at each occurrence is 2-10, including all integer values and ranges therebetween (e.g., 2, 3, 4, 5, 6, 7, 8, 9, 10); z independently at each occurrence is 0-7, including all integer values and ranges therebetween (e.g., 0, 1, 2, 3, 4, 5, 6, 7); z' independently at each occurrence is 1-7, including all integer values and ranges therebetween (e.g., 1, 2, 3, 4, 5, 6, 7); R independently at each occurrence is defined as herein; R" is defined as herein; and L independently at each occurrence is defined as herein. The compound has at least two cationic groups that are the same or different. In an example, both of the cationic groups comprise guanidinium groups (e.g., a cationic group having the structure:

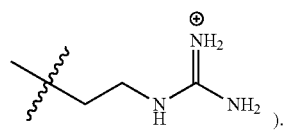

In another example, L is

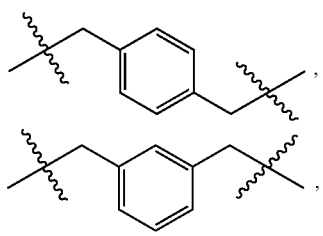

or a combination thereof. In another example, R" is

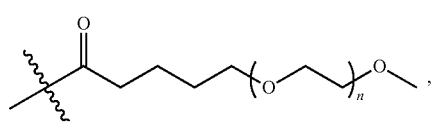

where n is 1-250 including all integer values and ranges therebetween.

In an example, the compounds have the following structure:

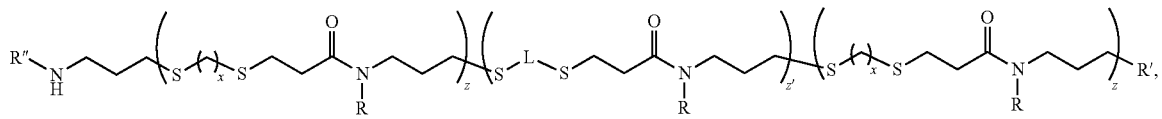

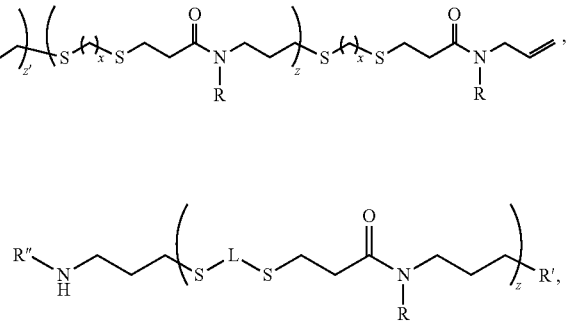

where z independently at each occurrence is 2-7, including all integer values and ranges therebetween (e.g., 2, 3, 4, 5, 6, 7); R independently at each occurrence is defined as herein; R' is defined as herein; R" is defined as herein; and L independently at each occurrence is defined as herein. The compound has at least two cationic groups that are the same or different. In an example, both of the cationic groups comprise guanidinium groups (e.g., a cationic group having the structure:

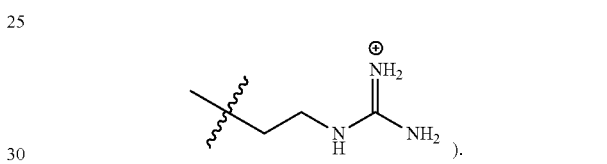

In another example, L is

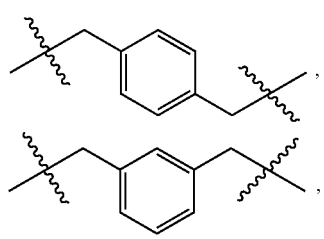

or a combination thereof. In another example, R" is

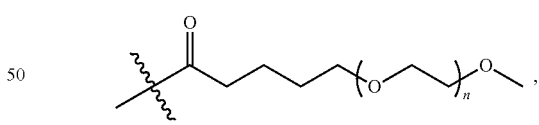

where n is 1-250 including all integer values and ranges therebetween.

In an example, the compounds have the following structure:

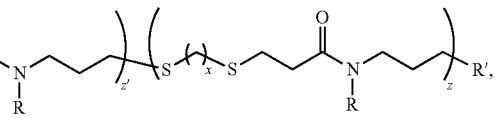

where x independently at each occurrence is 2-10, including a integer values an ranges therebetween (e.g., 2, 3, 4, 5, 6, 7, 8, 9, 10); z independently at each occurrence is 0-7, including all integer values and ranges therebetween (e.g., 0, 1, 2, 3, 4, 5, 6, 7); z' independently at each occurrence is 1-7, including all integer values and ranges therebetween (e.g., 1, 2, 3, 4, 5, 6, 7), where the sum of z and z' is at least 2; R independently at each occurrence is defined as herein; R' is defined as herein; R" is defined as herein; and L independently at each occurrence is defined as herein. The compound has at least two cationic groups that are the same or different. In an example, both of the cationic groups comprise guanidinium groups (e.g., a cationic group having the structure:

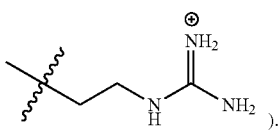).

In another example, R' is a methyl group. In another example, L is

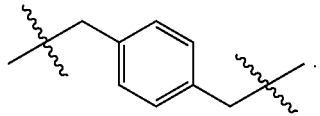 [SMILES: *Cc1ccc(C*)cc1].

In another example, R" is

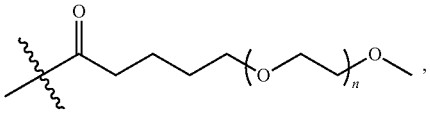, where n is 1-250 including all integer values and ranges therebetween.

In an example, the compounds have the following structure:

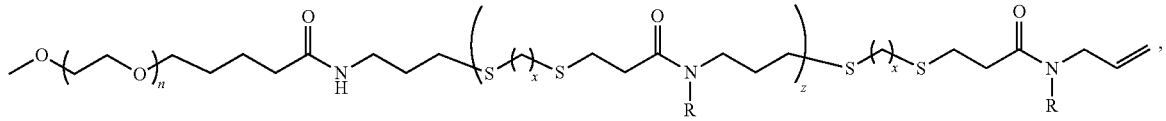

where x independently at each occurrence is 2-10, including all integer values and ranges therebetween (e.g., 2, 3, 4, 5, 6, 7, 8, 9, 10); z is 1-7, including all integer values and ranges therebetween (e.g., 1, 2, 3, 4, 5, 6, 7); n is 1-250, including all integer values and ranges therebetween; and R independently at each occurrence is defined as herein. The compound has at least two cationic groups that are the same or different. In an example, both of the cationic groups comprise guanidinium groups (e.g., a cationic group having the structure:

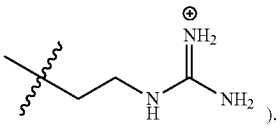 [SMILES: *CCNC(N)=[NH2+]]).

In an example, the present disclosure provides compounds having the following structure:

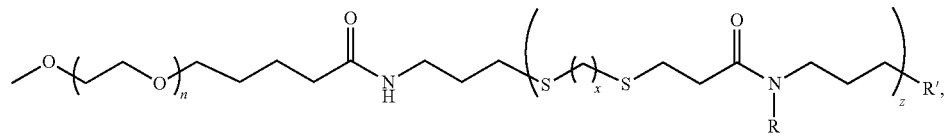

where x independently at each occurrence is 2-10, including all integer values and ranges therebetween (e.g., 2, 3, 4, 5, 6, 7, 8, 9, 10); z is 2-7, including all integer values and ranges therebetween (e.g., 2, 3, 4, 5, 6, 7); n is 1-250, including all integer values and ranges therebetween; R independently at each occurrence is chosen from cationic groups, alkyl groups, aromatic groups, and heterocyclic groups; and R' is chosen from hydrogen, a cationic group, alkyl group, aromatic group, and heterocyclic groups. The compound has at least two cationic groups that are the same or different. In an example, both of the cationic groups are guanidinium groups. In another example, R' is a methyl group.

In an example, the oligoTEA has a structure identified as PDT-4G, synthesized from four 1,3-propanedithiol units and four guanidinium-based N-allylacrylamide monomers in a defined sequence, and BDT-4G, synthesized from of four 1,4-butanedithiol units and four guanidinium-based N-allylacrylamide monomers in a defined sequence.

In other examples, the oligoTEA comprises two or more (e.g., three or more) cationic (e.g., groups comprising a guanidinium group) groups.

In other examples, the oligoTEA further comprises a fluorescent group (e.g., a fluorescent tag or label).

In an example, a compound of the present disclosure is a prodrug. Upon interaction with a specific trigger (e.g., a protease, such as, for example, a bacterial protease, such as, for example, Sortase A, aureolysin, and glutamyl endopeptidase I), a cleavable group (e.g., a cleavable end group) is cleaved from the compound.

In an example, a compound of the present disclosure has the following structure:

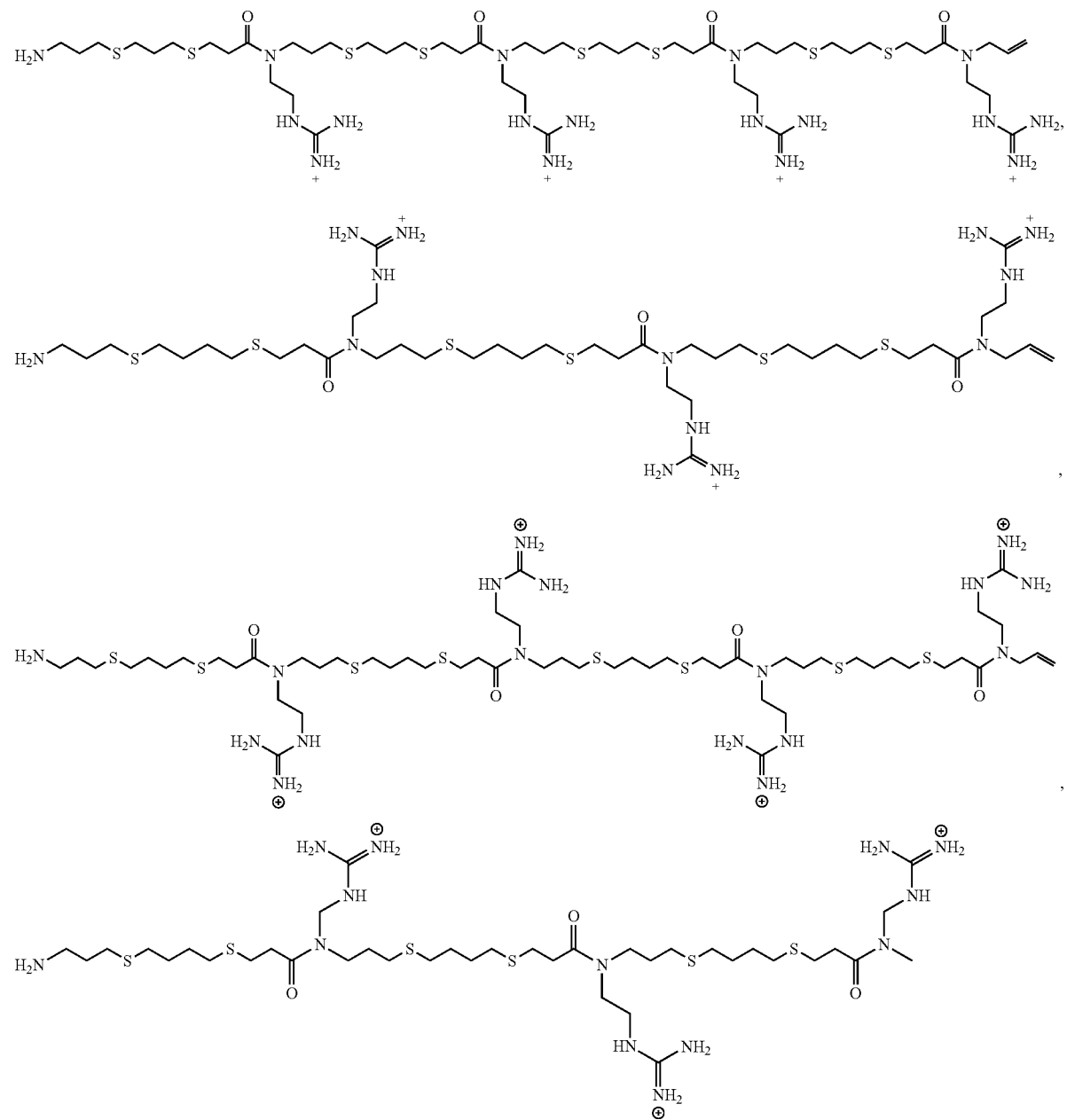

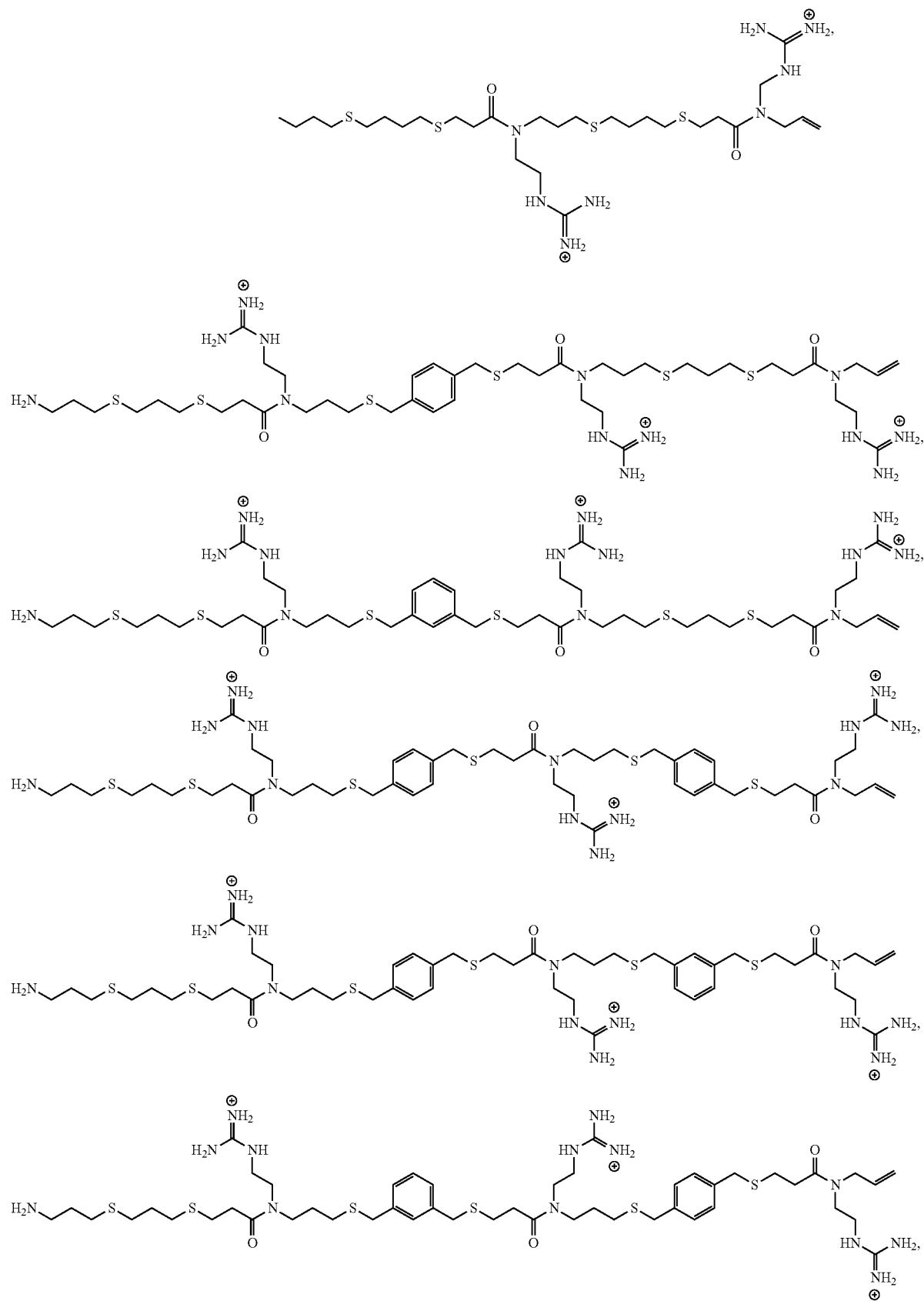

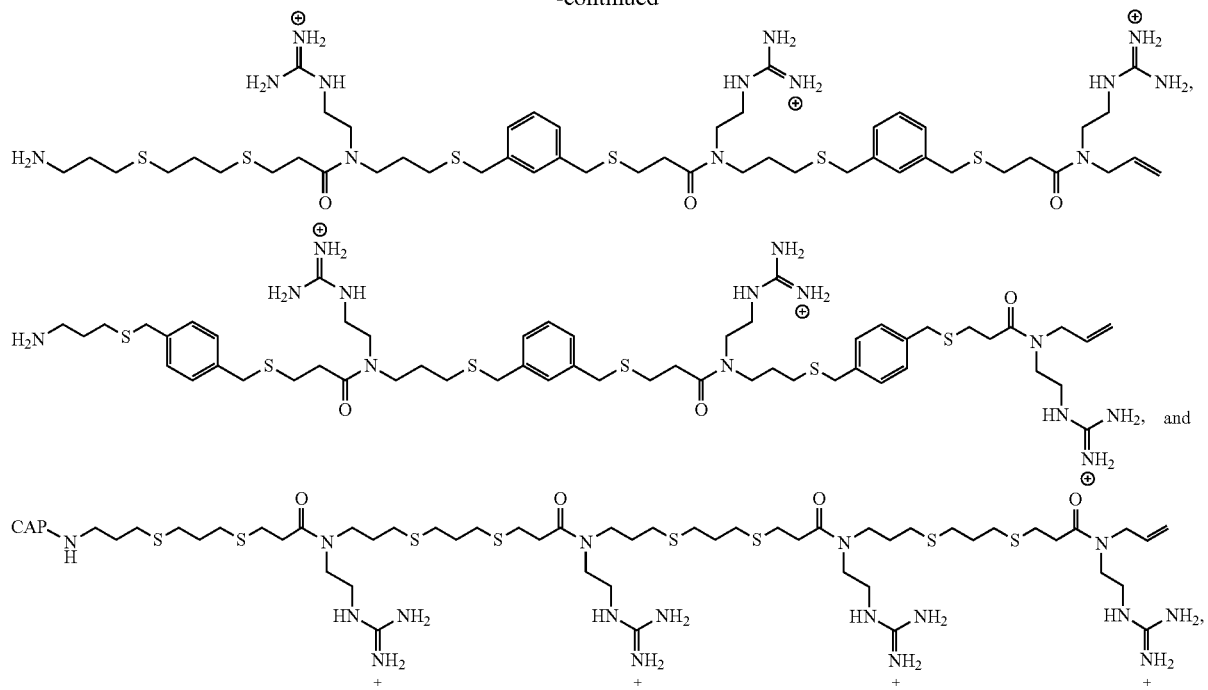

where CAP is

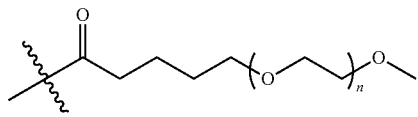

and n is 1-250.

In an example, R" groups can be cleaved from a compound of the present disclosure. Various triggers can be used to cleave the R" group. In an example, R" comprises a cleavable moiety (e.g., a cleavable peptide).

Figure 2:
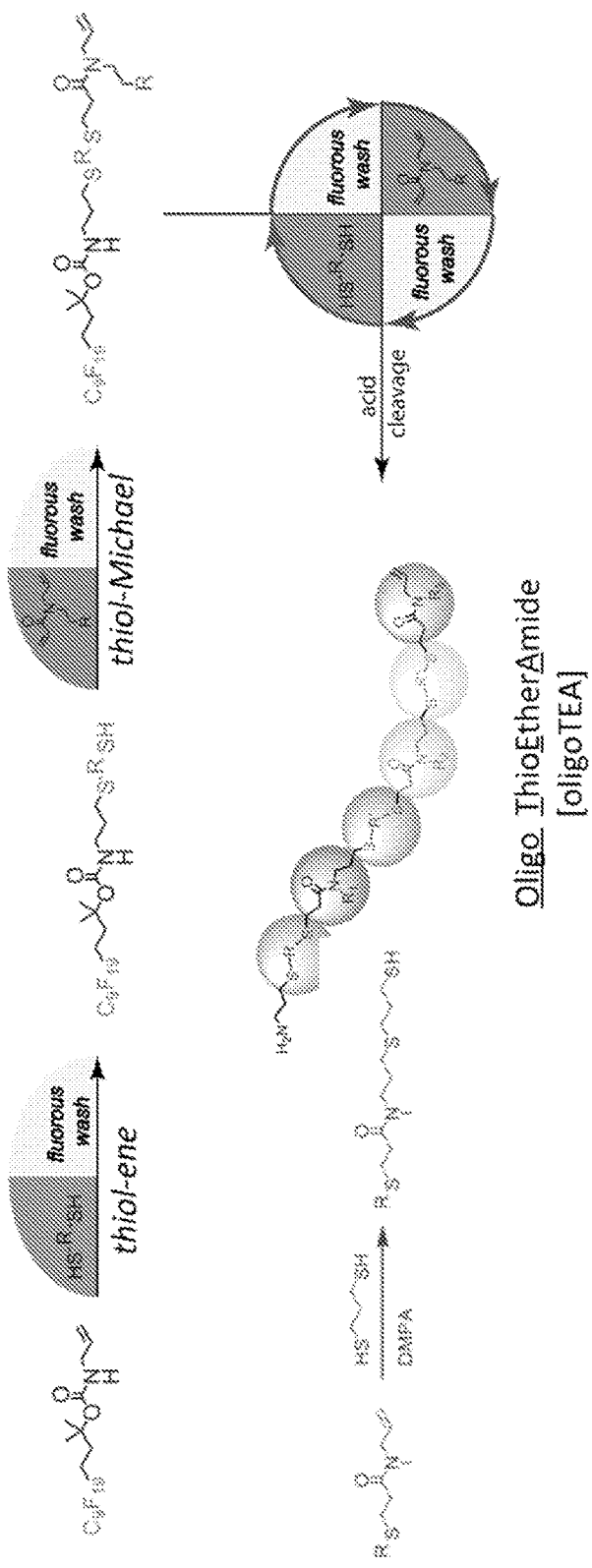
FIG. 2 shows a schematic of oligoTEA assembly process.
Figure 3:
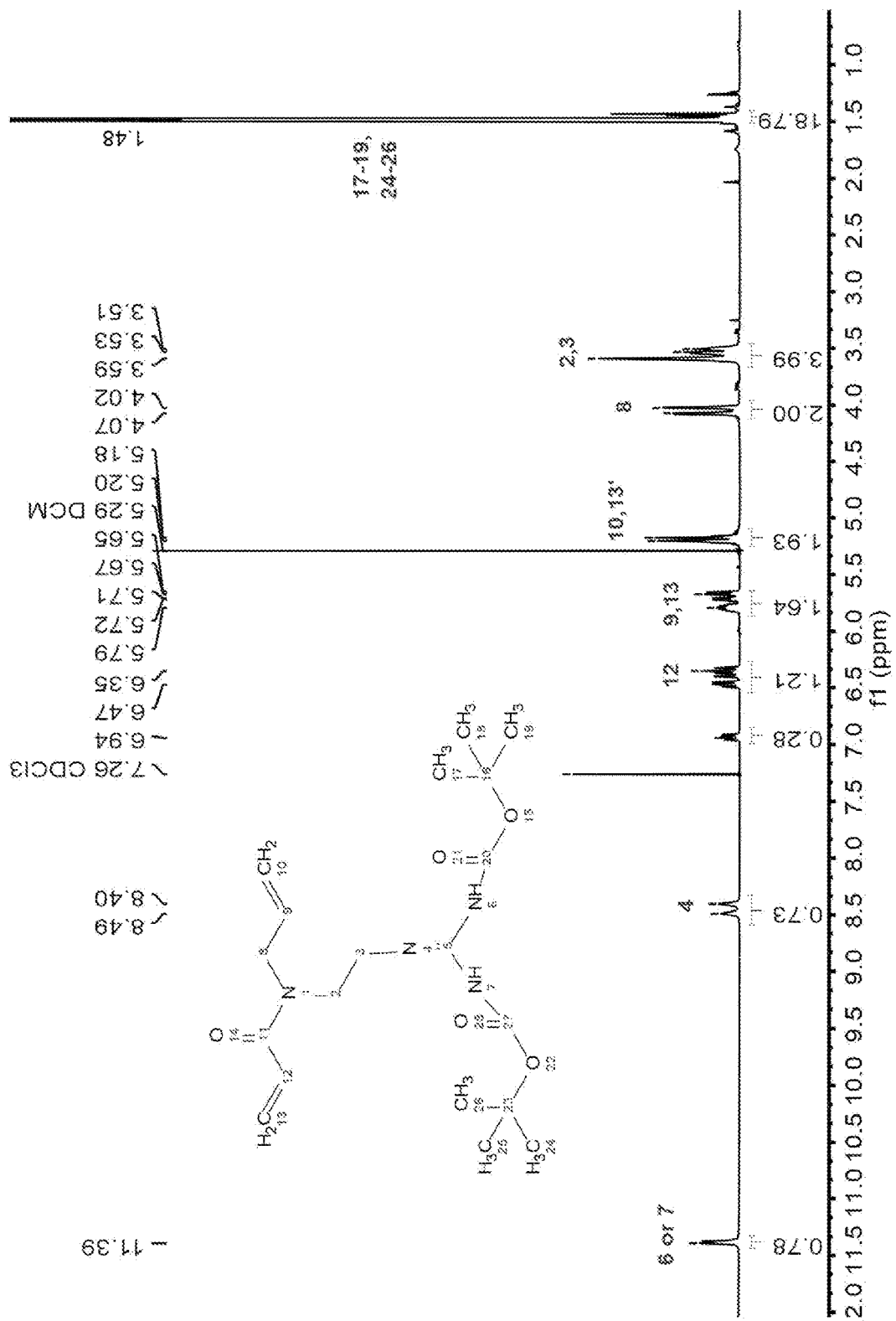
FIG. 3 shows an $^1$H NMR spectrum of the pure Boc-protected guanidine monomer, taken in $CDCl_3$ on a 600 MHz NMR spectrometer.

A compound of the present disclosure may be synthesized by chemical reaction of a dithiol and a monomer (e.g., cationic monomer, such as, for example, a Boc-protected guanidine monomer, such as in FIG. 1) through alternating thiol-ene and thiol-Michael addition reactions. FIG. 2 depicts an example of a compound of the present disclosure is synthesized.

In an example, synthesis of a compound of the present disclosure utilizes a liquid phase reaction support (e.g., fluorous solid-phase extraction (FSPE)). For example, the synthesis comprises the following steps:

i) a first reaction mixture is formed with a fluorous olefin (e.g., an olefin having a fluorous tag attached (e.g., covalently bonded) via a functional group that can be cleaved (e.g., a carbamate), such as, for example,

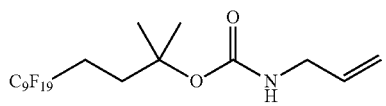

and the like), a dithiol (e.g., a dithiol of the present disclosure), a radical initiator (2,2-dimethoxy-2-phenylacetophenone (DMPA)), and a solvent (e.g., methanol);

ii) the reaction mixture is irradiated with light (e.g., UV-light) such that a reaction (e.g., a thiol-ene reaction) occurs forming a first reaction product;

iii) the first reaction mixture is purified via FSPE (e.g., the reaction mixture is loaded into a pre-packed fluorous solid-phase extraction cartridge and is washed with a first eluant (e.g., 20% water in methanol) to elute non-fluorous material (e.g., excess dithiol and DMPA) and then washed with a second eluant (e.g., neat methanol) to elute fluorous materials (e.g., the first reaction product);

iv) a second reaction mixture is formed with the first reaction product, a monomer (e.g., a cationic monomer, such as, for example a Boc-protected guanidine monomer, such as in FIG. 1), a phosphine (e.g., dimethylphenylphosphine) or a base (e.g., an amine base, such as, for example, a tertiary amine base and the like), and a solvent (e.g., methanol);

v) the reaction mixture is given time to stand such that a reaction (e.g., thiol-Michael reaction) occurs forming a second reaction product;

vi) the second reaction mixture is purified via FSPE (e.g., the reaction mixture is loaded into a pre-packed fluorous solid-phase extraction cartridge and is washed with a first eluant (e.g., 20% water in methanol) to elute non-fluorous material (e.g., excess monomer and phosphine) and then washed with a second eluant (e.g., neat methanol) to elute fluorous materials (e.g., the second reaction product);

vii) the steps are repeated until the desired number of dithiols and monomers are attached;

viii) the fluorous tag is cleaved (e.g., cleaved via addition of a mixture of trifluoroacetic acid (TFA) and dichloromethane (DCM)) from the resulting compound; and ix) the resulting compound is cleaved by methods known in the art (e.g., high performance liquid chromatography (HPLC)).

In an aspect, the present disclosure provides compositions comprising at least one compound of the present disclosure. Non-limiting examples of compositions include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents, include, but are not limited to distilled water for injection, physiological saline, vegetable oil, alcohol, and a combination thereof. Further, the injections may contain stabilizers, solubilizers, suspending agents, emulsifiers, soothing agents, buffers, preservatives, etc. The injections may be sterilized in the final formulation step or prepared by sterile procedure. The composition of the disclosure may also be formulated into a sterile solid preparation, for example, by freeze-drying, and can be used after sterilized or dissolved in sterile injectable water or other sterile diluent(s) immediately before use.

The compositions may include one or more pharmaceutically acceptable carrier. Pharmaceutically-acceptable carriers include, but are not limited to, sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Additional non-limiting examples of pharmaceutically acceptable carriers can be found in: *Remington: The Science and Practice of Pharmacy* (2005) 21st Edition, Philadelphia, PA Lippincott Williams & Wilkins.

In an aspect, the disclosure further provides kits.

In an example, a kit comprises pharmaceutical preparations containing any one or any combination of compounds of the present disclosure.

In an example, the kit comprises a package (e.g., a closed or sealed package) that contains a pharmaceutical preparation, such as, for example, one or more closed or sealed vials, bottles, blister (bubble) packs, or any other suitable packaging for the sale, distribution, or use of the pharmaceutical compounds and compositions comprising them.

In an example, the printed material includes printed information. The printed information may be provided on a label, or on a paper insert, or printed on the packaging material itself. The printed information may include information that, for example, identifies the composition in the package, the amounts and types of other active and/or inactive ingredients, and instructions for taking the composition, such as, for example, the number of doses to take over a given period of time, and/or information directed to a pharmacist and/or another health care provider, such as a physician, or a patient. The printed material may include, for example, an indication that the pharmaceutical composition and/or any other agent provided with it is for treatment of a subject having a bacterial infection. In an example, the product includes a label describing the contents of the container and providing indications and/or instructions regarding use of the contents of the container to treat a subject having any bacterial infection.

In an example, one or more compound and/or one or more composition comprising one or more compound described herein is administered to a subject in need of treatment using any known method and route, including, but not limited to, oral, parenteral, subcutaneous, intraperitoneal, intrapulmonary, intranasal and intracranial injections. Parenteral infusions include, but are not limited to intramuscular, intravenous, intraarterial, intraperitoneal, and subcutaneous administration. Topical and/or transdermal administrations are also encompassed.

In an aspect, the present disclosure provides methods involving compounds of the present disclosure. Methods of the present disclosure may involve administering a compound of the present disclosure to a subject in need of treatment who has been diagnosed with or is suspected of having a bacterial infection (i.e., therapeutic use). A method can be carried out in a subject in need of prophylaxis for bacterial infections/illnesses.

A subject in need of treatment may be a human or non-human mammal. Non-limiting examples of non-human mammals include cows, pigs, mice, rats, rabbits, cats, dogs, or other agricultural, pet, or service animals, and the like.

In an example, the bacterial infection can be caused by one or more gram-positive and/or gram-negative bacteria. Non-limiting examples of gram-positive bacteria include Methicillin-resistant *Staphylococcus aureus* (MRSA), *Staphylococcus epidermidis, Bacillus subtilis, Streptococcus, Enterococcus, Listeria monocytogenes, Clostridium difficile*, and the like, and combinations thereof. Non-limiting examples of gram-negative bacteria include *Pseudomonas aeruginosa, Escherichia coli, Klebsiella pneumonia, Vibrio cholera, Acinetobacter baumannii*, and the like, and combinations thereof.

In an example, compounds of the present disclosure show toxicity against *B. subtilis* at a compound (e.g., BDT-3G, PDT-4G, BDT-4G, BDT-4Am, BDT-5G) concentration of equal to or less than 10 M.

In an example, compounds of the present disclosure show toxicity against *E. coli* at a compound (e.g., BDT-3G, PDT-4G, BDT-4G, BDT-5G) concentration of equal to or less than 10 µM.

In an example, compounds of the present disclosure show toxicity against MRSA (cell line 33591) at a compound (e.g., BDT-3G, PDT-4G, BDT-4G) concentration of equal to or less than 10 M.

In an example, compounds of the present disclosure (e.g., PDT-4G and BDT-4A) are not hemolytic (e.g., cell viability is 50% or greater) at concentrations of less than or equal to 40 M.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

In general, the present disclosure provides a system and method for oligothioetheramides (oligoTEAs) as antimicrobial and antibacterial agents In the following Statements, various examples of the compounds, compositions, and methods of using the compounds and compositions of the present disclosure are described:

Statement 1. A compound having the following structure:

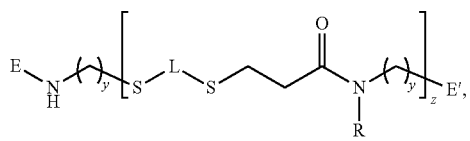

where z is 2-7, including all integer values and ranges therebetween (e.g., 2, 3, 4, 5, 6, 7); y independently at each occurrence is 2-10, including all integer values and ranges therebetween (e.g., 2, 3, 4, 5, 6, 7, 8, 9, 10); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

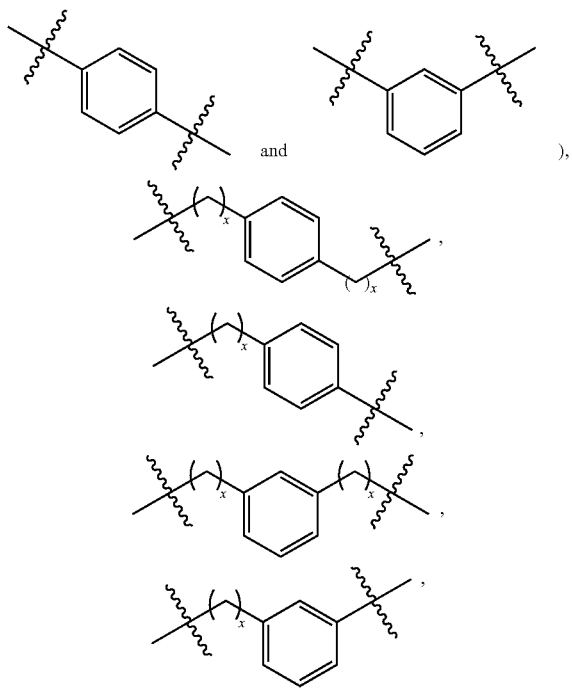

and the like, where x is 1-10, including all integer values and ranges therebetween (e.g., 1, 2, 3, 4, 5, 6, 7, 8, 9, 10)); E is a first end group chosen from H, a polymeric group (e.g., a hydrophilic polymeric group, such as, for example, derivative of a polyethylene glycol (PEG) group, derivative of a poly(vinyl alcohol) group, derivative of a poly(N-vinyl pyrrolidone) group, derivative of a poly(2-oxazoline) group, and the like, or a zwitterionic polymeric group, such as, for example, derivative of a polysulfobetaine group, derivative of a polycarboxybetaine group, derivative of a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and

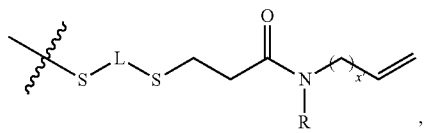

where x' is 0-6, including all integer values and ranges therebetween (e.g., 0, 1, 2, 3, 4, 5, 6), where the compound has at least two cationic groups that are the same or different (e.g., two cationic groups comprising guanidinium groups).
Statement 2. The compounding according to Statement 1, where the compound has the following structure:

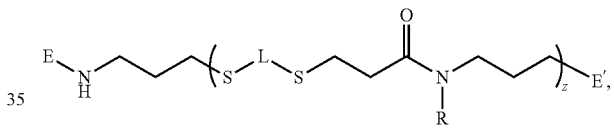

wherein z is 2-7 (e.g., 2, 3, 4, 5, 6, 7); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

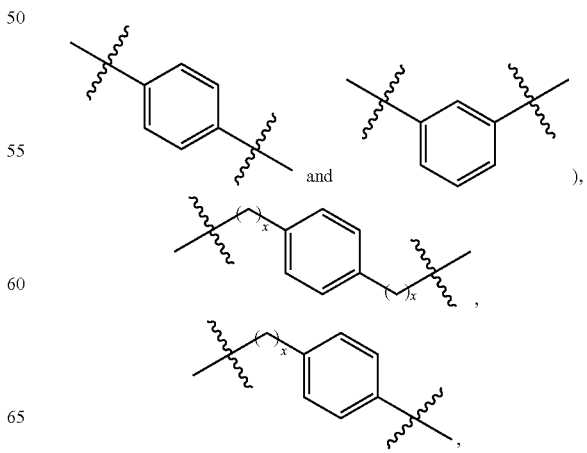

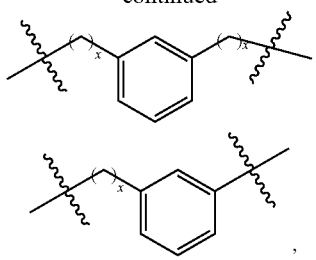

and the like, where x is 1-10, including all integer values and ranges therebetween (e.g., 1, 2, 3, 4, 5, 6, 7, 8, 9, 10)); E is a first end group chosen from H, a polymeric group (e.g., a hydrophilic polymeric group, such as, for example, a poly-ethylene glycol (PEG) group, a poly(vinyl alcohol) group, a poly(N-vinyl pyrrolidone) group, a poly(2-oxazoline) group, where x' is 0-6, including all integer values and ranges therebetween (e.g., 0, 1, 2, 3, 4, 5, 6), where compound has at least two cationic groups (e.g., two cationic groups comprising guanidinium groups).

Statement 3. The compound according to Statement 1 or Statement 2, where the compound has the following structure:

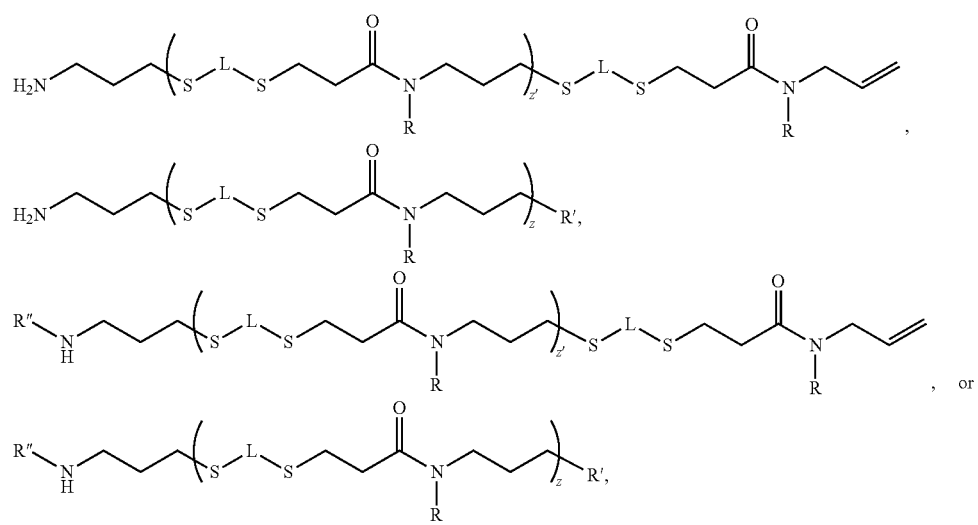

and the like, or a zwitterionic polymeric group, such as, for example, a polysulfobetaine group, a polycarboxybetaine group, a polyphosphorylcholine group, and the like), peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), and a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and E' is a second end group chosen from R', where R' is chosen from hydrogen, a cationic group, a linear or branched aliphatic group (e.g., a linear or branched alkyl group), aromatic group, and a heterocyclic group, and where z independently at each occurrence is 2-7, including all integer values and ranges therebetween (e.g., 2, 3, 4, 5, 6, 7); z' independently at each occurrence is 1-7, including all integer values and ranges therebetween (e.g., 1, 2, 3, 4, 5, 6, 7); R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene(e.g.,

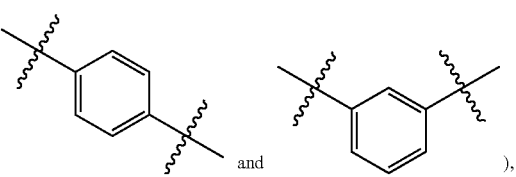

),

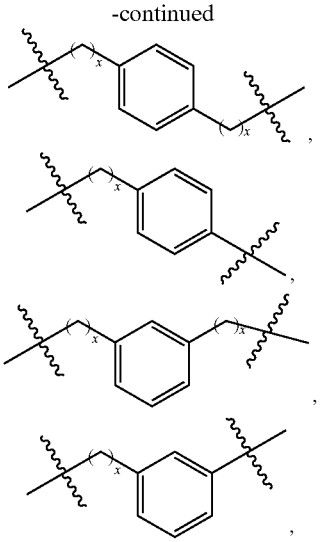

and the like, where x is 1-10, including all integer values and ranges therebetween (e.g., 1, 2, 3, 4, 5, 6, 7, 8, 9, 10)); R' is chosen from hydrogen, a cationic group, a linear or branched aliphatic group (e.g., a linear or branched alkyl group), aromatic group, and a heterocyclic group, and

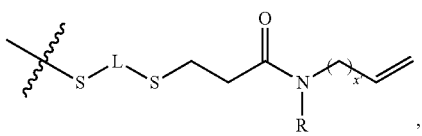

where x' is 0-6, including all integer values and ranges therebetween (e.g., 0, 1, 2, 3, 4, 5, 6); R" is a polymeric group (e.g., a hydrophilic polymeric group, such as, for example, a polyethylene glycol (PEG) group, a poly(vinyl alcohol) group, a poly(N-vinyl pyrrolidone) group, a poly (2-oxazoline) group, and the like, or a zwitterionic polymeric group, such as, for example, a polysulfobetaine group, a polycarboxybetaine group, a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like) or a polymeric group attached (e.g., covalently bonded) to a cleavable moiety (e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); where the compound has at least two cationic groups that are the same or different (e.g., two cationic groups comprise guanidinium groups (e.g.,

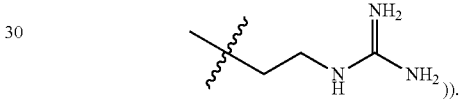

Statement 4. The compound according to any one of the preceding Statements, where the compound has the following structure:

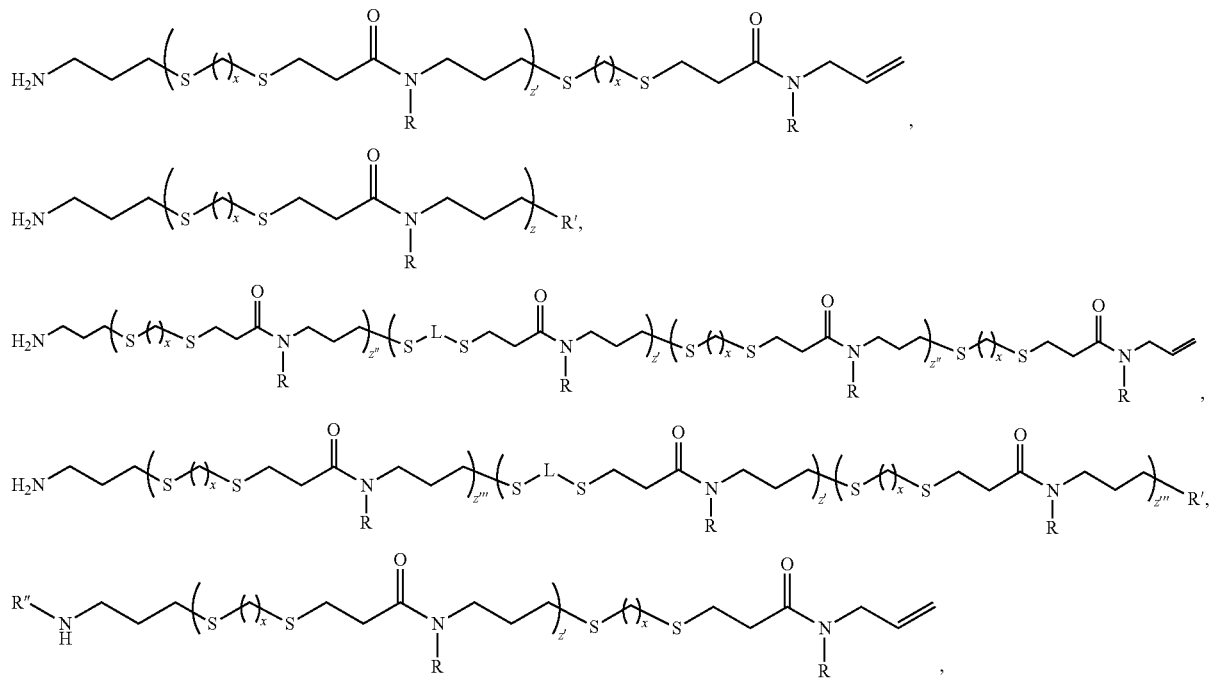

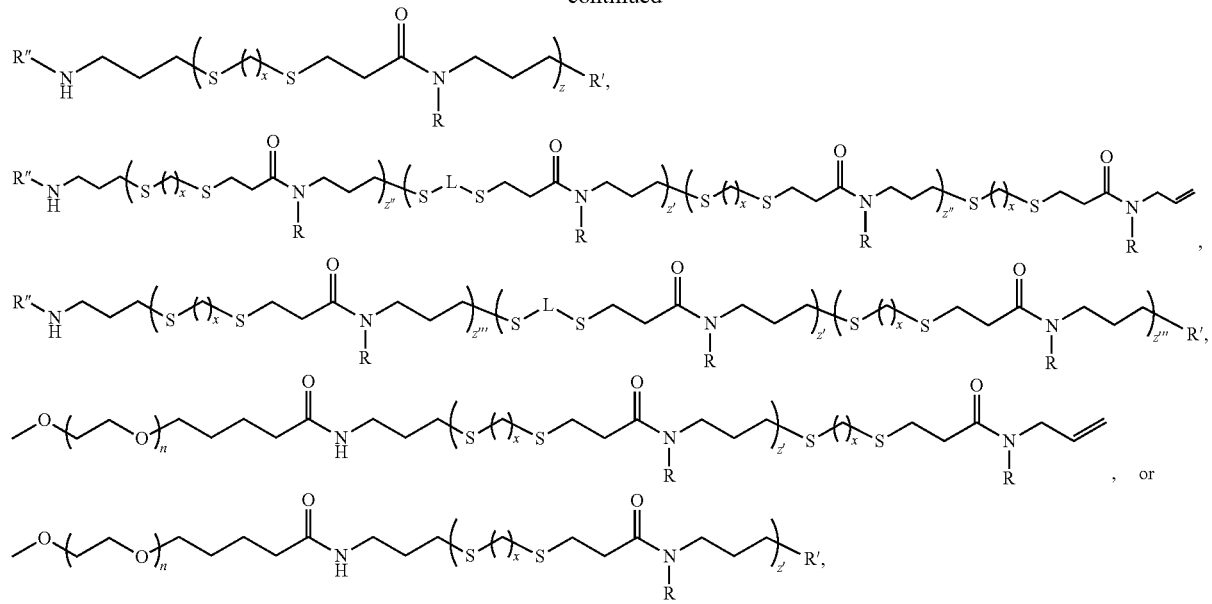

where x independently at each occurrence is 2-10, including all integer values and ranges therebetween (e.g., 2, 3, 4, 5, 6, 7, 8, 9, 10); z independently at each occurrence is 2-7, including all integer values and ranges therebetween (e.g., 2, 3, 4, 5, 6, 7); z' independently at each occurrence is 1-7, including all integer values and ranges therebetween (e.g., 1, 2, 3, 4, 5, 6, 7); z" and z'" independently at each occurrence is 0-7, including all integer values and ranges therebetween (e.g., 0, 1, 2, 3, 4, 5, 6, 7), where the sum of z' and z'" is 2 or more; R independently at each occurrence is chosen from cationic groups, linear or branched aliphatic groups (e.g., linear or branched alkyl groups), aromatic groups, and heterocyclic groups; L independently at each occurrence is a linking moiety chosen from aliphatic moieties (e.g., alkylene moieties; such as, for example, methylene, ethylene, propylene, butylene, and the like (e.g., an alkylene moiety having 1-10 carbons, including all integer values and ranges therebetween (e.g., 1, 2, 3, 4, 5, 6, 7, 8, 9, 10)); alkenylene moieties; and alkynylene moieties), aromatic moieties (e.g., phenylene (e.g.,

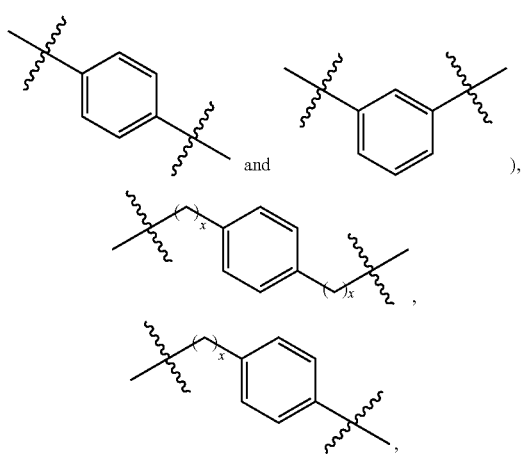

and the like, where x is 1-10, including all integer values and ranges therebetween (e.g., 1, 2, 3, 4, 5, 6, 7, 8, 9, 10)); R' is chosen from hydrogen, a cationic group, a linear or branched aliphatic group (e.g., a linear or branched alkyl group), aromatic group, and a heterocyclic group, and

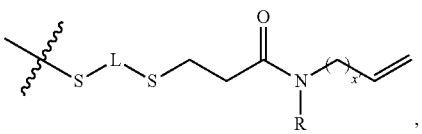

where x' is 0-6, including all integer values and ranges therebetween (e.g., 0, 1, 2, 3, 4, 5, 6); R" is a polymeric group (e.g., a hydrophilic polymeric group, such as, for example, a polyethylene glycol (PEG) group, a poly(vinyl alcohol) group, a poly(N-vinyl pyrrolidone) group, a poly (2-oxazoline) group, and the like, or a zwitterionic polymeric group, such as, for example, a polysulfobetaine group, a polycarboxybetaine group, a polyphosphorylcholine group, and the like), a peptide (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like) or a polymeric group attached (e.g., covalently bonded) to a cleavable moiety

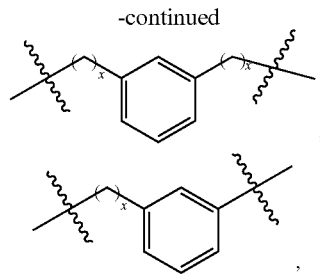

(e.g., a cleavable peptide, such as, for example, a peptide cleavable by a protease (e.g., a tripeptide of glycine-glycine-glycine; a dipeptide of leucine-leucine; a 5mer of leucine-proline-Xaa-threonine-glycine, where Xaa is any amino acid (e.g., Xaa is methionine); a dipeptide of Xaa-leucine; a dipeptide of glutamic acid-arginine; a dipeptide of glutamic acid-valine, and the like), such as, for example, a bacterial protease, such as, for example, Sortase A, aureolysin, glutamyl endopeptidase I, and/or the like); and where the compound has at least two cationic groups that are the same or different (e.g., two cationic groups comprise guanidinium groups (e.g.,

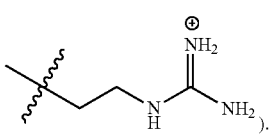).

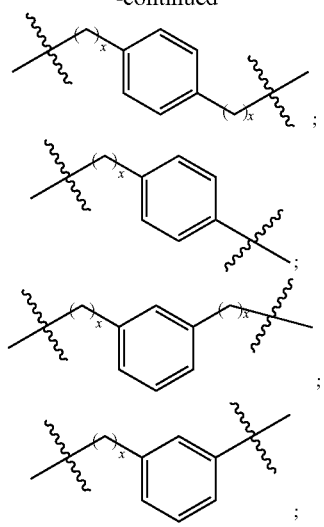

and the like, where x is 1-10, including all integer values and ranges therebetween (e.g., 1, 2, 3, 4, 5, 6, 7, 8, 9, and 10), and the like.

Statement 7. The compound according to any one of the preceding Statements, where the cationic group has the following structure:

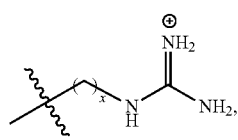

where x is 1, 2, 3, 4, 5, or 6 (e.g., x is 2).

Statement 5. The compound according to any one of the preceding Statements, where the cationic group is chosen from aliphatic (e.g., alkyl) guanidinium groups, aliphatic ammonium groups (e.g., protonated primary, secondary, or tertiary amines), aliphatic quaternary amine groups, aliphatic phosphonium groups, aliphatic sulfonium groups, aliphatic imidazolium groups, aliphatic thiazolium groups, aliphatic pyrazolium groups, and the like.

Statement 6. The compound according to any one of the preceding Statements, where L is chosen from alkylene moieties, such as, for example, methylene, ethylene, propylene, butylene, and the like; alkenylene moieties; and alkynylene moieties), aromatic moieties (e.g., phenylene, such as, for example

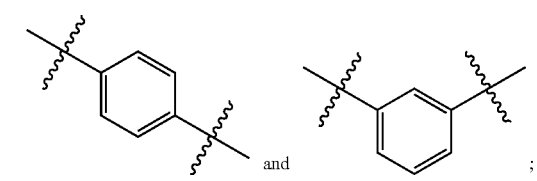

Statement 8. The compound according to any one of the preceding Statements, where E, E', R', and/or R" are cleavable (e.g., cleavable by a trigger, such as, for example, a protease (e.g., a bacterial protease, such as, for example, Sortase A, aureolysin, and glutamyl endopeptidase I)).

Statement 9. The compound according to any one of the preceding Statements, where the compound has the following structure:

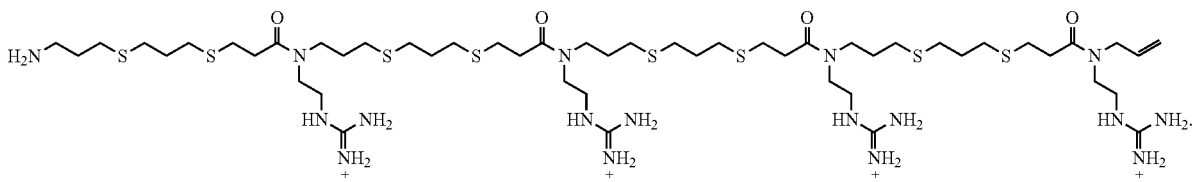 [SMILES: C=CCN(CCNC(=N)N)C(=O)CCSCCCSCCCN(CCNC(=N)N)C(=O)CCSCCCSCCCN(CCNC(=N)N)C(=O)CCSCCCSCCCN(CCNC(=N)N)C(=O)CCSCCCSCCCN]

Statement 10. The compound according to any one of the preceding Statements, where the compound has the following structure:
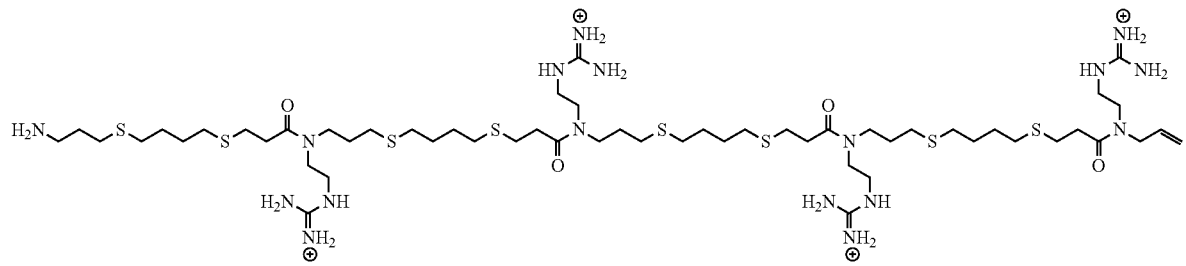 [SMILES: C=CCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN]
Statement 11. The compound according to any one of the preceding Statements, where the compound has the following structure:
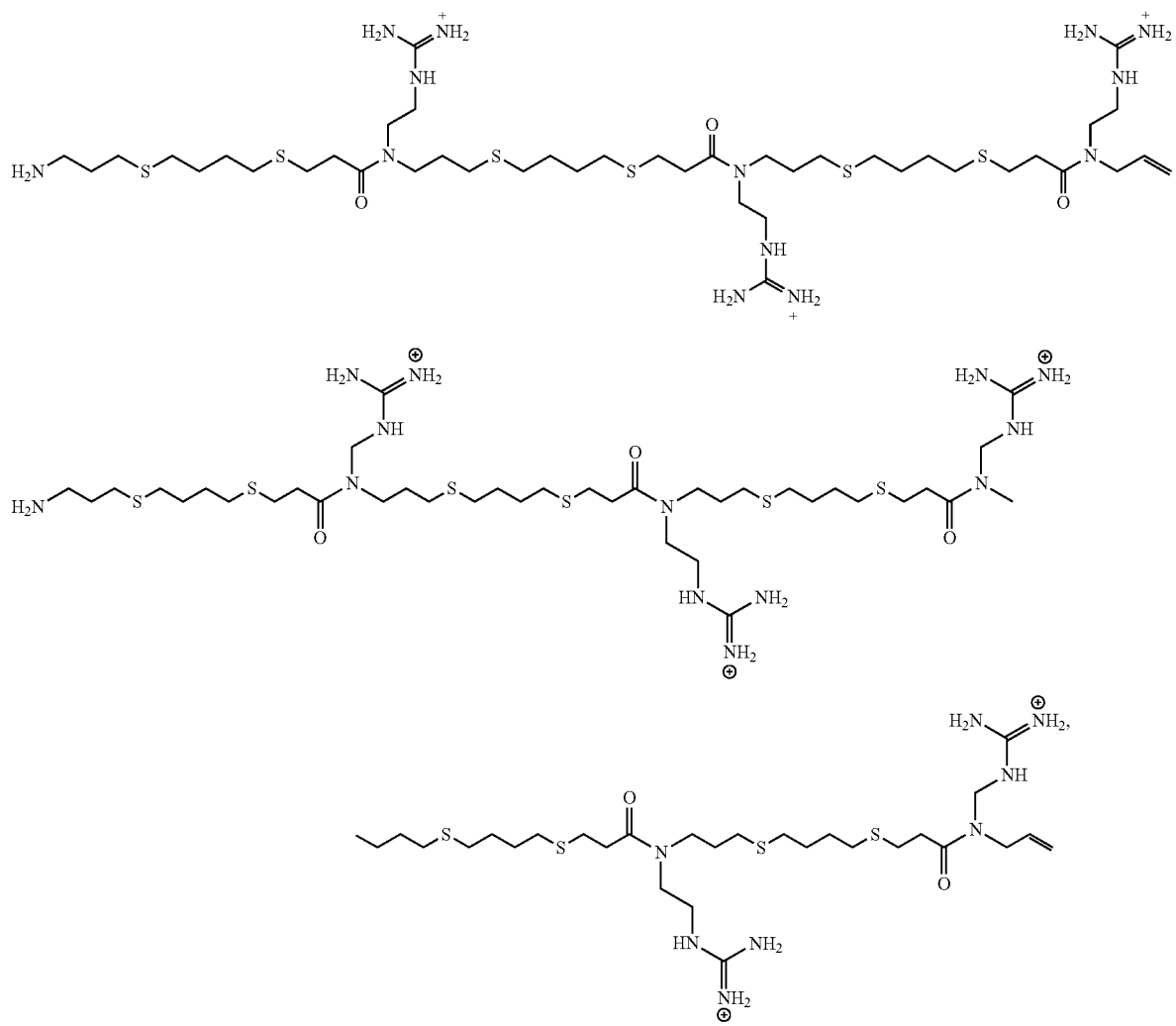

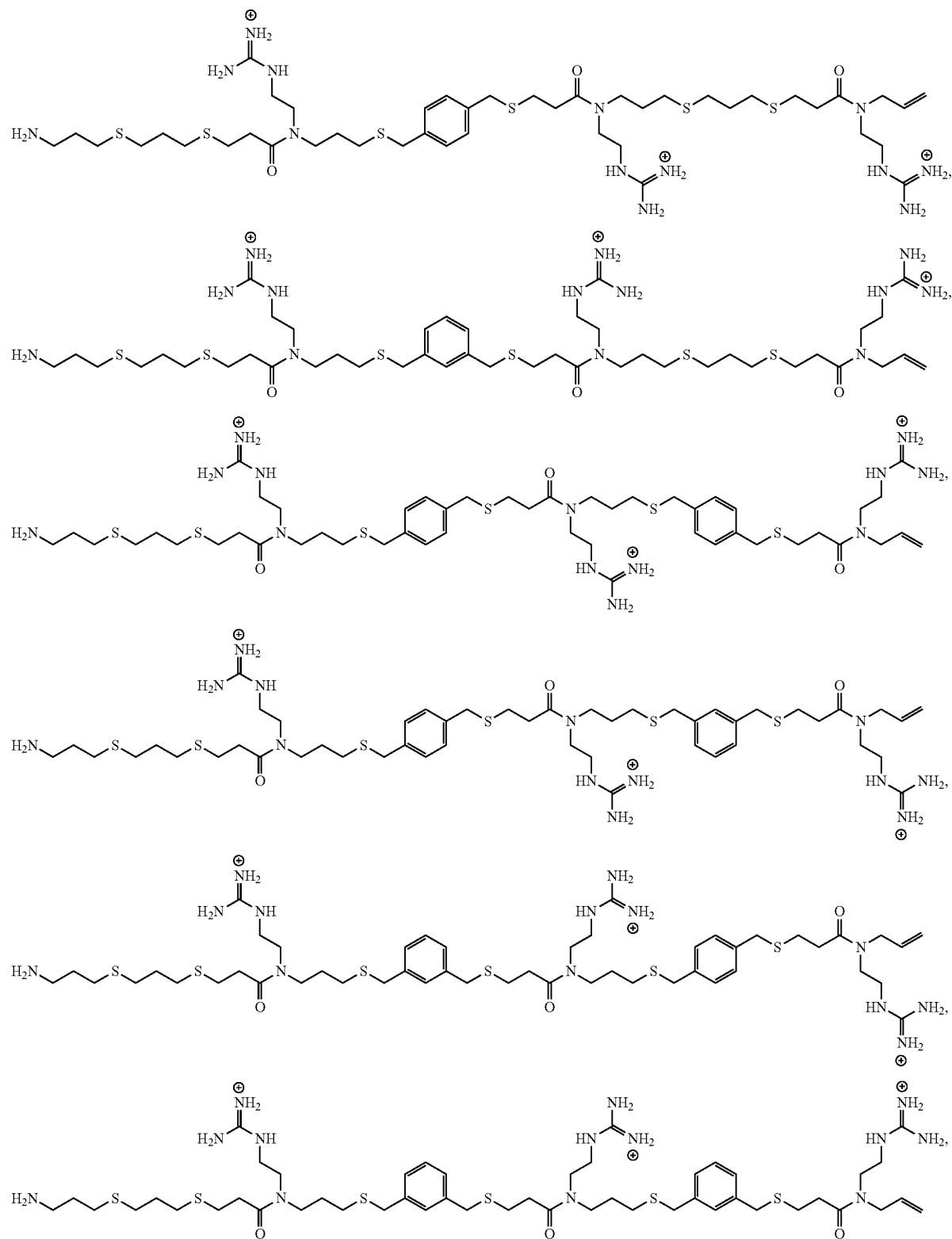

-continued

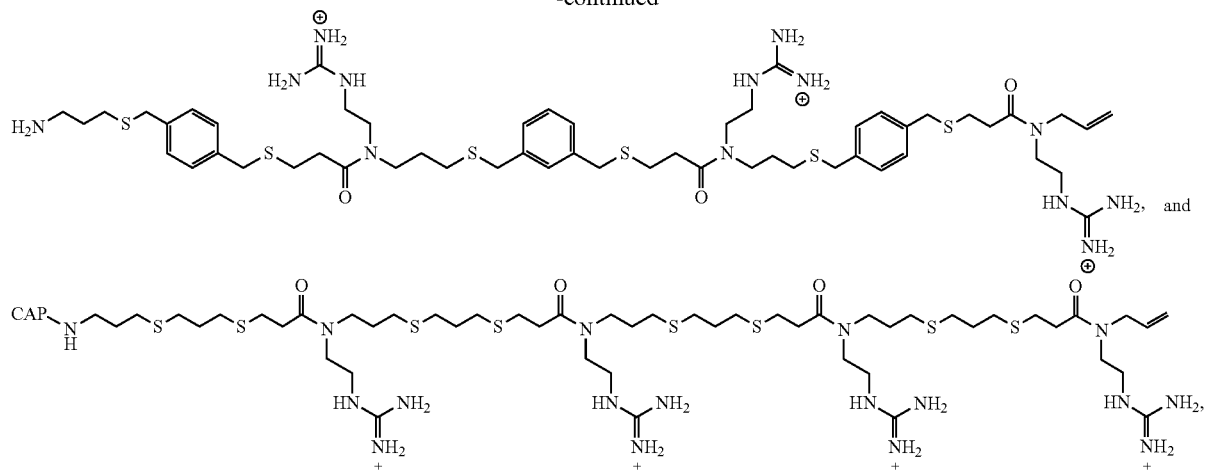

where CAP is

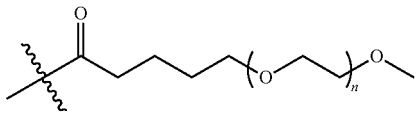

and is 1-50, including all integer values and ranges therebetween.

Statement 12. A composition comprising one or more compound of any one of the preceding Statements and a pharmaceutically acceptable carrier.

Statement 13. The composition according to Statement 12, where the one or more compound has the following structure:

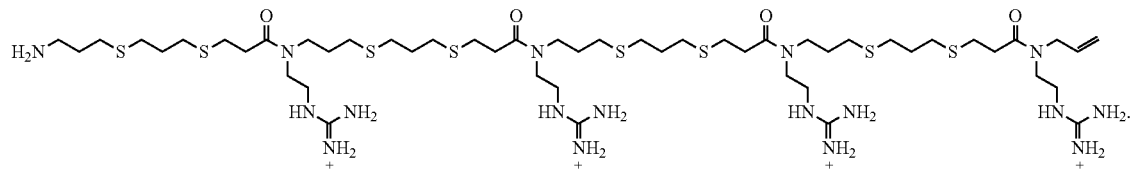 [SMILES: C=CCN(CCNC(=N)N)C(=O)CCSCCCSCCCN(CCNC(=N)N)C(=O)CCSCCCSCCCN(CCNC(=N)N)C(=O)CCSCCCSCCCN(CCNC(=N)N)C(=O)CCSCCCSCCCN]

Statement 14: The composition according to Statement 12, where the one or more compound has the following structure:

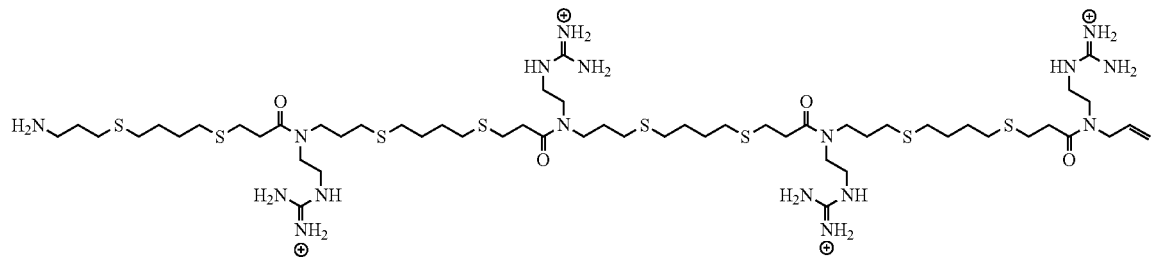 [SMILES: C=CCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN]

Statement 15. The composition according to Statement 12, where the compound is chosen from:

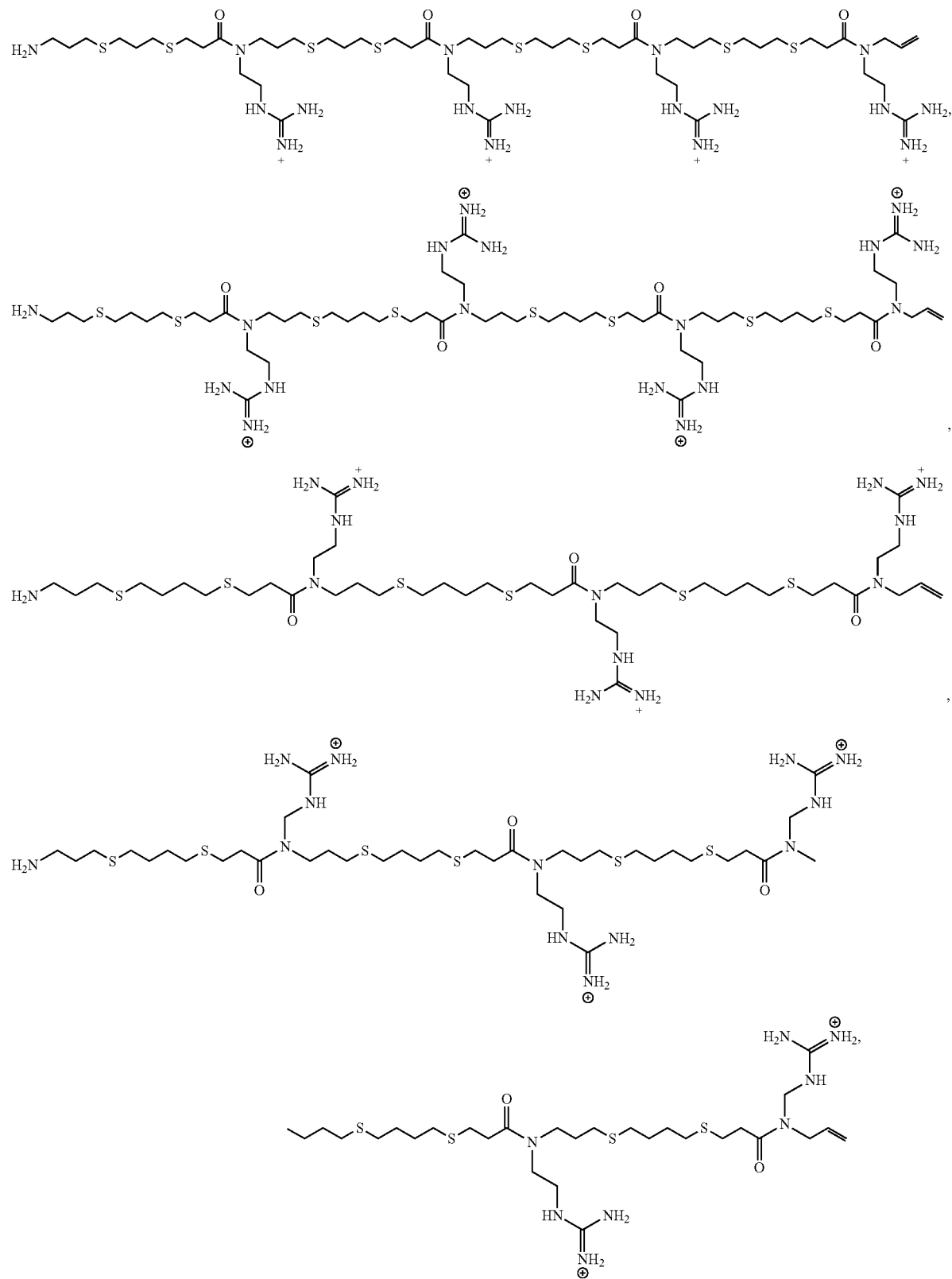

-continued
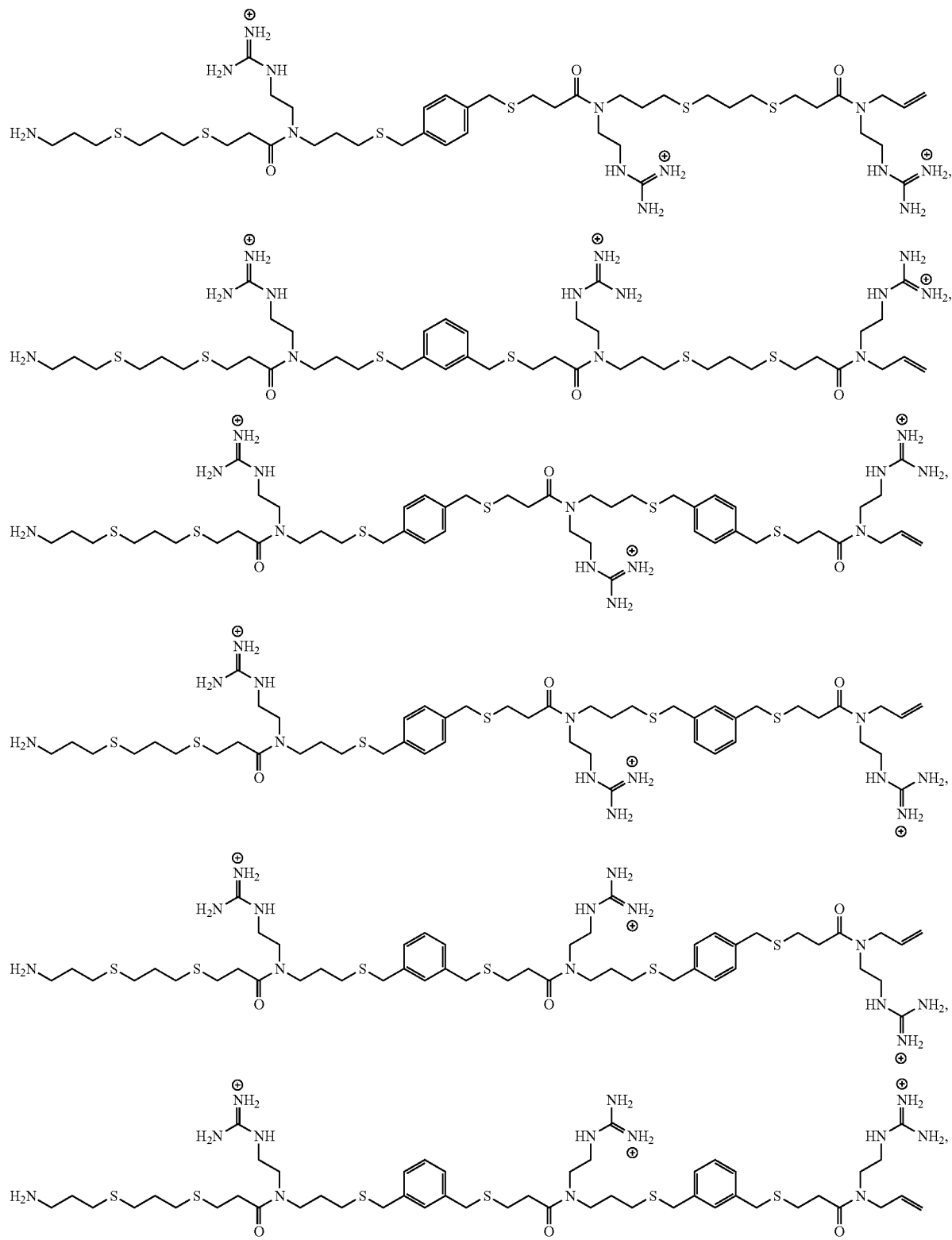

-continued

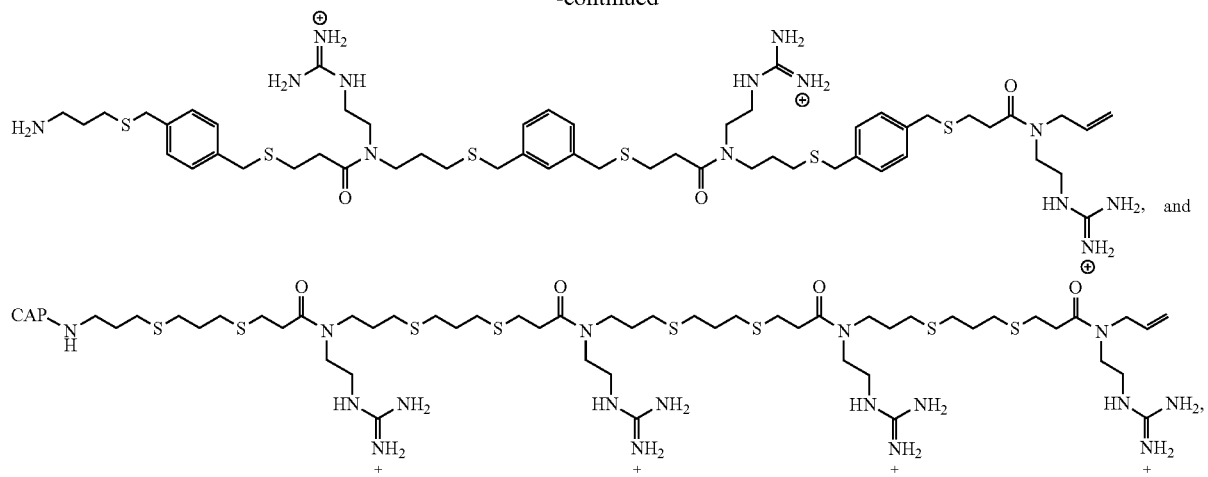

where CAP is

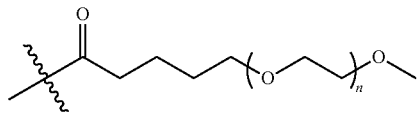

and n is 1-250, including all integer values and ranges therebetween, and combinations thereof.

Statement 16. A method of treating a subject in need of treatment with one or more compounds according to any one of Statements 1-11 and/or a composition according to any one of Statements 12-15, comprising administering to the subject in need of treatment one or more compounds according to any one of Statements 1-11 and/or a composition according to any one Statements 13-15.

Statement 17. The method according to Statement 16, where the subject in need of treatment has a bacterial infection and/or prophylaxis therefrom.

Statement 18. The method according to Statement 16 or Statement 17, where the bacterial infection is caused by one or more gram-positive bacteria.

Statement 19. The method according to any one of Statements 16-18, where the bacterial infection is caused by one or more gram-positive and one or more gram-negative bacteria. Statement 20. The method according to any one of Statements 16-19, where one or more gram-positive bacteria is Methicillin-resistant *Staphylococcus aureus* (MRSA), *Staphylococcus epidermidis, Bacillus subtilis, Streptococcus, Enterococcus, Listeria monocytogenes, Clostridium difficile*, or a combination thereof.

Statement 21. The method according to any one of Statements 16, 17, or 19, where the one or more gram-negative bacteria is *Pseudomonas aeruginosa, Escherichia coli, Klebsiella pneumonia, Vibrio cholera, Acinetobacter baumannii*, or a combination thereof.

The following examples are presented to illustrate the present disclosure. They are not intended to limiting in any matter.

Example 1

This example describes the synthesis, characterization, and use of compounds (e.g., oligoTEAs) of the present disclosure.

This example describes a new class of sequence-defined synthetic oligomers called oligothioetheramides (oligoTEAs) based on the sequential addition of N-allylacrylamides to symmetric dithiols. The versatility of this assembly process facilitated the design and synthesis of oligoTEAs with a wide variety of sequences and compositions. The synthesis of linear amine-based antibacterial and antimicrobial oligoTEAs (AOTs) is described and the relationship between AOT composition, sequence and their ability to lyse pathogenic and non-pathogenic bacteria strains was evaluated. By tuning the overall charge (pendant group modification) and hydrophobicity (backbone modifications), non-cytotoxic AOTs with potent antibacterial and antimicrobial activity in the presence of serum were created. It was demonstrated that AOTs lysed cells via membrane permeabilization and that both hydrophobicity and macromolecular conformation are important properties that regulate AOT activity. Taken together, these data highlight the utility of AOTs as potent clinical antibacterial and antimicrobial candidates.

As described herein, AOTs can be assembled with the desired combination of cationic and backbone hydrophobic groups to facilitate promising antibacterial activity. The collective data in this example indicate hydrophobicity and conformation, driven by composition and sequence, have a significant effect on antibacterial activity. These data also shows AOT-induced bacterial death occurs via membrane permeabilization. The correlations between AOT hydrophobicity, potency (MIC), cell death rate and extent of membrane disruption, underscore the importance of sequence control as it pertains to attaining the optimal composition and conformation necessary for the design of potent and selective AOTs.

Synthesis of oligoTEAs of the present disclosure was conducted as follows. Compound 2-(2-aminoethyl)-1,3-di-BOC-guanidine (see FIG. 1) and 1.2 equivalents of triethylamine were dissolved in CH$_2$Cl$_2$. The reaction mixture was cooled to 0° C., while being stirred. 1.1 equivalents of acryloyl chloride (diluted in CH$_2$Cl$_2$) was added drop wise to the reaction mixture over a period of 1 hour at 0° C. The reaction mixture was stirred at 0° C. for 1 hour (h or hr) and at room temperature for 1 hour. The reaction mixture was washed twice with water and once with brine solution. The organic layer was then dried over anhydrous Na$_2$SO$_4$, filtered, and concentrated at reduced pressure. The reaction mixture containing the secondary amine was used without purification for the next step.

The reaction mixture (dissolved in anhydrous DMF) was added to 4 equivalents of NaH (60% dispersion in mineral oil) in anhydrous DMF. The mixture was stirred for 15 minutes (min) at room temperature. Then, 2 equivalents of allyl bromide was added dropwise into the mixture over a period of 30 min at room temperature and stirred for 30 min at room temperature. The reaction was quenched with water and extracted with diethyl ether. The combined organic layers were washed with brine solution and dried over anhydrous $Na_2SO_4$. The crude product was purified by silica gel column chromatography. The product was eluted with 23% ethyl acetate in hexane. Purity was confirmed by $^1H$ NMR.

OligoTEAs Synthesis and Purification: Thiol-ene reaction: Five equivalents of 1,4-butanedithiol (BDT), or 1,3-propanedithiol (PDT), and 2,2-dimethoxy-2-phenylacetophenone (DMPA, 5 mol % of dithiol) were added to a solution of corresponding fluorous-olefin (100 mM) in methanol. The reaction mixture was subjected to UV irradiation for 270 s at 20 mW/cm$^2$. The product (fluorous-thiol) was purified by FSPE.

Thiol-Michael addition: Two equivalents of corresponding monomer and dimethyl phenyl phosphine (Me$_2$PhP, 5 mol % of monomer) were added to the fluorous-thiol (100 mM) in methanol eluted from the purification of last thiol-ene reaction. Methanol was removed by reduced pressure in 1-1.5 hours. The time required for the evaporation of methanol was enough for the quantitative conversion of Michael addition. The reaction mixture was then purified by FSPE.

Fluorous solid-phase extraction (FSPE): The fluorous organic mixture was loaded onto a 1 g pre-packed fluorous solid-phase extraction (FSPE) cartridge. A fluorophobic wash (4:1 methanol:water) was used to elute all the non-fluorous molecules whereas the fluorous molecules were retained on the fluorous silica gel. A fluorophilic wash with methanol was then used to elute the fluorous molecules from the fluorous stationary phase.

Cleavage reaction: The fluorous carbamate protected oligomer was dissolved in 1:1 trifluoroacetic acid:dichloromethane ([oligomer]=5 mM) and stirred for 3 hours at room temperature. The reaction mixture was then dried under Nitrogen for 10 min, dissolved in methanol, and purified via reverse-phase High Performance Liquid Chromatography (HPLC).

HPLC purification: OligoTEAs were purified on a 1100 Series Agilent HPLC system equipped with a UV diode array detector and a 1100 Infinity analytical scale fraction collector using reverse phase C18 column. The column compartment was kept at 25° C. during fractionation. Solvents for HPLC were water with 0.1% trifluoroacetic acid (solvent A) and acetonitrile with 0.1% trifluoroacetic acid (solvent B). OligoTEAs were collected based on their absorption at 230 nm. The fractionated oligoTEA was transferred to a vial, dried, confirmed by LC-MS, and stored under Argon until further analysis.

Biological Assays: Minimum inhibitory concentration (MIC) assay: A single bacterial colony (*Bacillus subtilis* (*B. subtilis*) or methicillin-resistant *Staphylococcus aureus* (MRSA)) was selected and incubated in media (Luria Broth (LB) for *B. subtilis* or Tryptic Soy Broth (TSB) for MRSA) at 37° C. overnight. This was sub-cultured in media and incubated at 37° C. until the $OD_{600}$ was approximately 0.5 (2.5-3.5-hour incubation). The subculture was diluted with media to an $OD_{600}$ of 0.001. Diluted subculture and 1 mM stocks of compounds to be tested were added to a clear 96-well plate, and serially diluted by a factor of 0.5. The well plate was incubated overnight and the absorbance was measured at 600 nm using the TECAN. To determine the MIC in presence of serum, assays were repeated using media with 20% heat-inactivated mouse serum or 20% fetal bovine serum. To determine the MIC in cation-adjusted media or cation-adjusted media with serum, 0.62 mM $CaCl_2 \cdot 2H_2O$ and 0.51 mM $MgCl_2 \cdot 6H_2O$ were added. The MIC50 was calculated using a 4PL sigmoidal nonlinear regression on Prism. The MIC100 was calculated as the first point below 10% of the maximum.

Membrane permeabilization propidium iodide (PI) assay: 1 mM BDT-4G stock solutions were prepared in DMSO. *B. subtilis* strains were streaked onto a Luria Broth (LB) agar plate and incubated overnight. One colony was selected and incubated in LB overnight, then subcultured and incubated until the $OD_{600}$ measured between 0.5 and 0.6. Bacteria were harvested, washed, and resuspended in a solution of 5 mM HEPES, 5 mM glucose, and 10 µM propidium iodide. 150 µL bacteria solution was added to each well of a black 96 well plate. Fluorescence measurements were taken at 535 nm excitation, 617 nm emission on a TECAN Infinite M1000 PRO Microplate reader (Männdorf) (TECAN) for 2 minutes. BDT-4G stock solution was added for a concentration of 15 µg/mL, and fluorescence measurements were taken for an additional 20 minutes.

Hemolysis (a.k.a., RBC) assay: Single donor human red blood cells were acquired from Innovative Research. A total of 200 µL of red blood cells was washed twice with 500 µL of 1×PBS at pH 7.4 by centrifugation (5 min at 500 g) and re-suspended in 5 mL of the same buffer for a 4% v/v RBC solution. OligoTEA solutions (diluted in PBS) or controls were mixed 1:1 with the RBC solution in a v-bottom, 96-well plate to reach a final volume of 100 µL. The resulting mixture was incubated on a shaker at 37° C. for 1 hour and then centrifuged (5 min at 2120 g) at 4° C. A total of 75 µL of supernatant was transferred to a new plate. Hemolysis was measured via absorbance of released hemoglobin at 540 nm on a TECAN Infinite M1000 PRO Microplate reader and normalized to 0.1% Triton-X (100%) or PBS buffer (0%). All experiments were performed in triplicates.

MTS cell proliferation assay: 15,000 of human embryonic kidney (HEK293) cells in 100 µL were plated in each well of a clear, 96-well plate and incubated at 37° C. overnight. Cells were then washed with 1×PBS and incubated with 100 µL of 5 to 40 µM of samples in media with phenol red at 37° C. for 1 or 24 hours. Each well was again washed with 1×PBS. 100 µL of clear media (without phenol red) and 10 µL of MTS solution (Promega) were added, and the plate was incubated for 1 hour. Absorbance measurements were taken at 490 nm on a TECAN Infinite M1000 PRO Microplate reader and normalized to untreated cells (100%) or clear media (0%). All experiments were performed in triplicates.

Synthetic design of AOTs. Demonstrated in FIG. 2 is the rapid and efficient synthetic method for the assembly of precise sequence-defined oligoTEAs with a tunable and flexible thioether backbone. This unique methodology utilizes reaction orthogonality and a soluble fluorous support to achieve precise sequence-control in the liquid-phase. The N-allylacrylamide monomer framework includes a reactive acrylamide group that can undergo phosphine-catalyzed Michael addition with thiols, the desired tert-Butyloxycarbonyl (Boc) protected amine pendant functional group, and a reactive allyl group that can undergo photo-initiated thiol-ene "click" addition with another thiol. Following the reaction of each monomer to the fluorous-tagged construct, a fluorous solid-phase extraction (FSPE) technology is used to purify the fluorous tagged oligomeric product. Fast solution-phase kinetics of both reactions, coupled with the FSPE technology makes this platform a unique and efficient approach for synthesizing sequence-defined oligoTEAs. The final oligoTEA construct is obtained following acid deprotection of the fluorous tag and Boc groups and HPLC purification.

Almost all AMPs have a net cationic charge and significant hydrophobic domains. In an effort to mimic these chemical features, AOTs were designed to contain cationic pendant groups using an amino-N-allylacrylamide monomer, and a tunable hydrophobic backbone using a dithiols with varying degrees of hydrophobicity.

AOTs are bactericidal and selective. Since gram-positive cocci are the leading cause of bacterial infections in humans, studies were performed with gram-positive bacteria. AOTs were tested on methicillin-resistant *Staphylococcus aureus* (MRSA), B. *Subtilis*. The antibacterial activities, reported as the minimum inhibitory concentration (MIC), against the bacterial strains are shown in the figures. To place these activities in perspective, three positive controls were tested, melittin, vancomycin and daptomycin. MRSA is more difficult to kill than the non-pathogenic strain, B. *Subtilis*. Melittin is a traditional membrane permeabilization agent that undergoes rapid pore formation when dosed at a concentration above its MIC value. Vancomycin on the other hand is a cell-wall interfering agent known to bind to the pentapeptide sequence of lipid.

Figure 4:
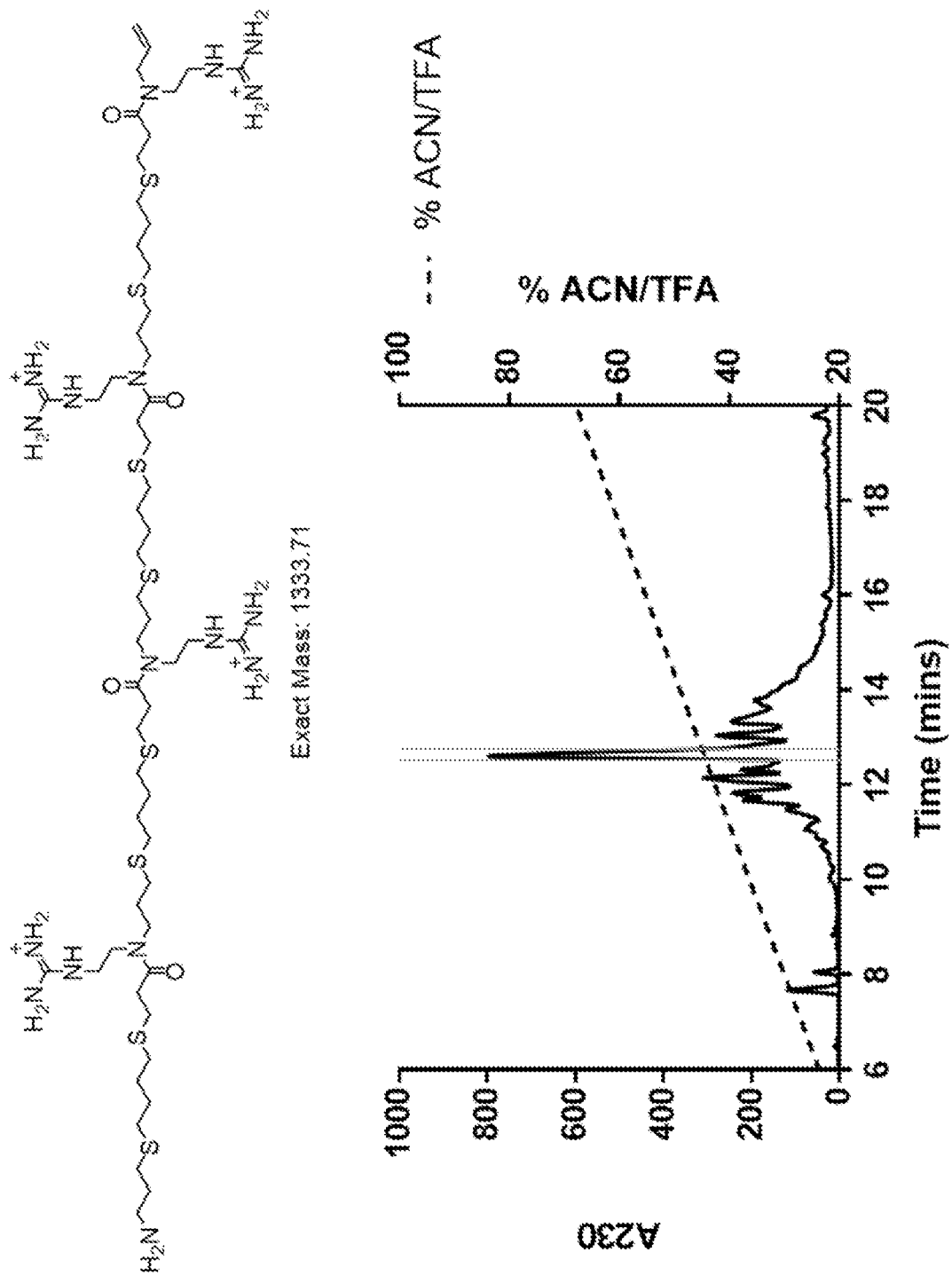
FIG. 4 shows (top) the structure of BDT-4G (composed of four 1,4 butanedithiol monomers and four guanidinium-based N-allylacrylamide monomers in a defined sequence) and (bottom) an HPLC trace of the cleavage reaction of Ftag-BDT-4G. The peak at 12.6 min was collected, dried and checked by $^1$H NMR.
Figure 5:
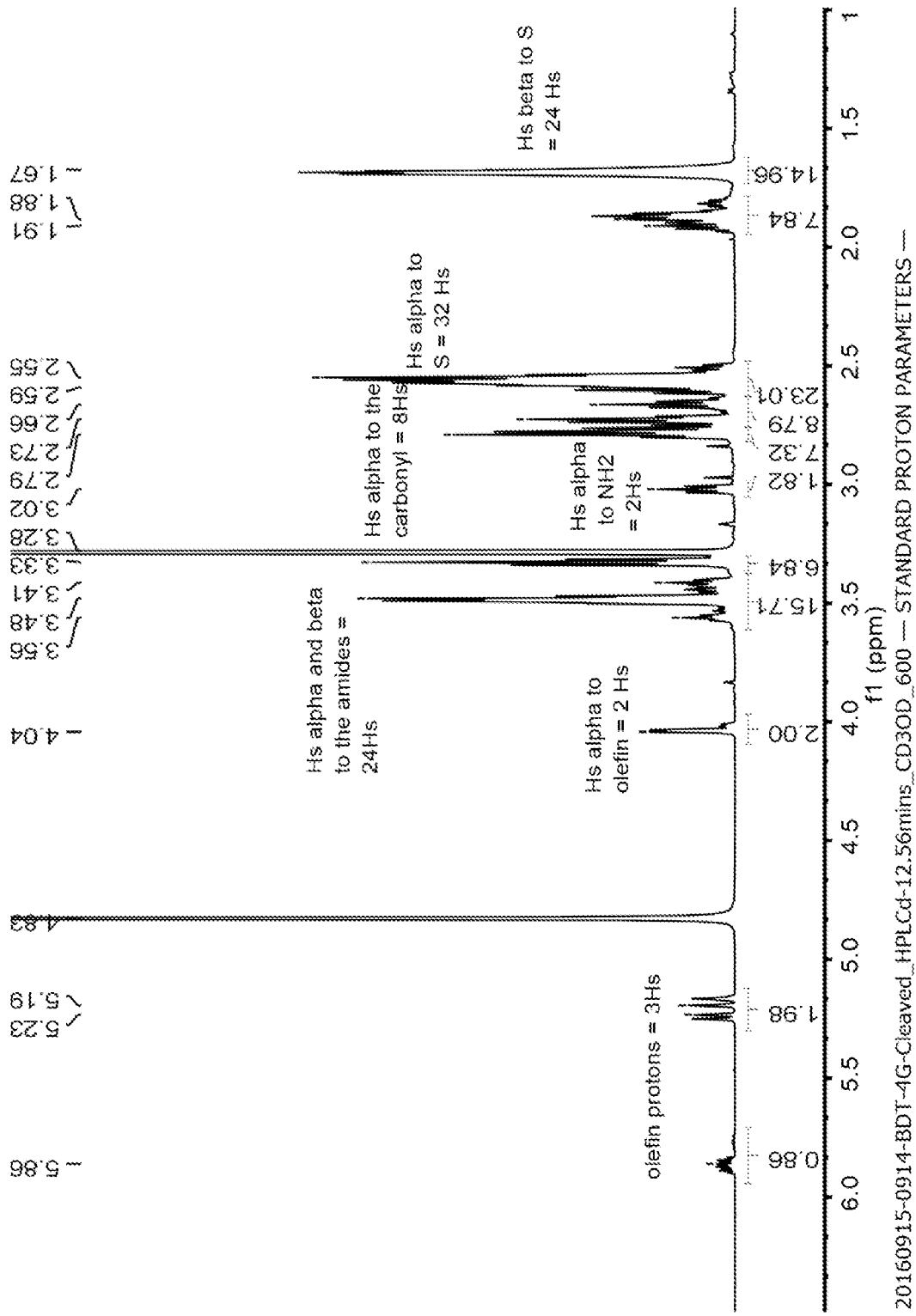
FIG. 5 shows an $^1$H NMR spectrum of the pure BDT-4G, taken in $CDCl_3$ on a 600 MHz NMR spectrometer.
Figure 6:
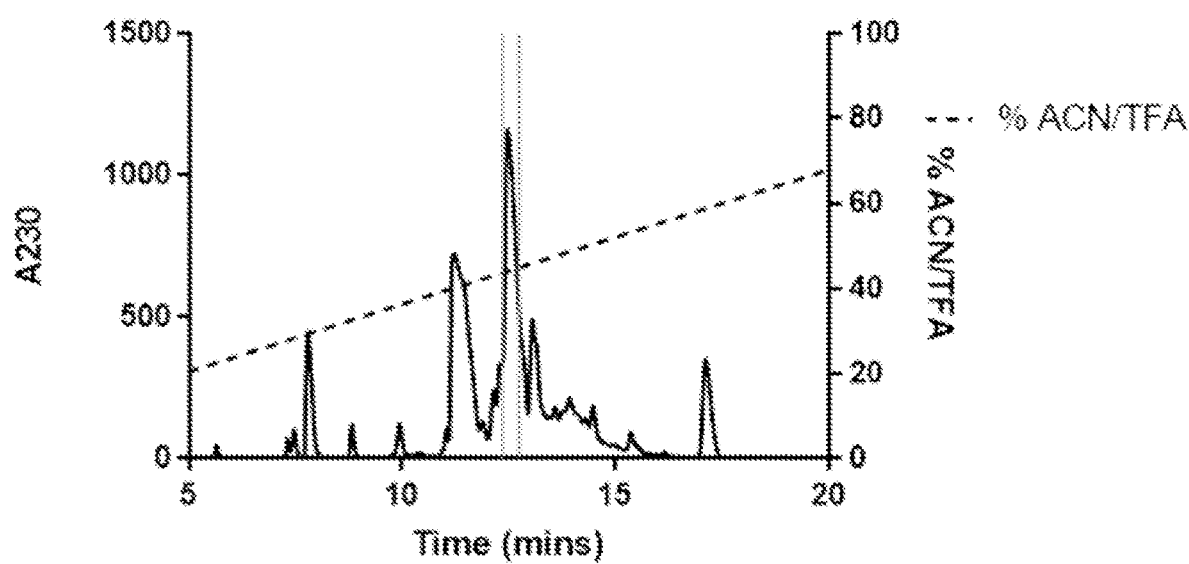
FIG. 6 shows an HPLC trace of the cleavage reaction of Ftag-BDT-4G. The peak at 12.5 min was collected, dried and checked by $^1$H NMR.
Figure 7:
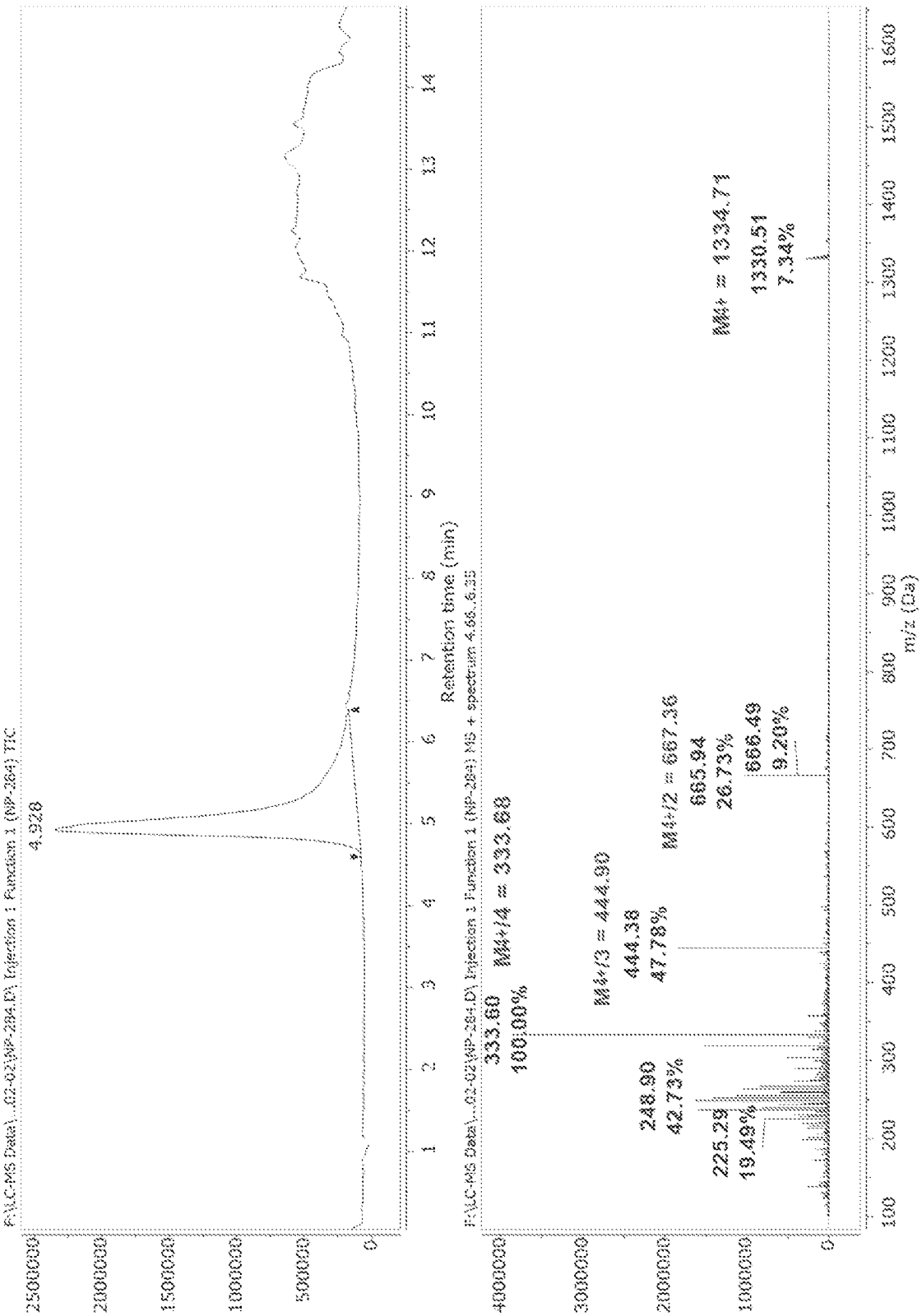
FIG. 7 shows an LC-MS spectrum of the pure BDT-4G collected from HPLC purification.

Finally, the extent of AOT cytotoxicity against mammalian cells was measured via a hemolysis assay a dose of 0.5-50 µM (FIG. 4). The data show that AOTs were non hemolytic (<10%), far less hemolytic than melittin. The AOT cytotoxicity was examined on human embryonic kidney cells (HEK293 cell line) using an MTS assay. This assay was performed by incubating AOTs with cells for 24 hours in contrast to the 1 hour incubation period for the hemolysis assay. Results from the MTS experiment, performed at 5-40 µM, showed non hemolytic activity at low concentrations.

Bacterial cell death kinetics correlates with hydrophobicity. To investigate the mode of killing, growth/kill kinetics measurements were performed with B. *Subtilis* in log phase ($OD_{600}$=0.5) exposed to AOTs and the antibiotics vancomycin, melittin and rifampicin as mechanistic controls.

Membrane permeabilization dictates lytic potential. A cytoplasmic permeability assay was performed using propidium iodide (PI). PI is a cell impermeant intercalating agent that fluoresces when bound to nucleic acids. As such, PI can be used to identify cells with compromised membranes by measuring an increase in fluorescence above the baseline. This phenomenon was qualitatively confirmed by performing fluorescence microscopy studies incubated with PI with or without the AOTs. In the presence of vancomycin, PI was unable to gain entry into cells, however, in the presence of AOTs, staining was observed, indicating that AOTs facilitate PI transport presumably by forming holes in the bacterial membrane. It is easier to disrupt the bacterial membrane than the mammalian cell membrane, and supports previous findings that some characteristic of the mammalian cell membrane, perhaps the presence of cholesterol, suppresses bilayer disruption.

AOTs are active in serum. Finally, the activity of oligoTEAs was tested in the presence of serum. A common Achilles heel of most AMPs is their poor activity in the presence of serum due to rapid degradation by serum proteases and/or non-specific binding to serum proteins. The activity of most AMPs has been shown to decrease by 5 to 20-fold in the presence of serum. Unlike AMPs, AOTs have an abiotic backbone and are thus not susceptible to protease degradation. However, since their mode of cell attachment is presumably in part due to their cationic sites (amine groups), they could still be susceptible to serum protein binding and reduced activity. The amount of fetal bovine serum (FBS) used was limited to 20%. The results show that the presence of 20% fetal bovine serum improves antibacterial activity.

Figure 9:
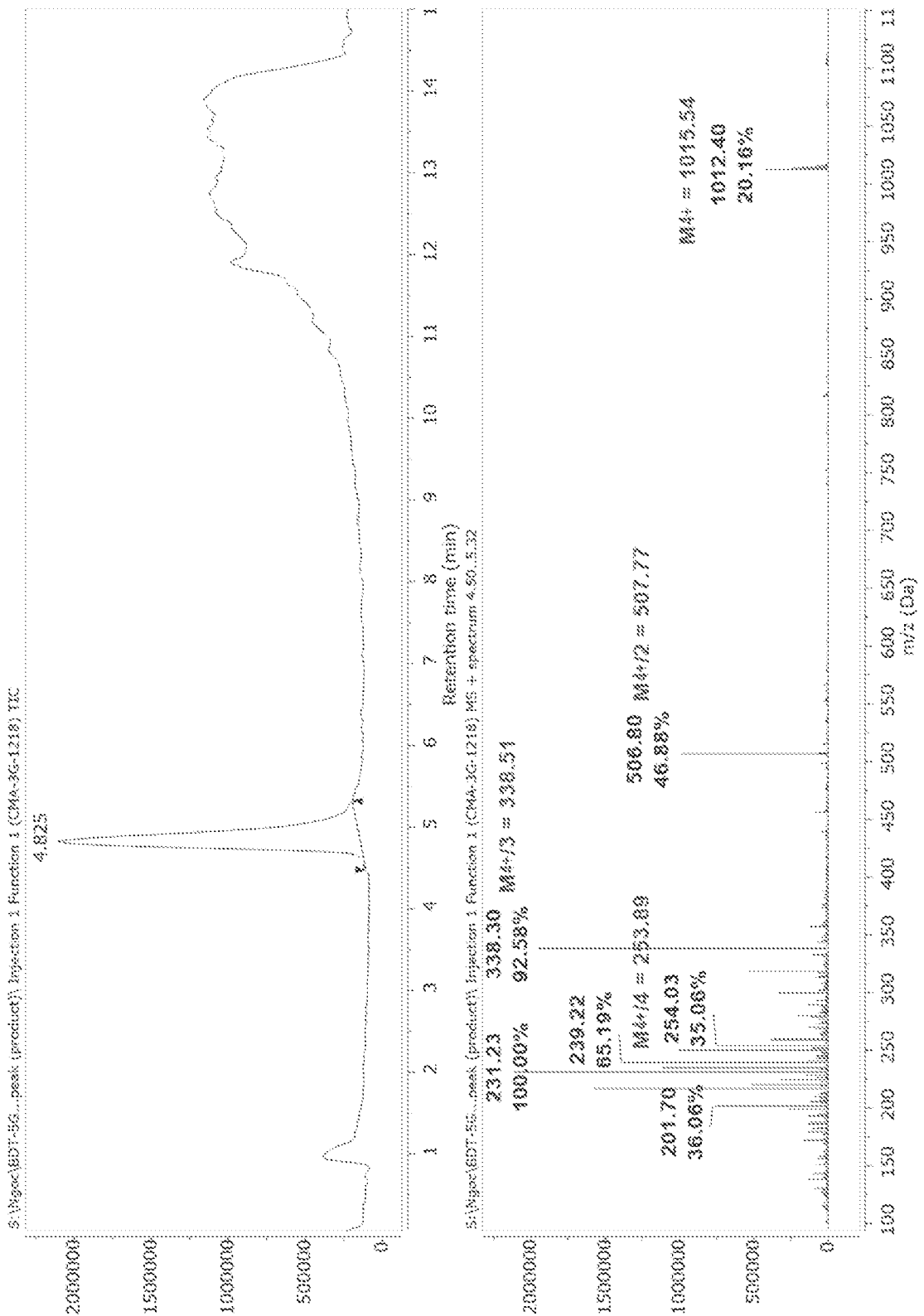
FIG. 9 shows an LC-MS spectrum of the fraction collected at 12.2 min from the HPLC purification of Ftag-BDT-3G.
Figure 10:
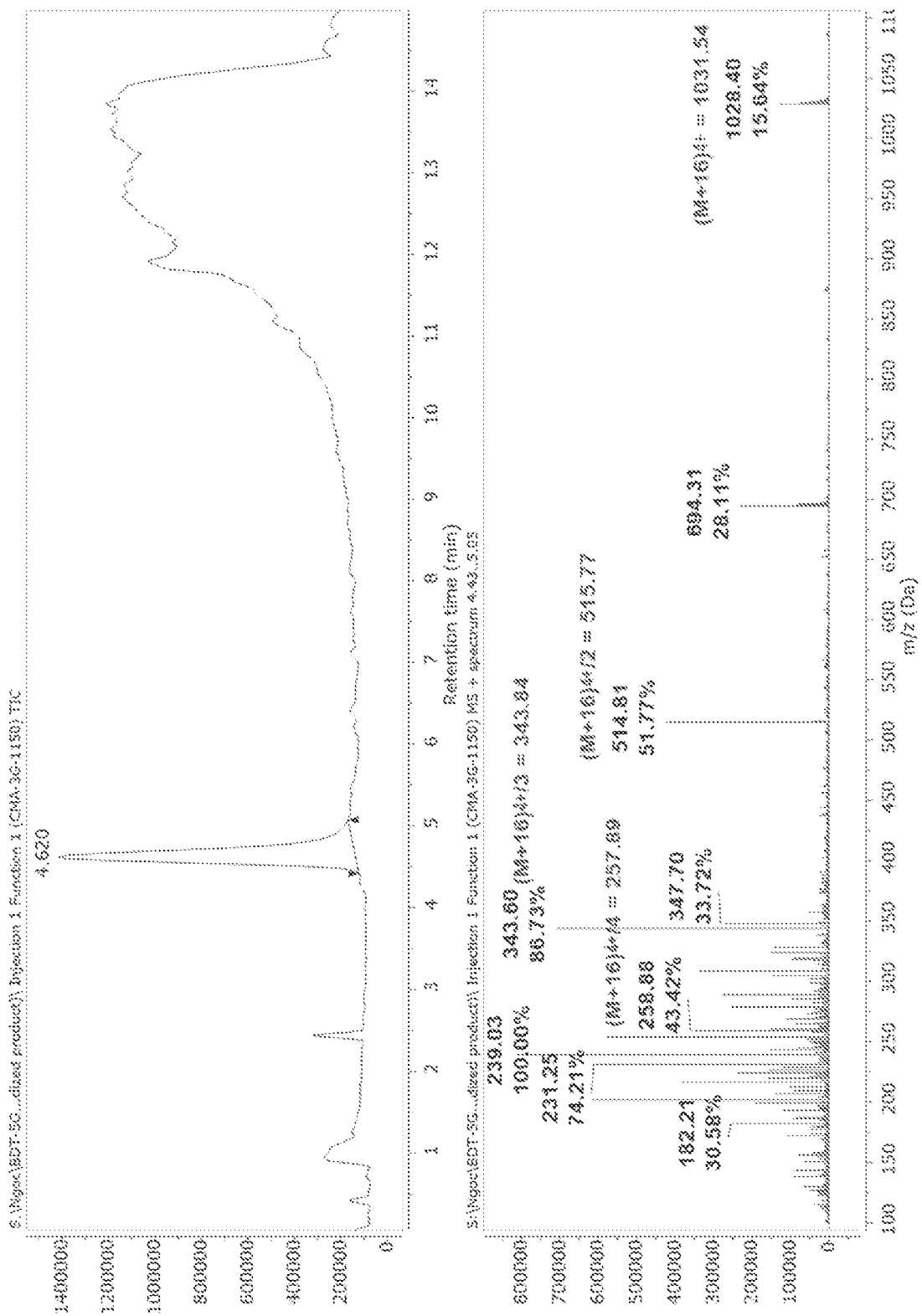
FIG. 10 shows an LC-MS spectrum of the fraction collected at 11.5 min from the HPLC purification of Ftag-BDT-3G.
Figure 12:
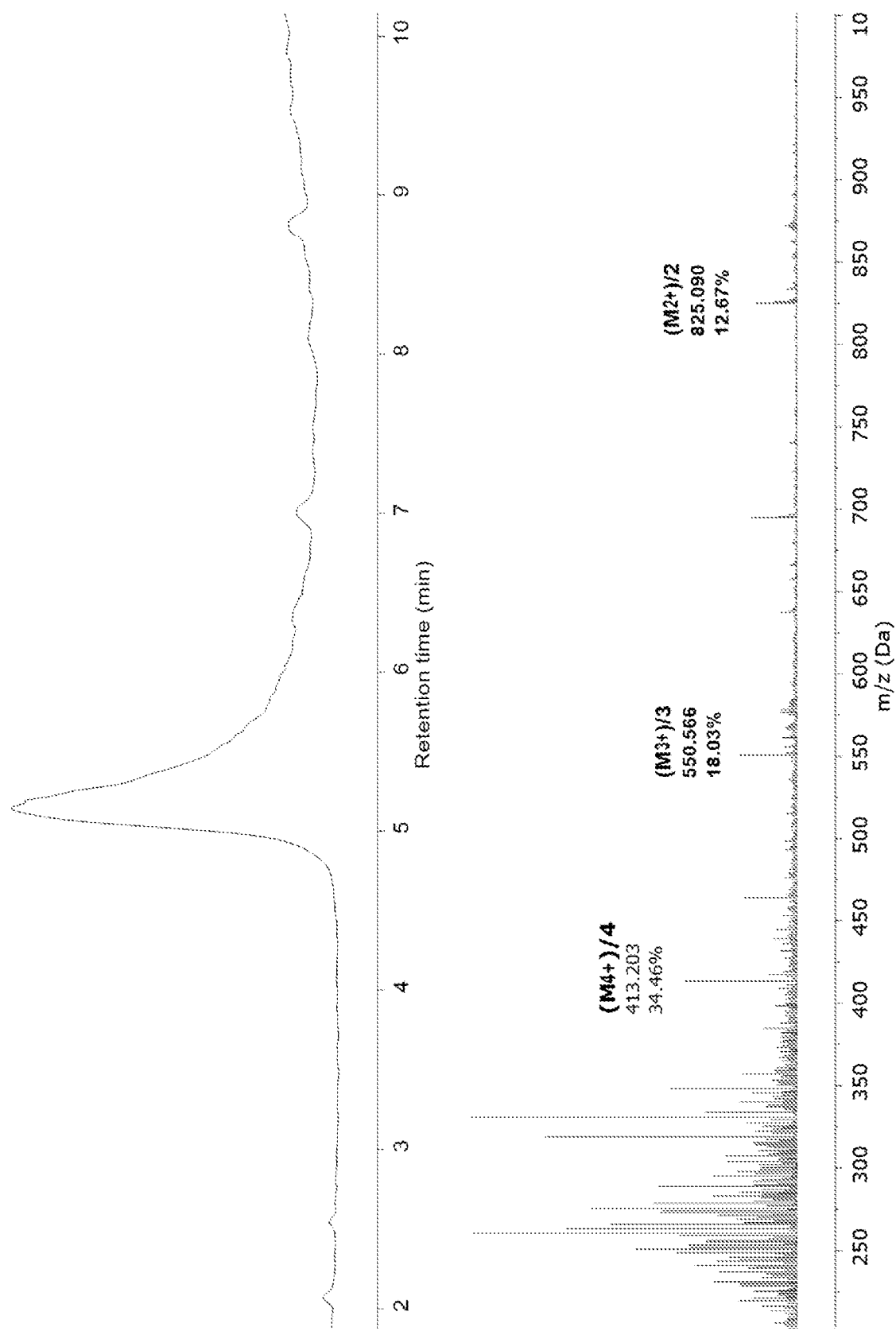
FIG. 12 shows an LC-MS spectrum of the fraction collected at 13.4 min from the HPLC purification of Ftag-BDT-5G.
Figure 13:
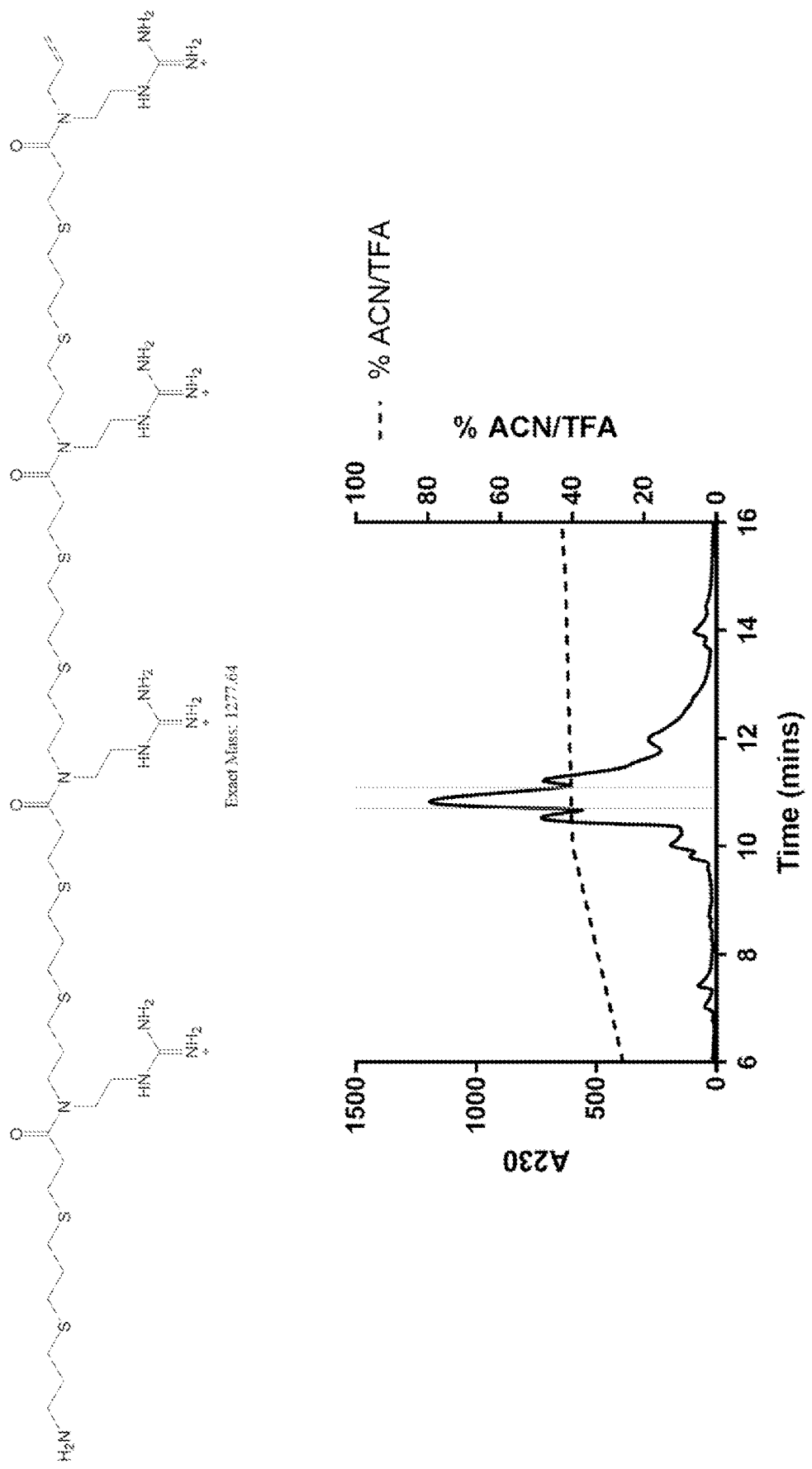
FIG. 13 shows (top) the structure of PDT-4G (composed of four 1,3-propanedithiol monomers and four guanidinium-based N-allylacrylamide monomers in a defined sequence) and (bottom) an HPLC trace of the cleavage reaction of Ftag-PDT-4G. The peak at 10.85 min was collected, dried and checked by LC-MS.
Figure 14:
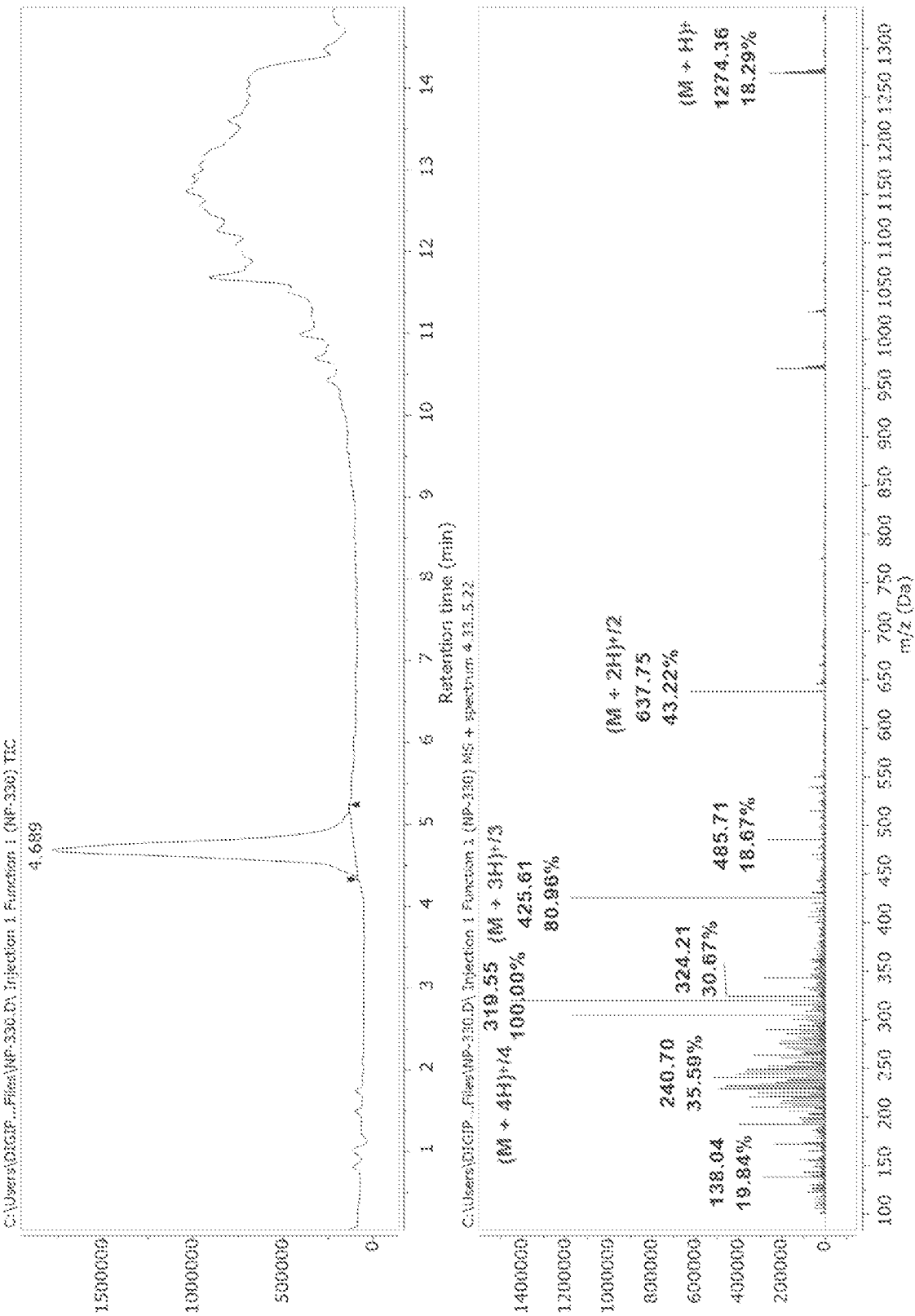
FIG. 14 shows an LC-MS spectrum of the peak collected at 10.85 min from the HPLC purification of PDT-4G.
Figure 15:
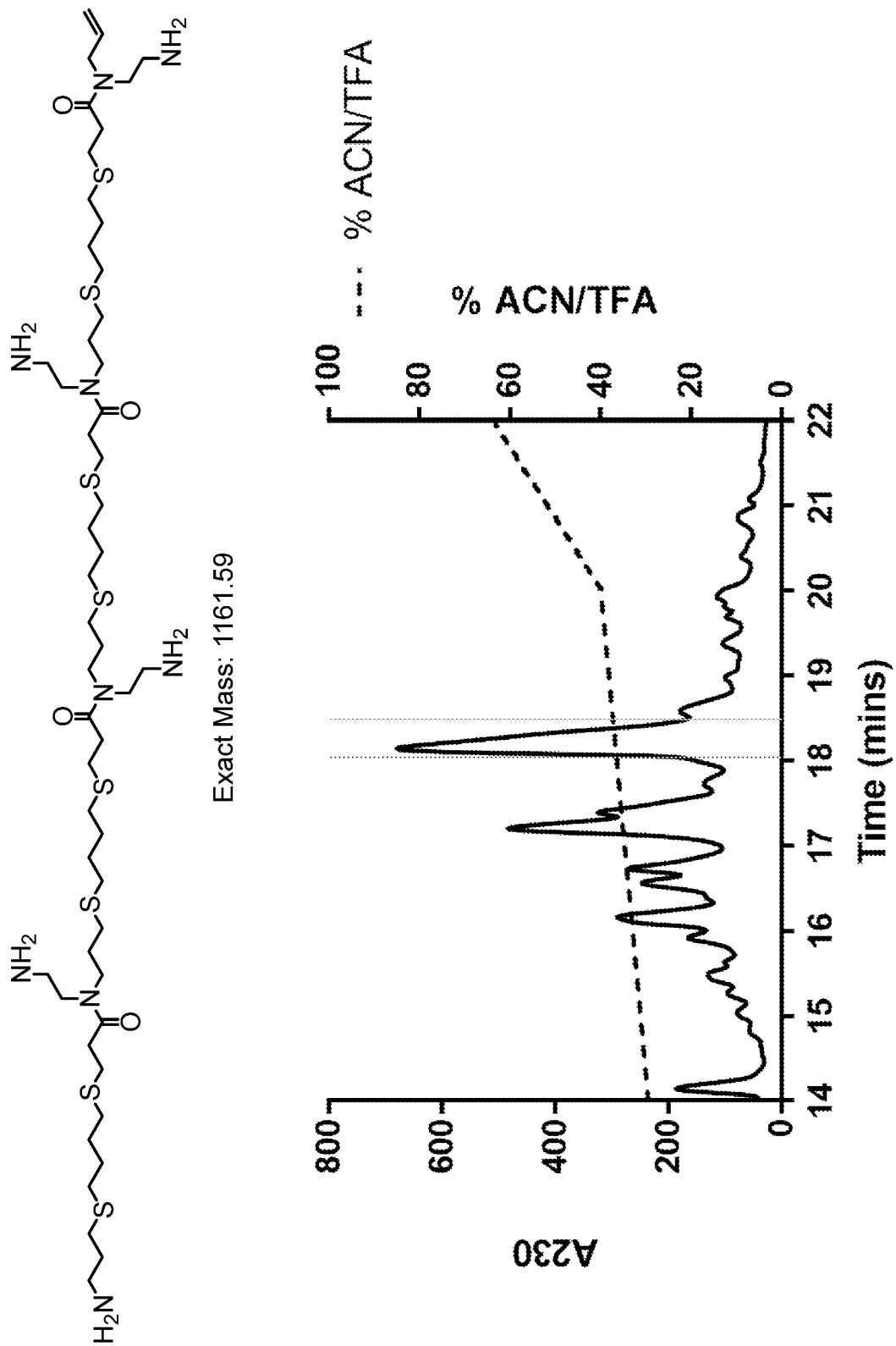
FIG. 15 shows (top) the structure of BDT-4A (composed of four 1,4 butanedithiol monomers and four amine-based N-allylacrylamide monomers in a defined sequence) and (bottom) an HPLC trace of the cleavage reaction of Ftag-BDT-4A. The peak at 18.2 min was collected, dried and checked by LC-MS.
Figure 16:
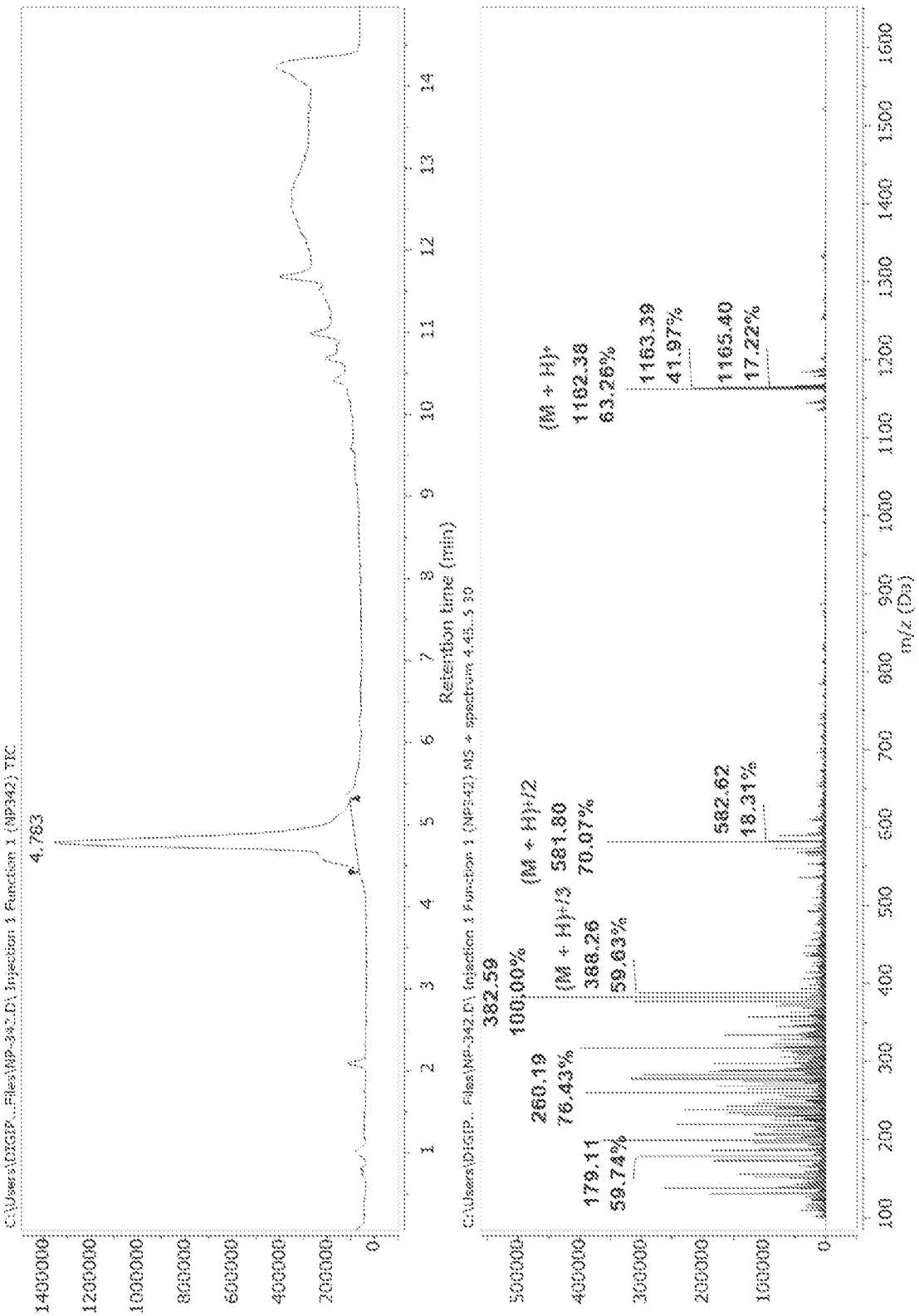
FIG. 16 shows an LC-MS spectrum of the peak collected at 18.2 min from the HPLC purification of BDT-4A.
Figure 17:
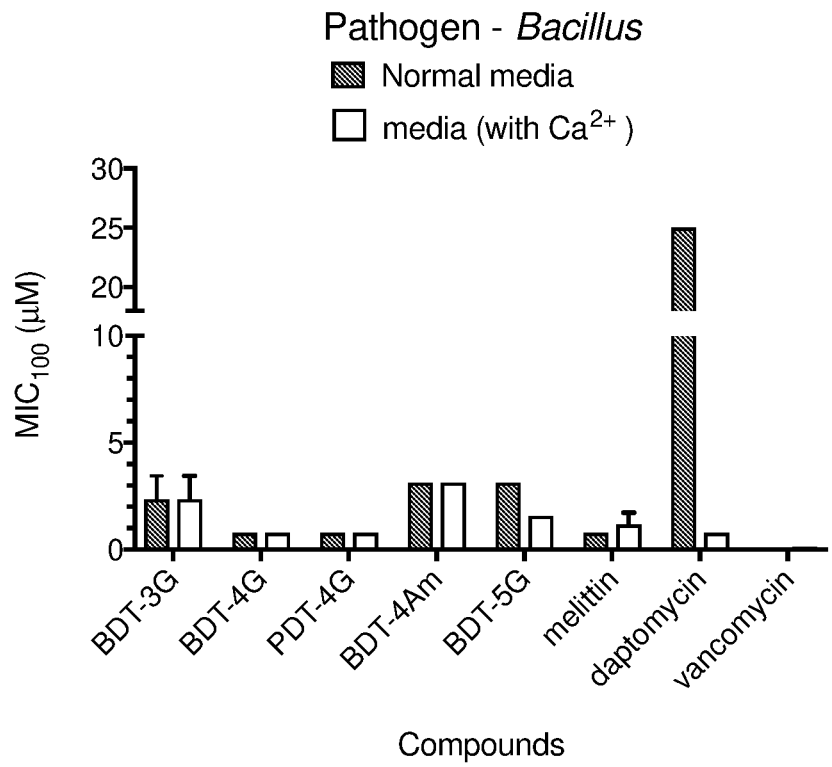
FIG. 17 shows antibacterial activity data, measured as the minimum concentration required inhibit the growth of all bacteria (MIC100), of oligoTEA compounds against *Bacillus subtilis*. BDT-3G, BDT-4G, BDT-5G, BDT-4Am and PDT-4G compounds show activity in both normal (LB media) media and maintain their antibacterial activity in the presence of elevated calcium and magnesium ions (25 mM). BDT-4G and PDT-4G are the best performing materials in this assay.
Figure 18:
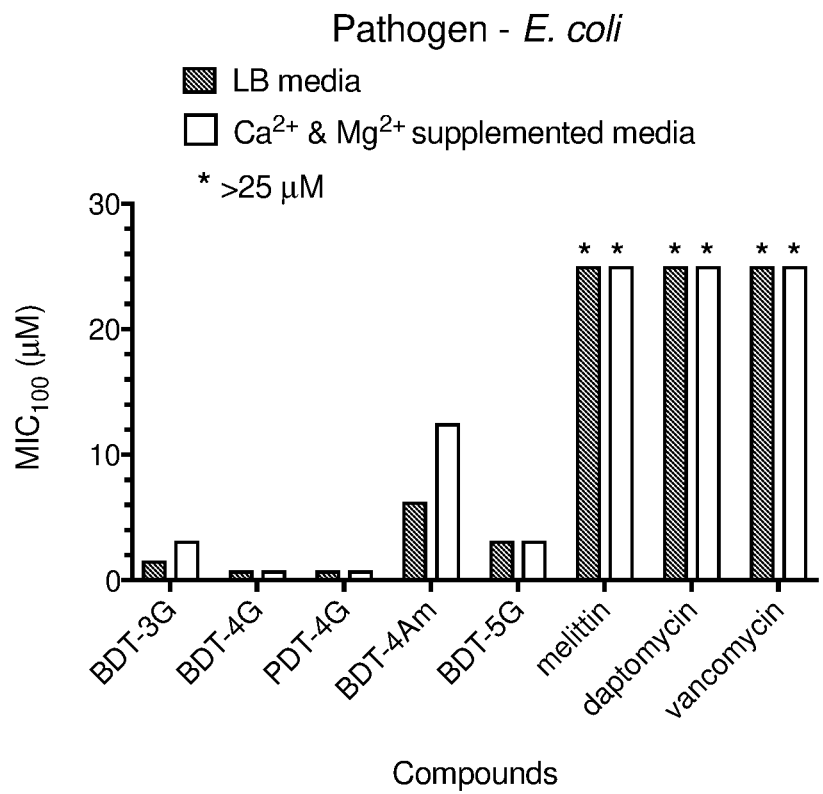
FIG. 18 shows antibacterial activity data, measured as the minimum concentration required to inhibit the growth of all bacteria (MIC100), of oligoTEA compounds against *E. coli*. BDT-3G, BDT-4G, BDT-5G, and PDT-4G compounds show activity in both normal (LB media) media and maintain their antibacterial activity in the presence of elevated calcium and magnesium ions (25 mM). BDT-4G and PDT-4G are the best performing materials in this assay.
Figure 19:
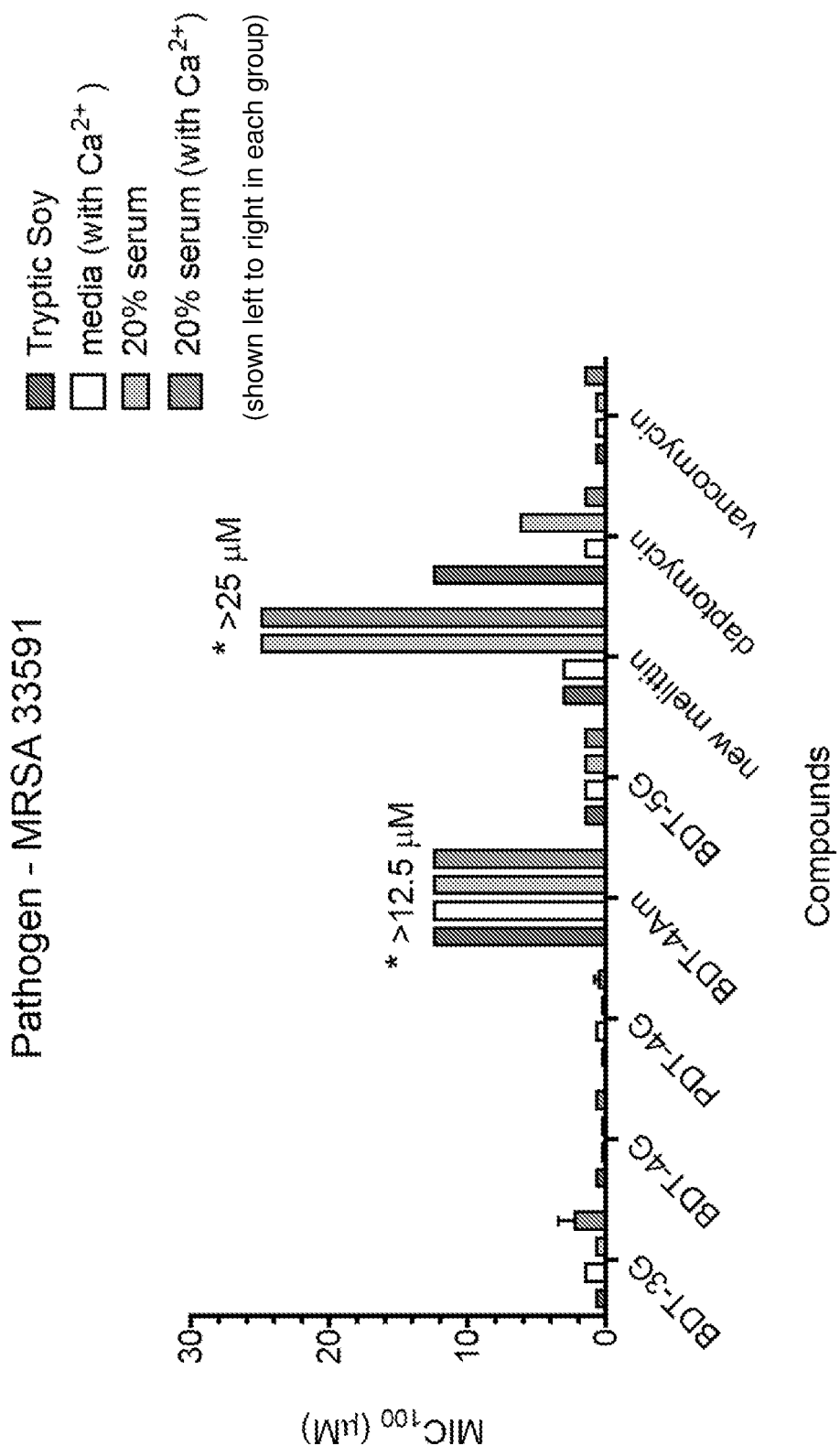
FIG. 19 shows antibacterial activity data, measured as the minimum concentration required inhibit the growth of all bacteria (MIC100), of oligoTEA compounds against methicillin resistant *Staphylococcus aureus* (MRSA). BDT-3G, BDT-4G, BDT-5G, and PDT-4G compounds show activity in both normal (Tryptic Soy media) media and maintain their antibacterial activity in the presence of elevated calcium and magnesium ions (25 mM) and in the presence heat-inactivated fetal bovine serum. BDT-4G and PDT-4G are the best performing materials in this assay.
Figure 20:
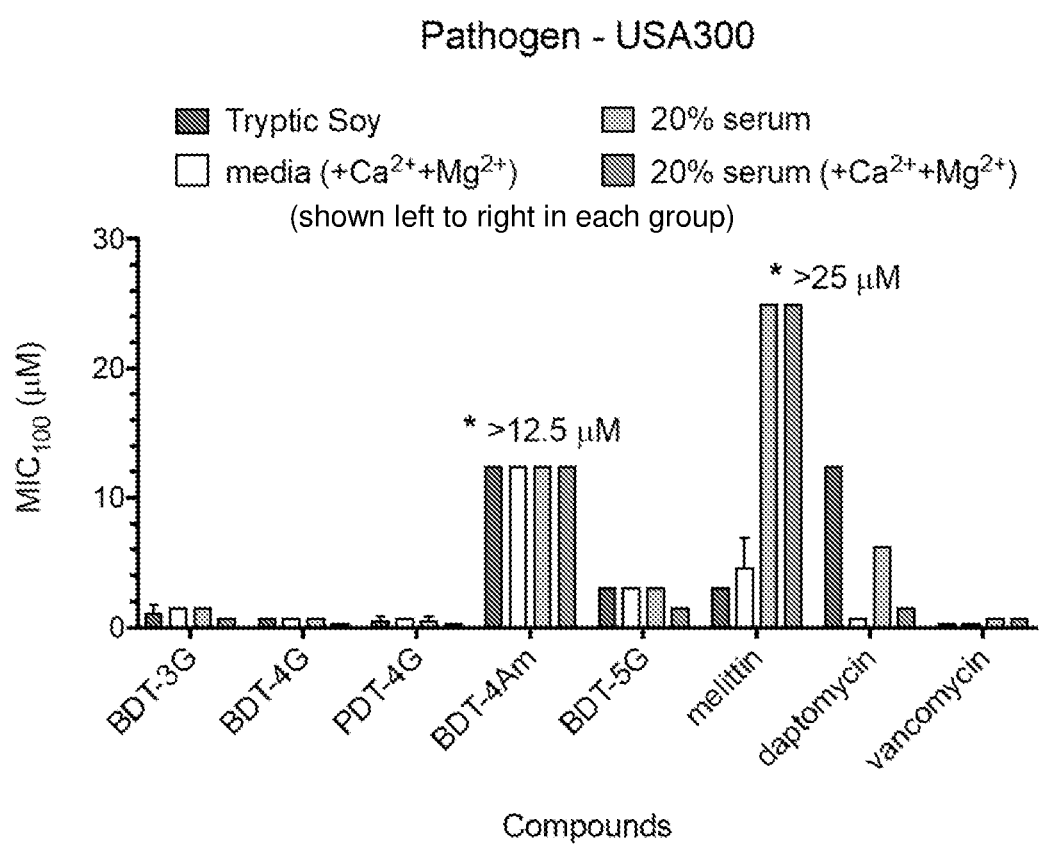
FIG. 20 shows antibacterial activity data, measured as the minimum concentration required inhibit the growth of all bacteria (MIC100), of oligoTEA compounds against community associated *Staphylococcus aureus* (strain USA300). BDT-3G, BDT-4G, BDT-5G, and PDT-4G compounds show activity in both normal (Tryptic Soy media) media and maintain their antibacterial activity in the presence of elevated calcium and magnesium ions (25 mM) and in the presence heat-inactivated fetal bovine serum. BDT-4G and PDT-4G are the best performing materials in this assay.
Figure 22:
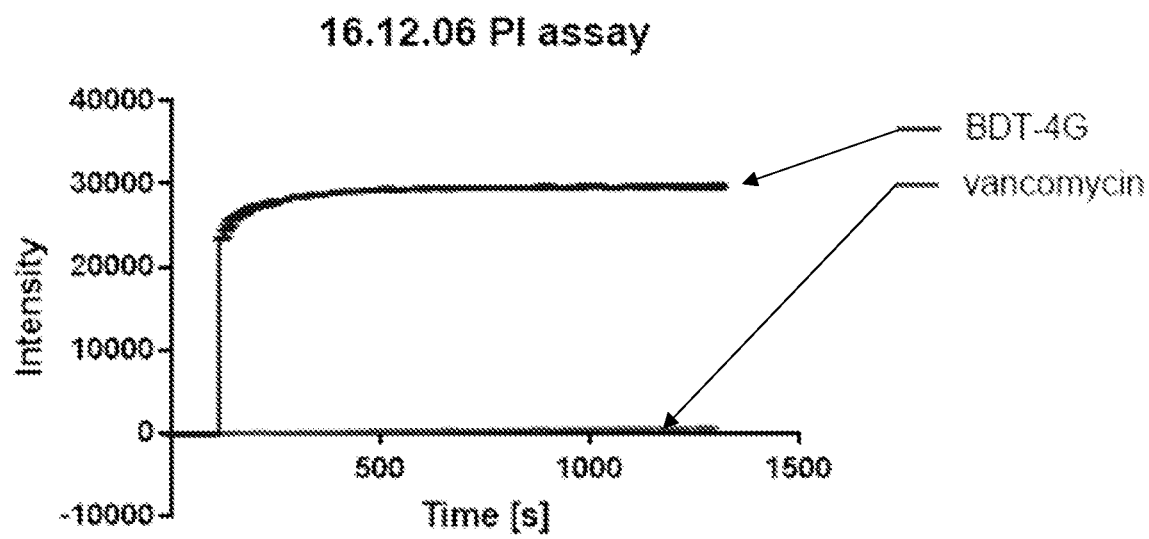
FIG. 22 shows BDT-4G destabilizes cell membrane of methicillin resistant *Staphylococcus aureus* (MRSA), thus allowing diffusion of the propidium iodide dye in to the cell. Vancomycin, known not to permeabilize the membrane shows no membrane compromise (line parallel '0' intensity).
Figure 23:
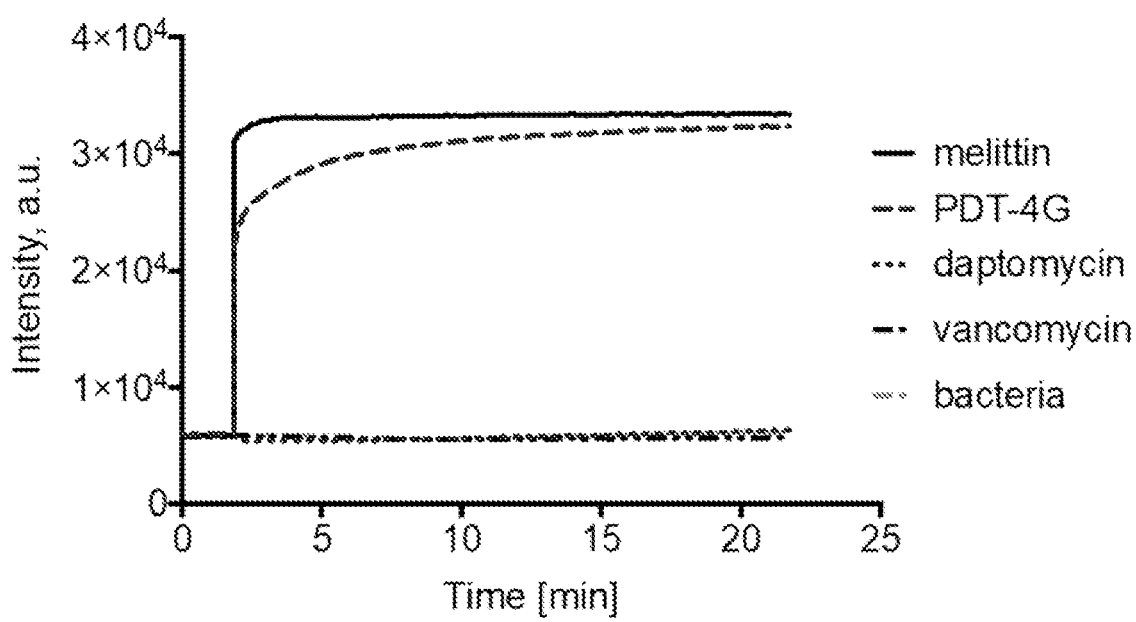
FIG. 23 shows PDT-4G destabilizes the membrane of MRSA, thus allowing diffusion of the propidium iodide dye in to the cell, similar to melittin (solid line near top). Vancomycin and daptomycin, known not to permeabilize the membrane show no membrane compromise.
Figure 24:
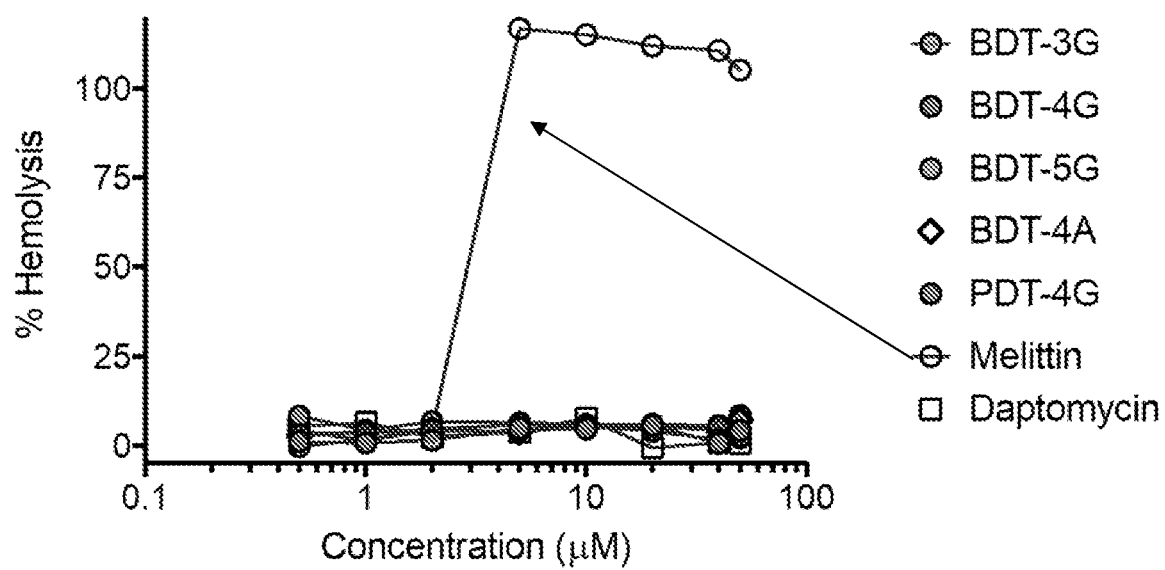
FIG. 24 shows data depicting melittin with 100% hemolysis when exposed to red blood cells. The other listed compounds demonstrate minimal to no hemolysis.
Figure 25:
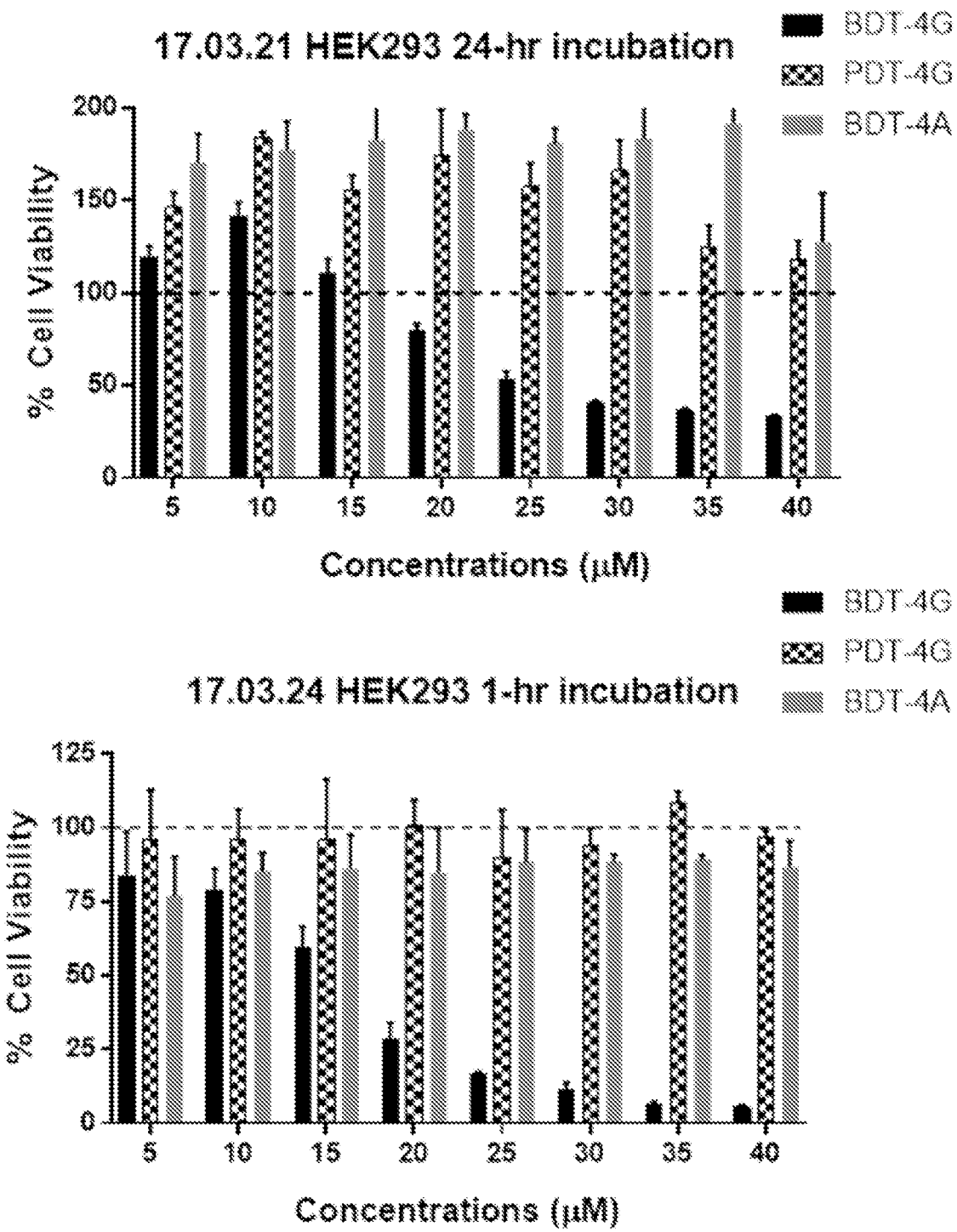
FIG. 25 shows cell viability data (HEK293 cells) for various concentrations of the listed compounds as an indication of relative toxicity.
Figures 26, 27:
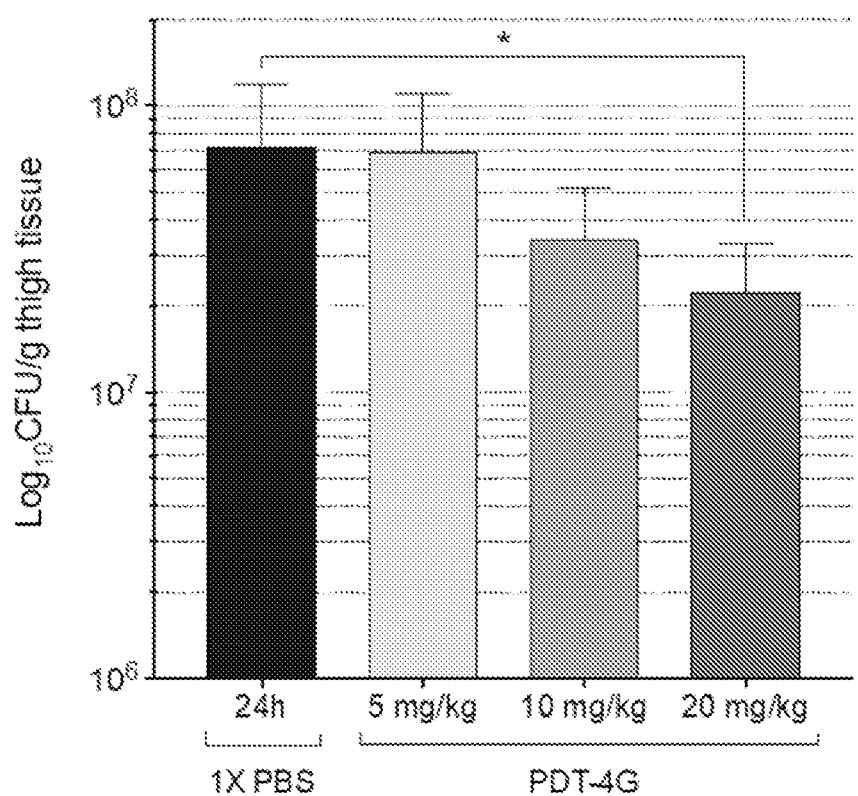
FIG. 26 shows data depicting MIC activity of oligoTEA compounds.
FIG. 27 shows a MRSA mouse thigh infection model. Female CD-1 mice were rendered neutropenic and treated 2 hours, after *S. aureus* (ATCC 33591) infection ($1 \times 10^6$ CFU/mL), with a single subcutaneous (s.c.) injection of PDT-4G. n=8 per group. * $p<0.05$. The PDT-4G compound shows a 0.5 Log 10 reduction in bacterial load.
Figure 28:
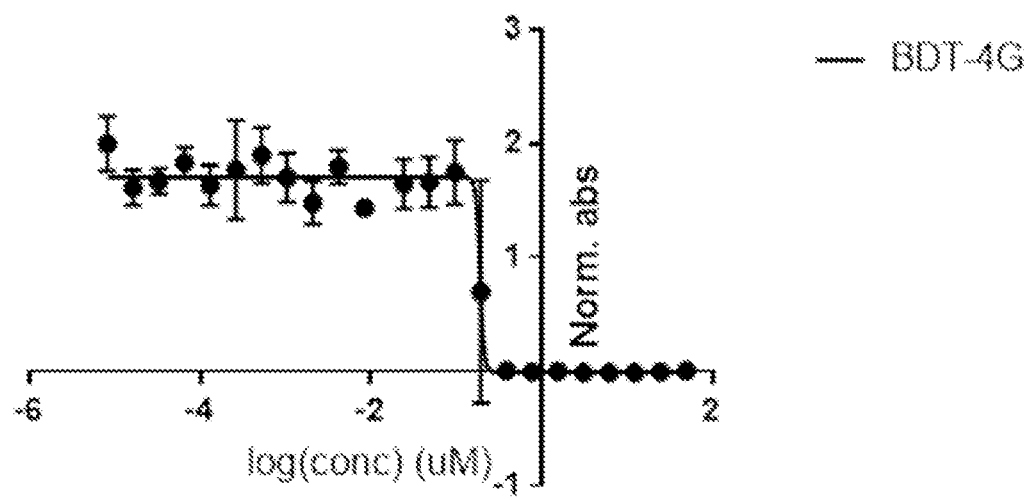
FIG. 28 shows data from a microbroth dilution assay to determine the MIC of BDT-4G on *B. subtilis*.
Figure 29:
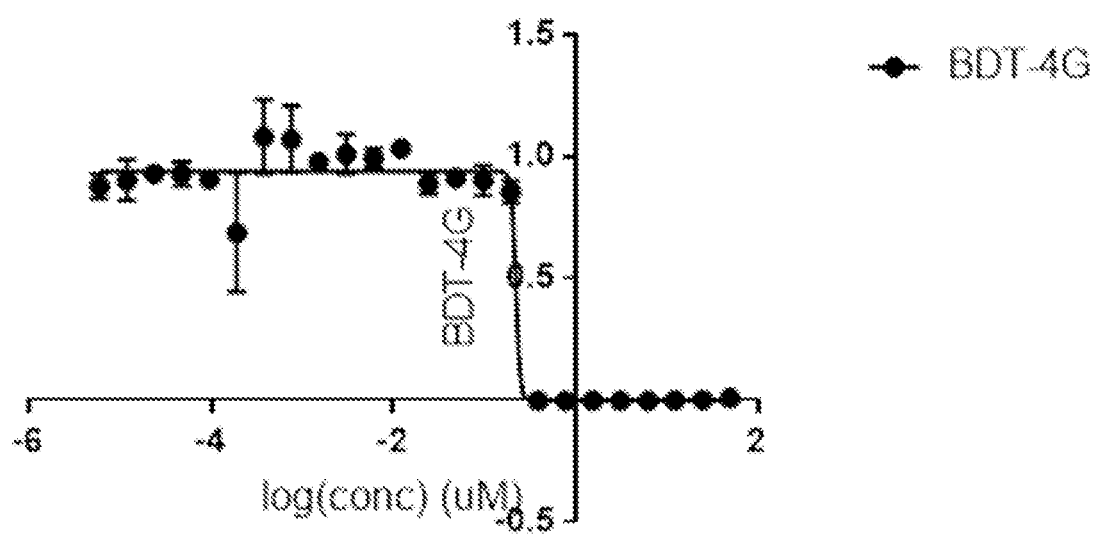
FIG. 29 shows data from a microbroth dilution assay to determine the MIC of BDT-4G on MRSA.
Figure 30:
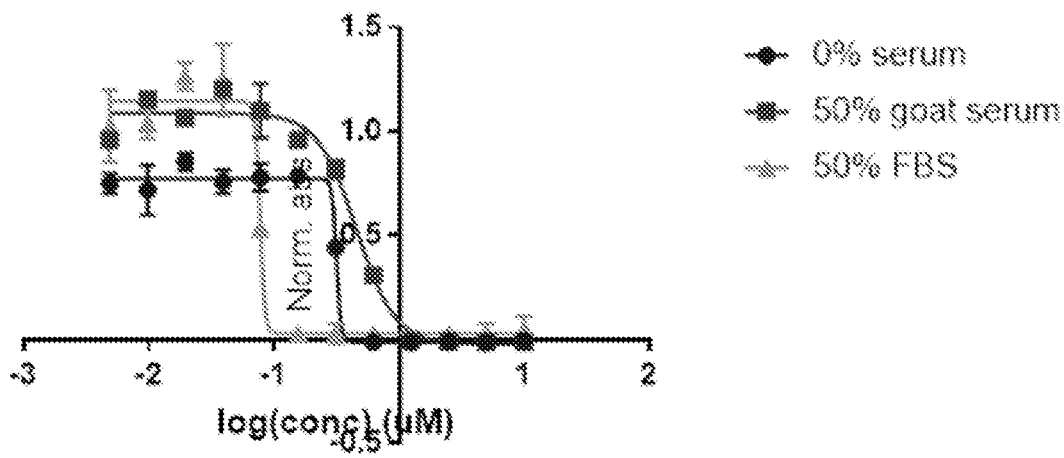
FIG. 30 shows data from a microbroth dilution assay to determine the MIC of BDT-4G on MRSA.
Figure 31:
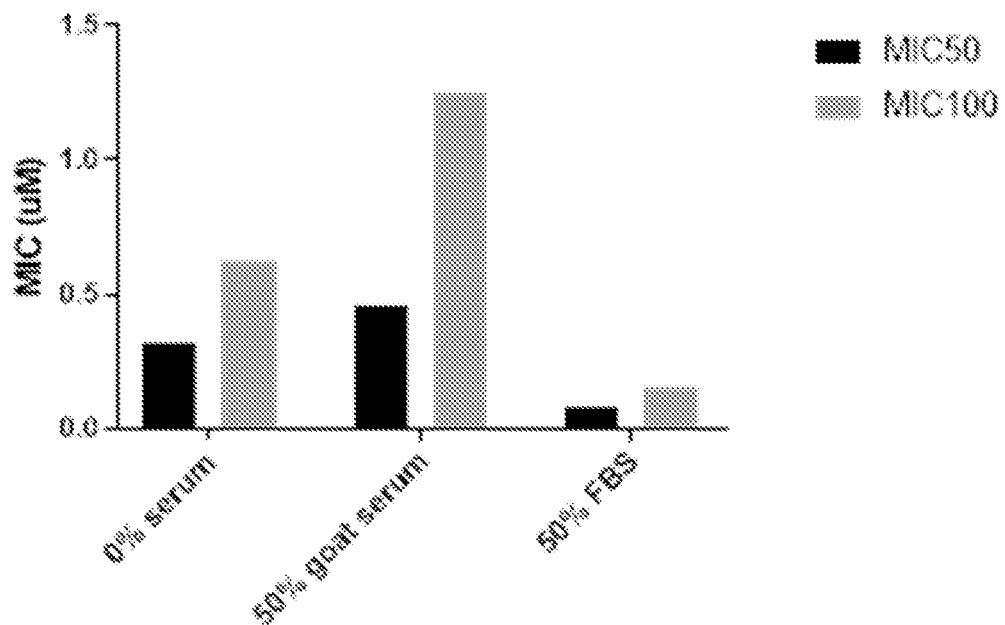
FIG. 31 shows MIC data of BDT-4G on MRSA in the presence of serum.
Figure 32:
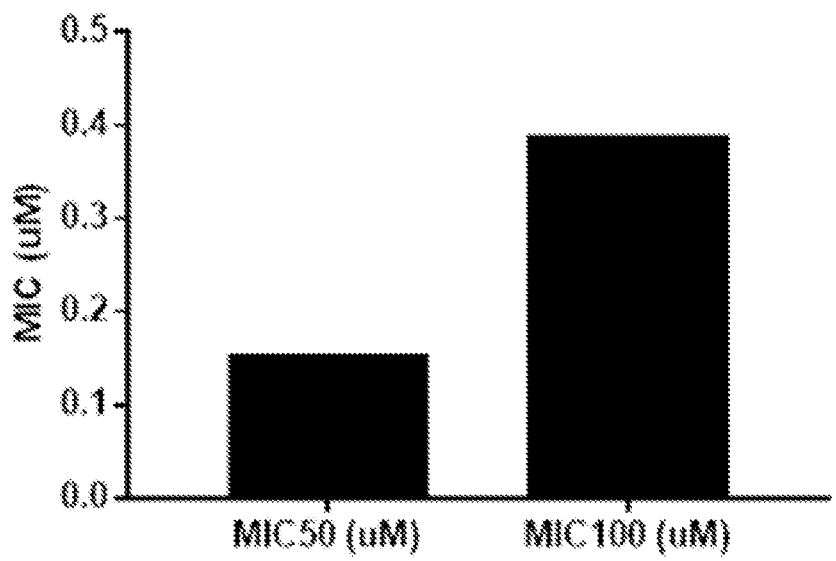
FIG. 32 shows MIC data of BDT-4G on *S. epidermis*.
Figure 33:
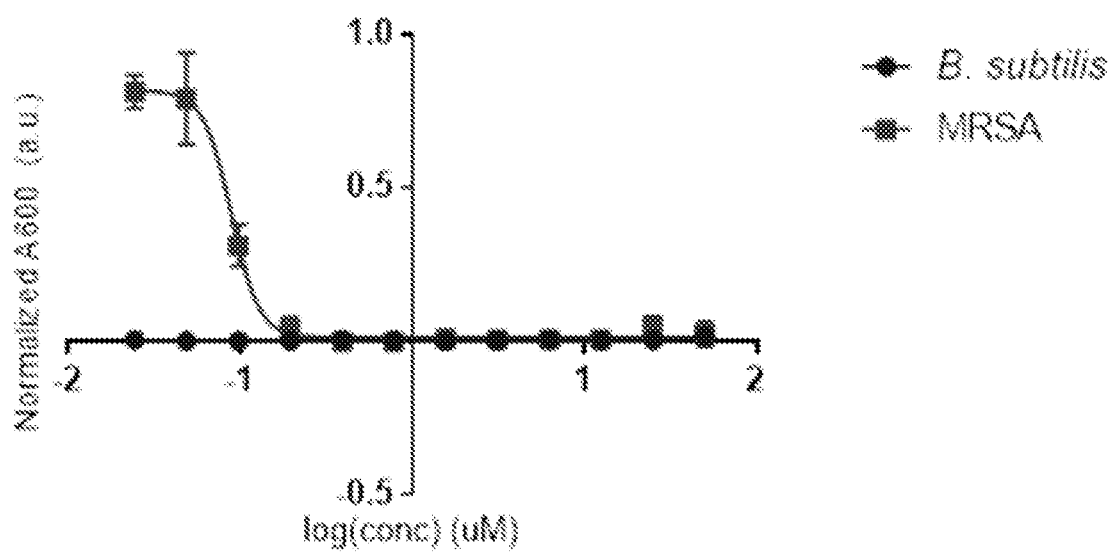
FIG. 33 shows data from a microbroth dilution assay to determine the MIC of BDT-4G on MRSA and *B. subtilis*.
Figure 34:
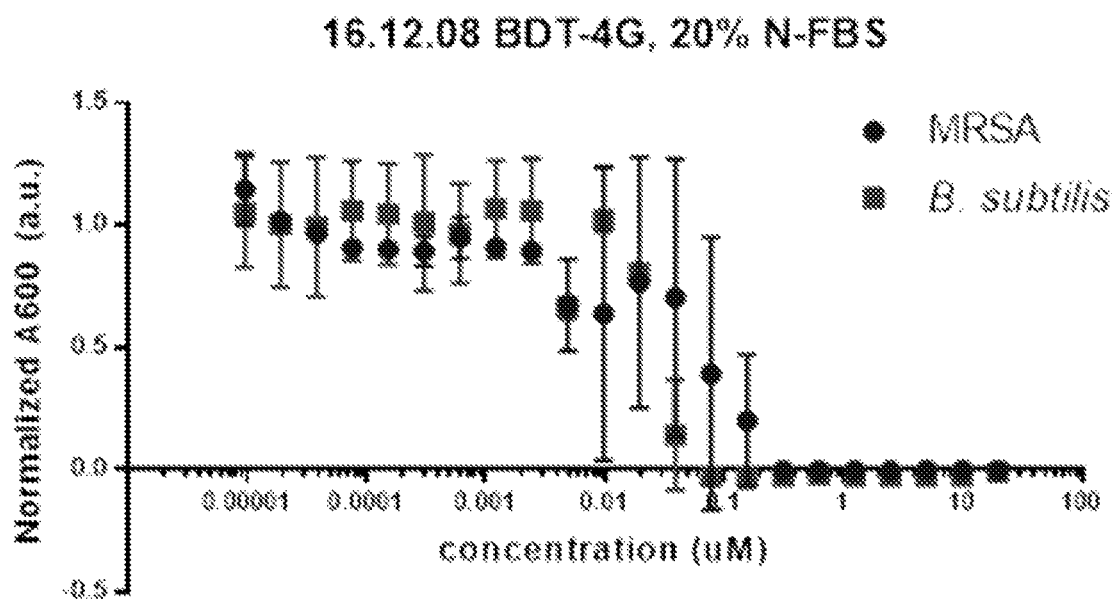
FIG. 34 shows data from a microbroth dilution assay to determine the MIC of BDT-4G on MRSA and *B. subtilis*.
Figure 35:
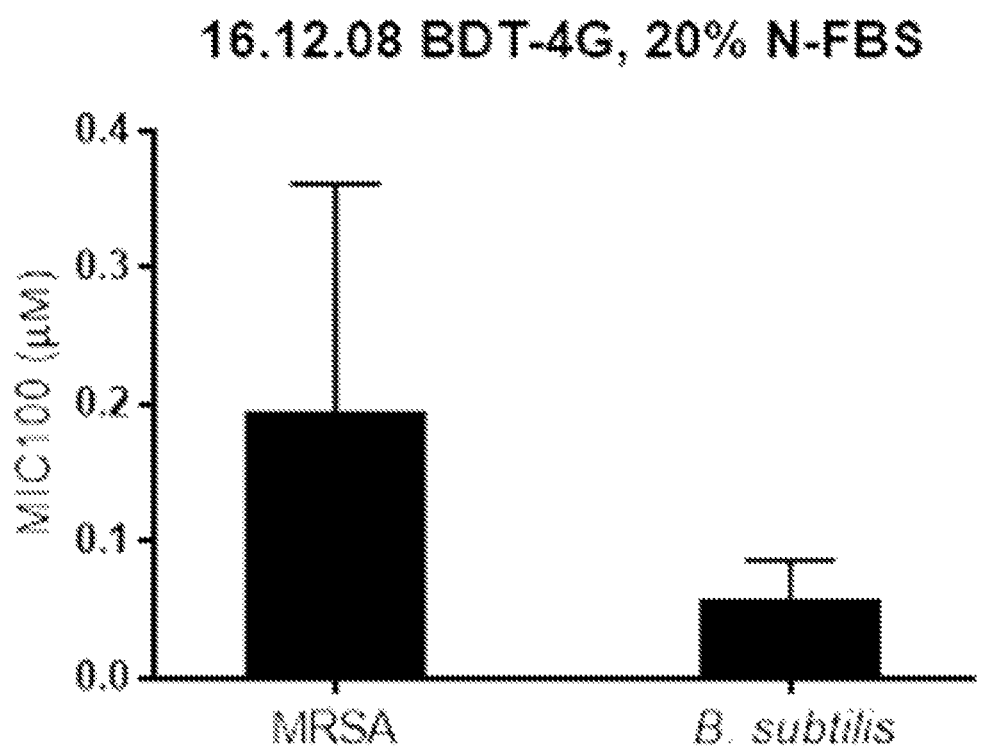
FIG. 35 shows MIC data of BDT-4G on MRSA and *B. subtilis* in the presence of serum.
Figure 36:
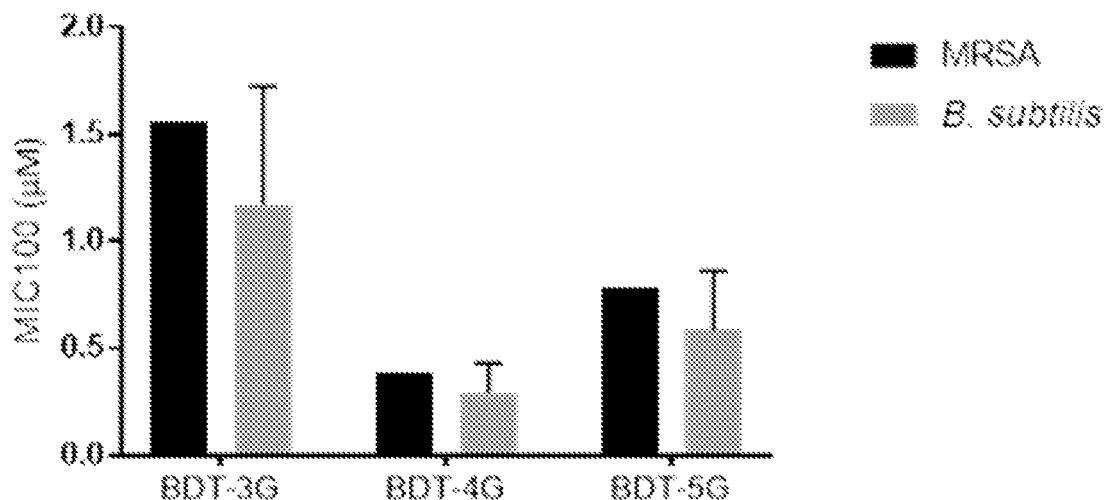
FIG. 36 shows MIC data of BDT-3G, BDT-4G and BDT-5G on MRSA and *B. subtilis*.
Figure 37:
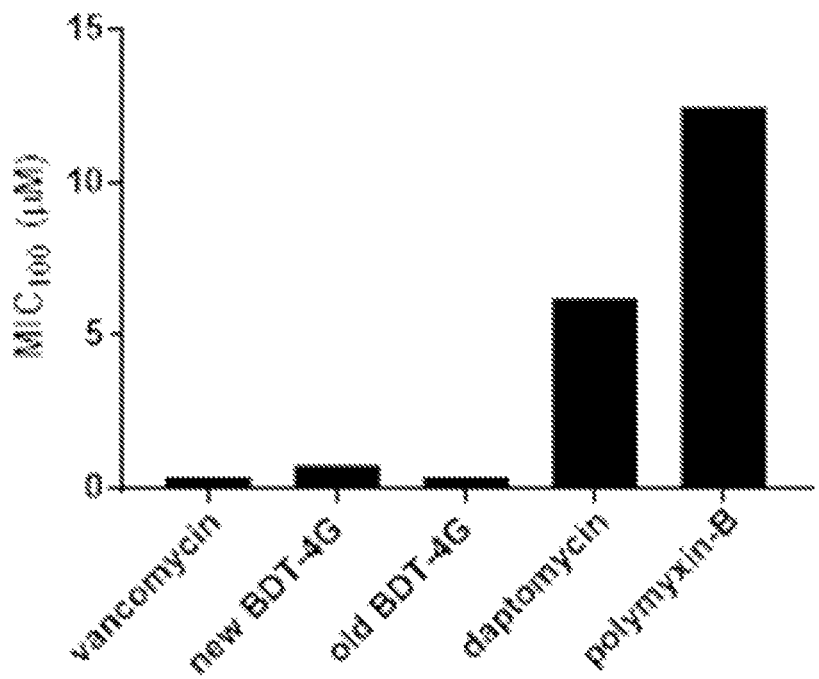
FIG. 37 shows MIC data of old (stored for several weeks in a refrigerator) and freshly prepared BDT-4G on *B. subtilis*.
Figure 38:
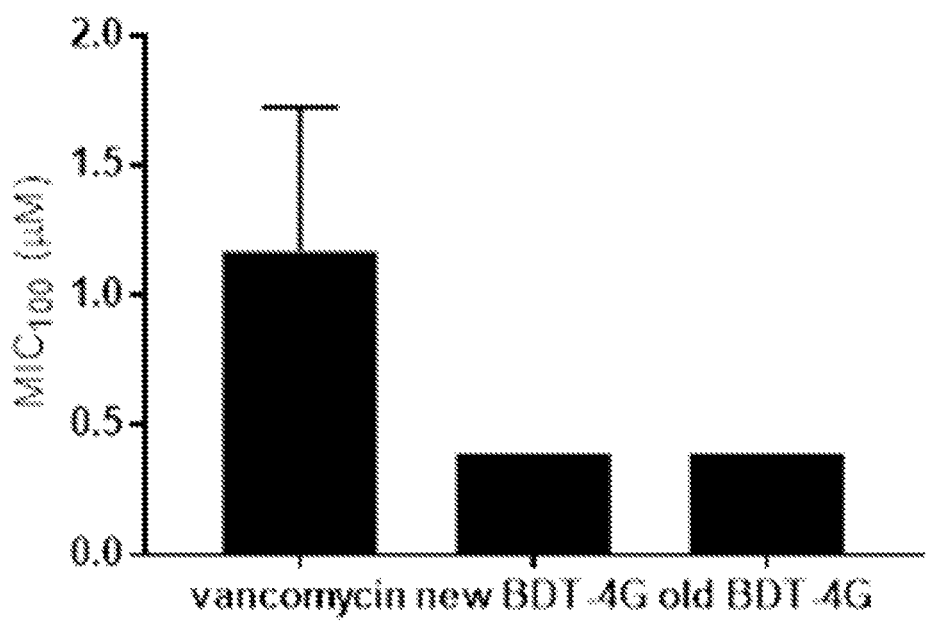
FIG. 38 shows MIC data of old (stored for several weeks in a refrigerator) and freshly prepared BDT-4G on MRSA.
Figure 39:
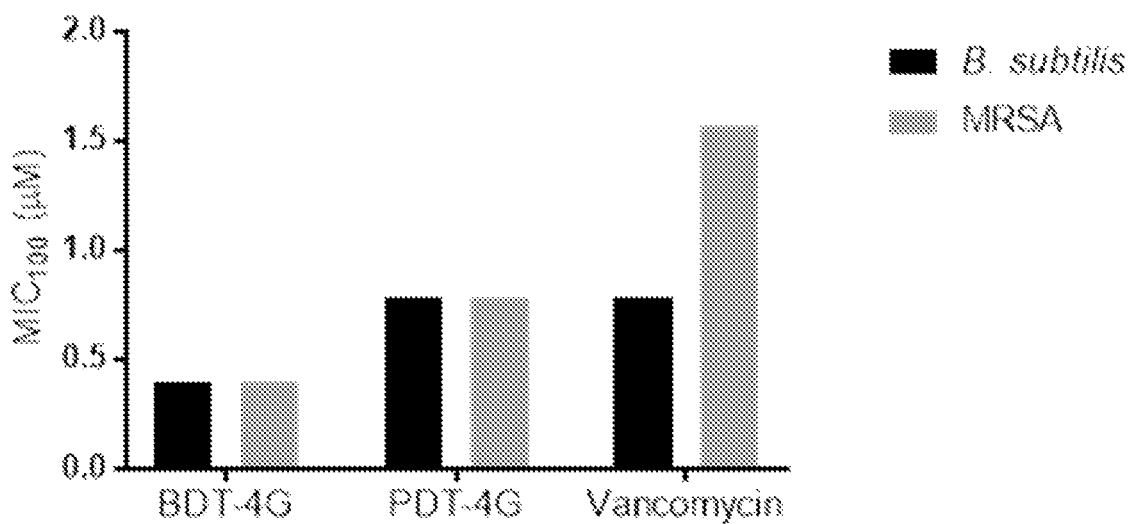
FIG. 39 shows MIC data of BDT-4G and PDT-4G on MRSA and *B. subtilis*.
Figure 40:
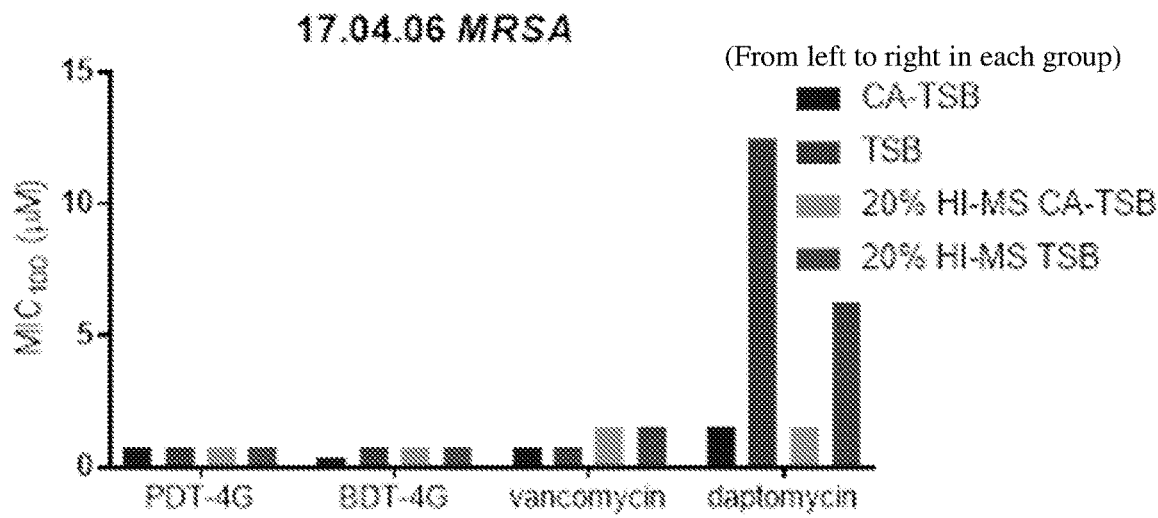
FIG. 40 shows MIC data of PDT-4G, BDT-4G and controls on MRSA in the presence of serum (HI-MS—heat inactivated mouse serum) and cations (CA—calcium).
Figure 41:
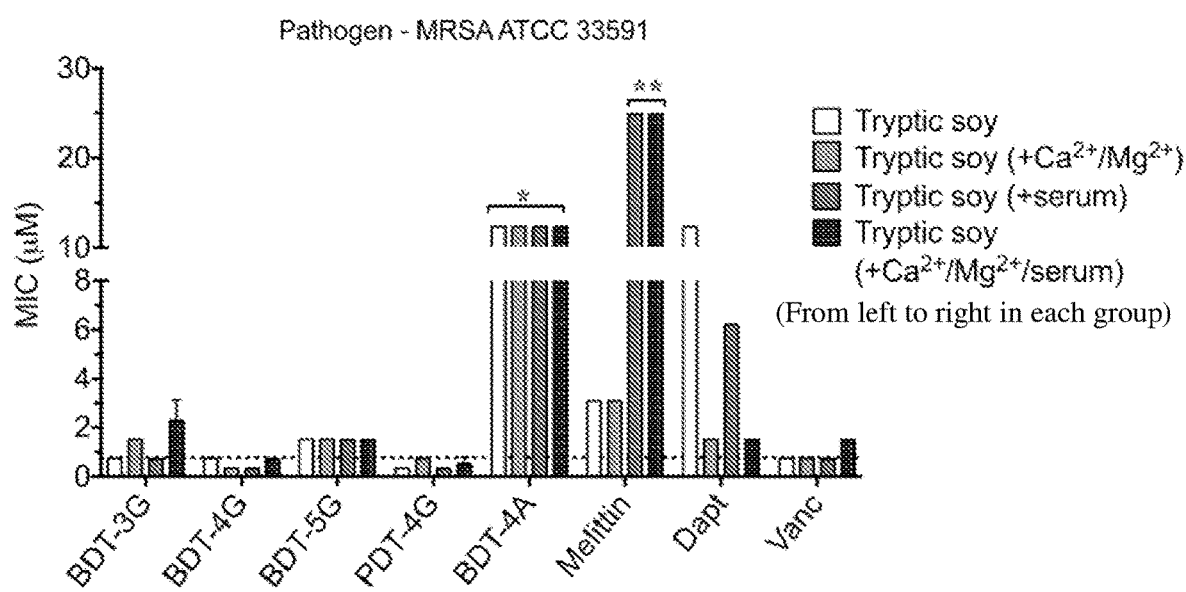
FIG. 41 shows MIC data of oligoTEAs and controls on MRSA 33591 in different media.
Figure 42:
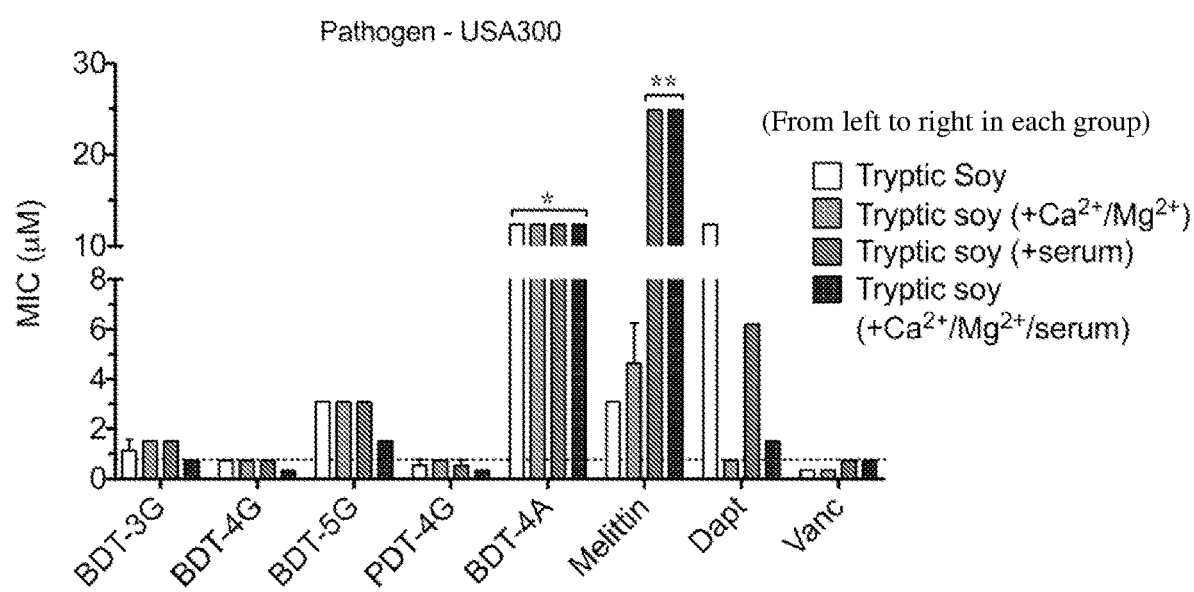
FIG. 42 shows MIC data of oligoTEAs and controls on *Staphylococcus aureus*, strain USA300 in different media.
Figure 43:
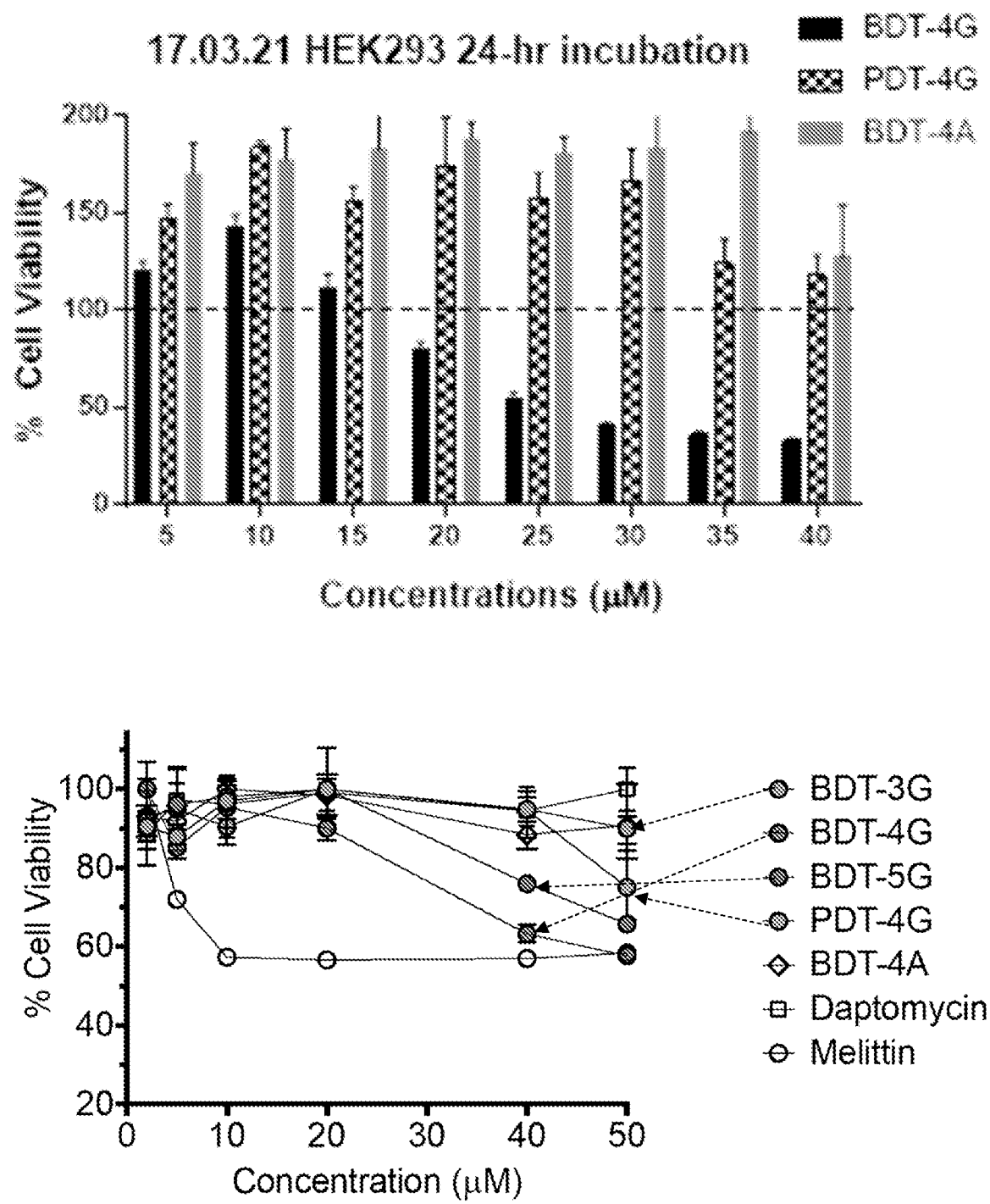
FIG. 43 shows results of an MTS cytotoxicity assay of oligoTEAs and controls to assess toxicity on HEK293 cells. Cells were incubated with compounds for 24 hours (top) or 1 hour (bottom).

FIG. 8 shows the HPLC trace of the cleavage reaction of Ftag-BDT-3G. Two prominent peaks at 11.5 and 12.2 min were collected, dried and checked by LC-MS. The pure product is identified as the peak at 12.2 min, as seen in FIG. 9. The fraction collected at 11.5 is the mono-oxidized product (i.e., M+16) (FIG. 10).

Biological Assays were conducted on the follow compounds:
BDT-3G: synthesized from three 1,4 butanedithiol monomers and three guanidinium-based N-allylacrylamide monomers in a defined sequence
BDT-4G: synthesized from four 1,4 butanedithiol monomers and four guanidinium-based N-allylacrylamide monomers in a defined sequence
BDT-5G: synthesized from five 1,4 butanedithiol monomers and five guanidinium-based N-allylacrylamide monomers in a defined sequence
PDT-4G: synthesized from four 1,3 propanedithiol monomers and four guanidinium-based N-allylacrylamide monomers in a defined sequence
BDT-4Am: synthesized from four 1,4 butanedithiol monomers and four amine-based N-allylacrylamide monomers in a defined sequence Example 2

This example describes uses of compounds (e.g., oligoTEAs) of the present disclosure.

To examine dosing limit and route of administration, a tolerability experiment was performed. This was done by administering PDT-4G via subcutaneous (s.c.) injection between the shoulder blades of three CD-1 mice at a dose of 20 mg/kg. This dose and route was well tolerated and resulted in no adverse signs after 2 and 24 hours.

Figure 44:
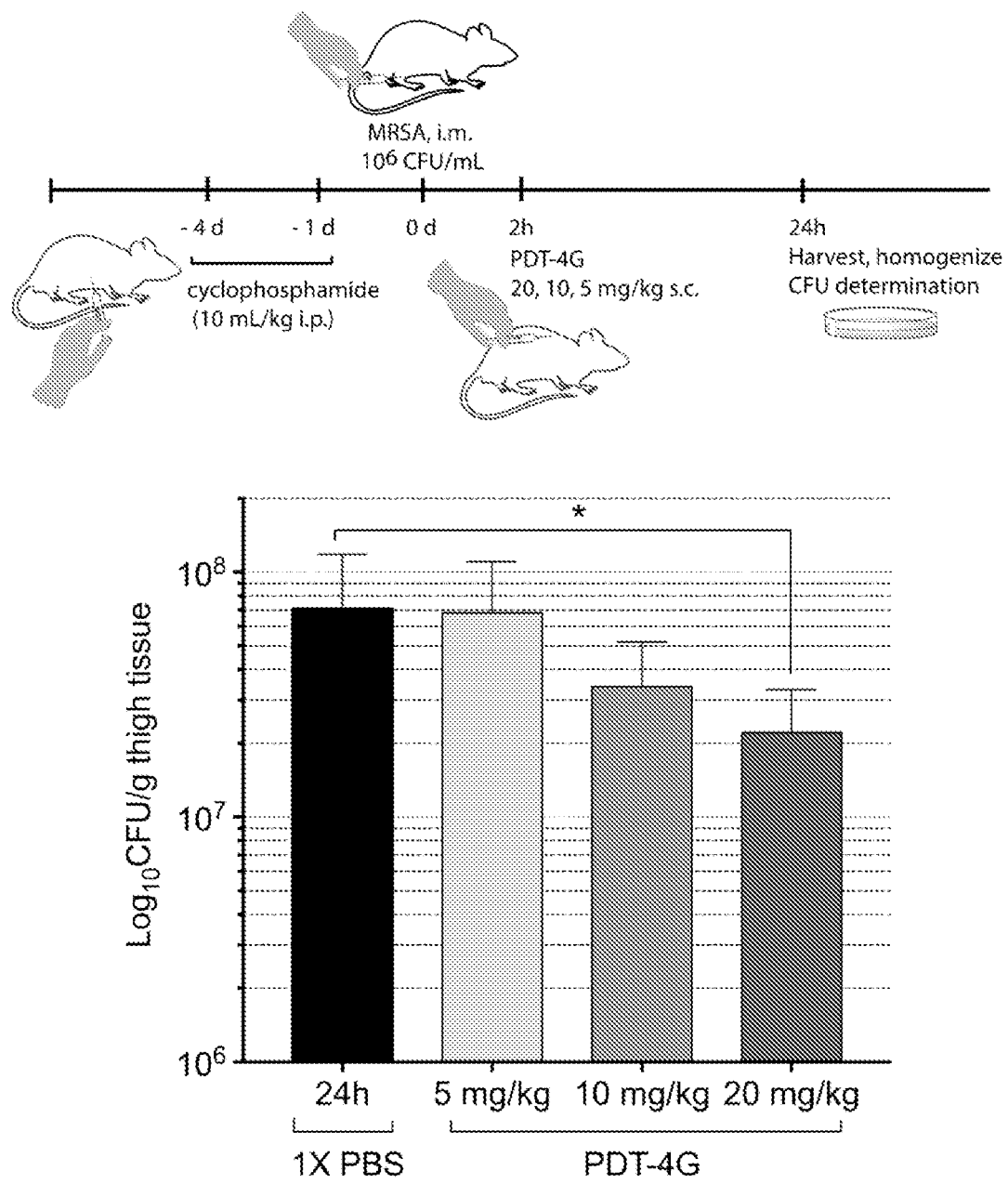
FIG. 44 shows a time course for establishment and treatment of mouse thigh infection model with methicillin-resistant *Staphylococcus aureus* (ATCC 33591). Neutropenic CD-1 mice treated with a single injection of PDT-4G via subcutaneous injection 2 hours post infection (8 mice per group).
Figure 45:
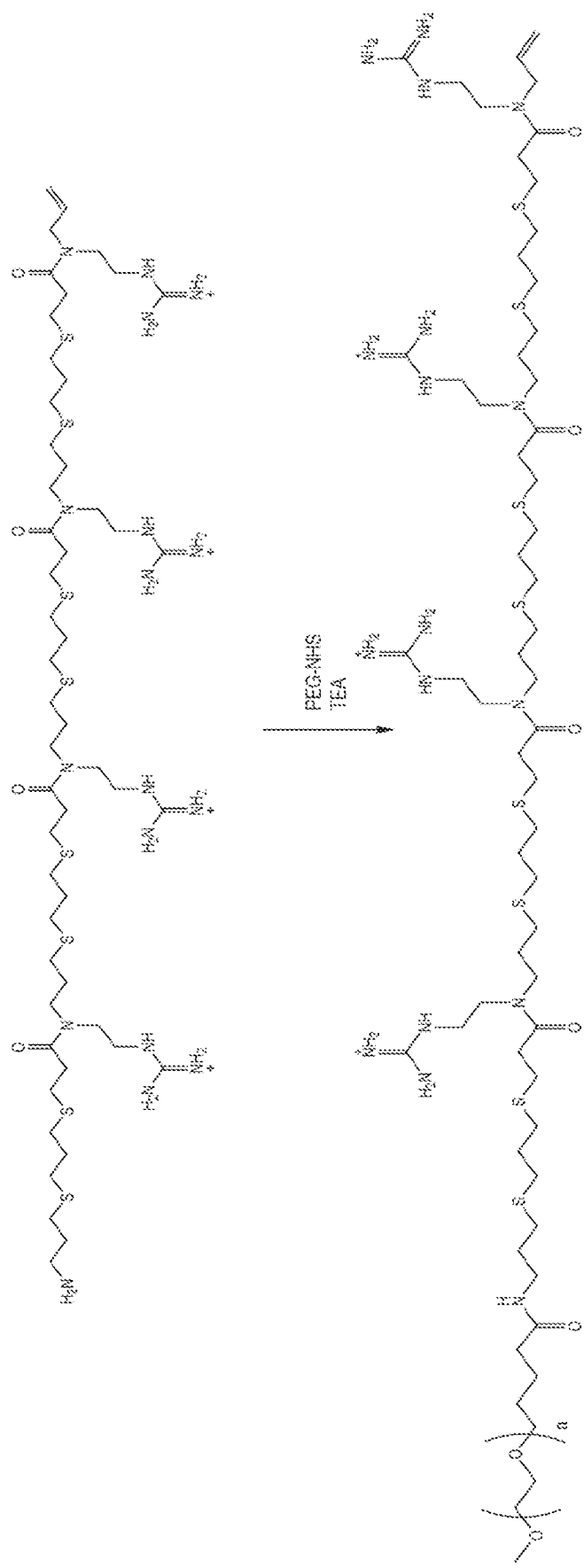
FIG. 45 shows a synthetic scheme of PEG-PDT-4G.
Figure 46:
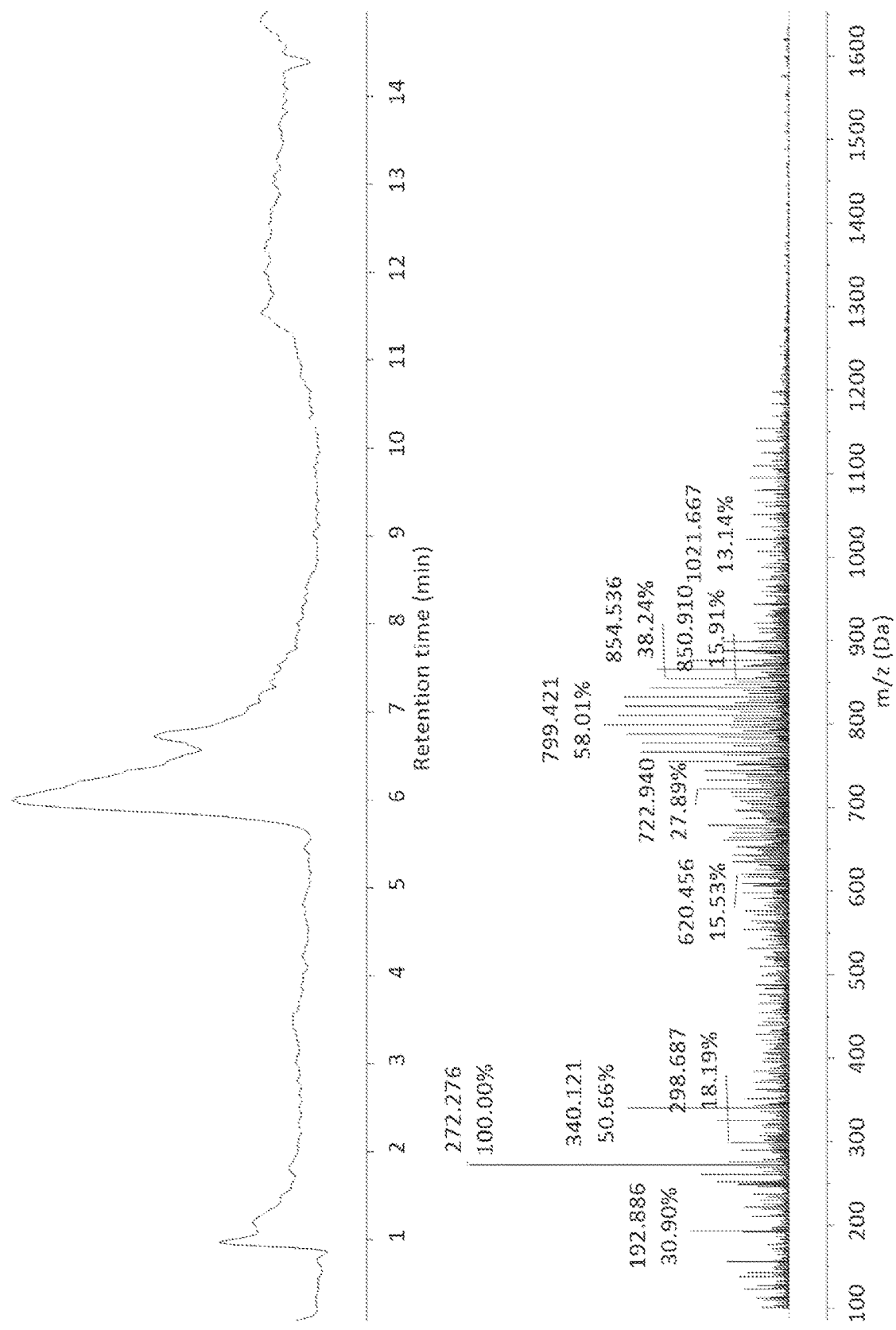
FIG. 46 shows an LC-MS spectrum of PEG2k-PDT4G after HPLC purification. If present, unmodified PDT-4G would have eluted at 4.9 minutes. Peaks around 720-850 Da represent the M+4H mass of PEG2k-PDT4G.
Figure 47:
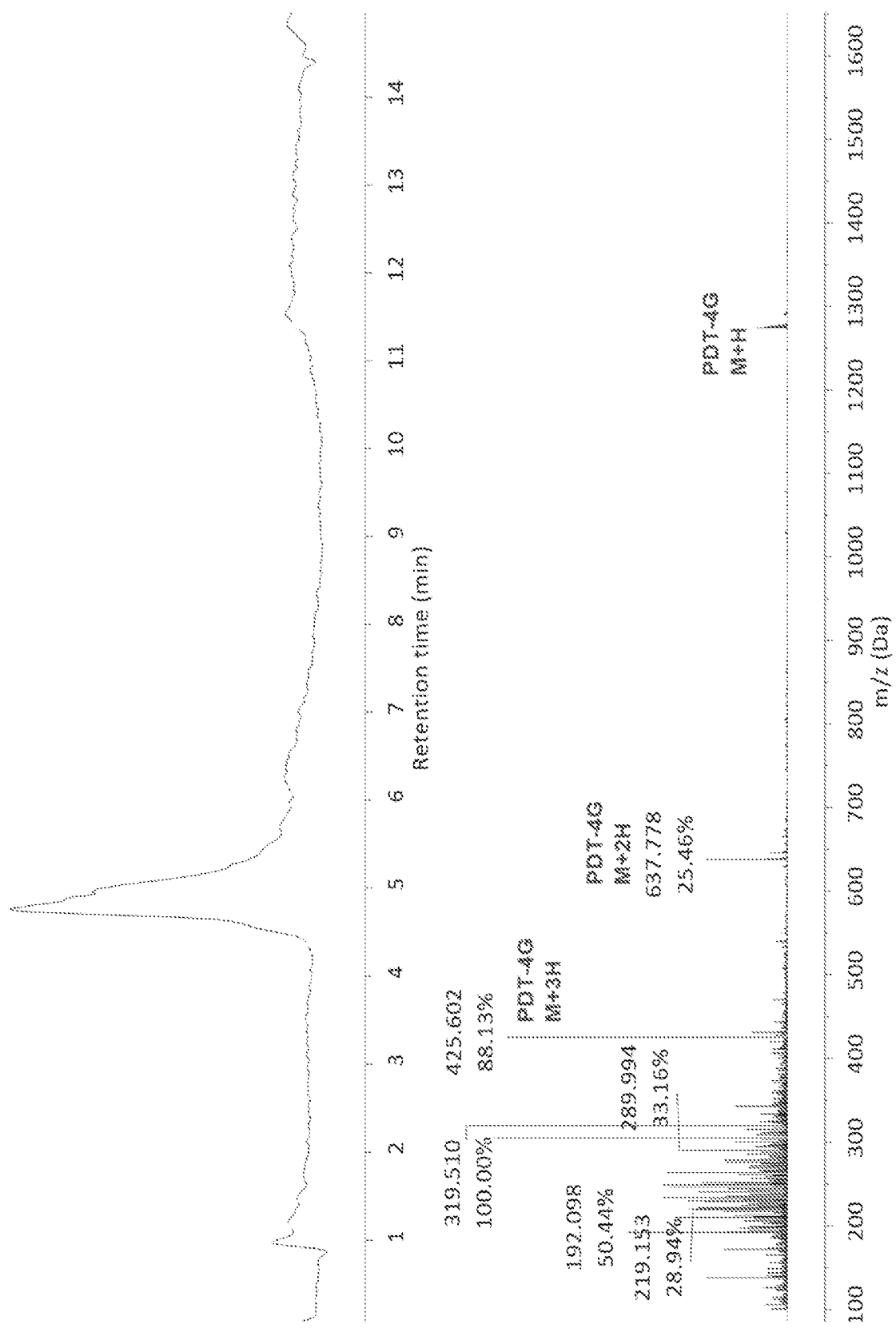
FIG. 47 shows an LC-MS spectrum of PEG5k-PDT4G after purification with a 2 kDa dialysis device. Dominant peak is PDT-4G, which eluted at 4.9 minutes.
Figure 48:
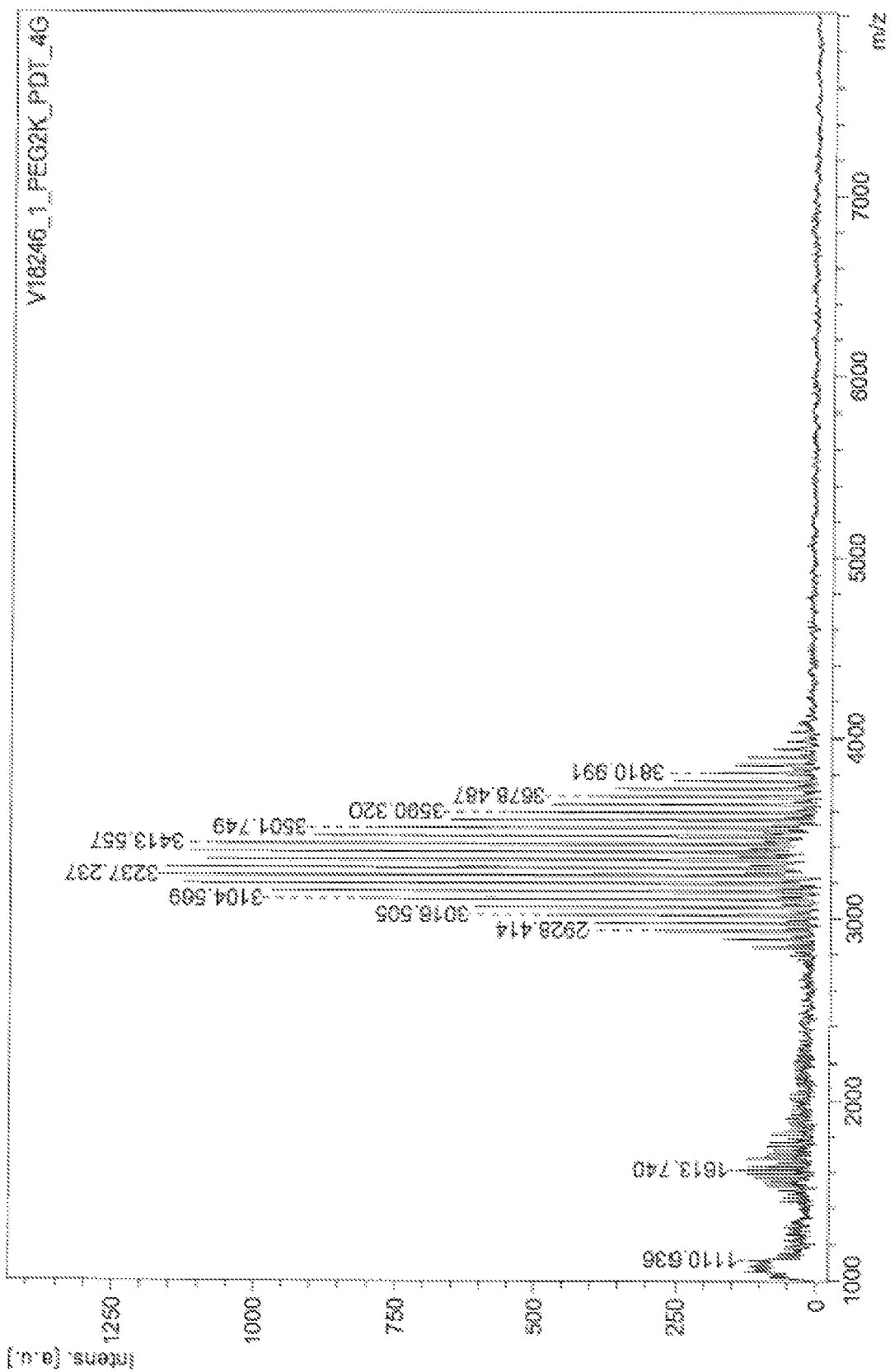
FIG. 48 shows a MALDI-MS spectrum of purified PEG2k-PDT4G showing expected product mass.
Figure 49:
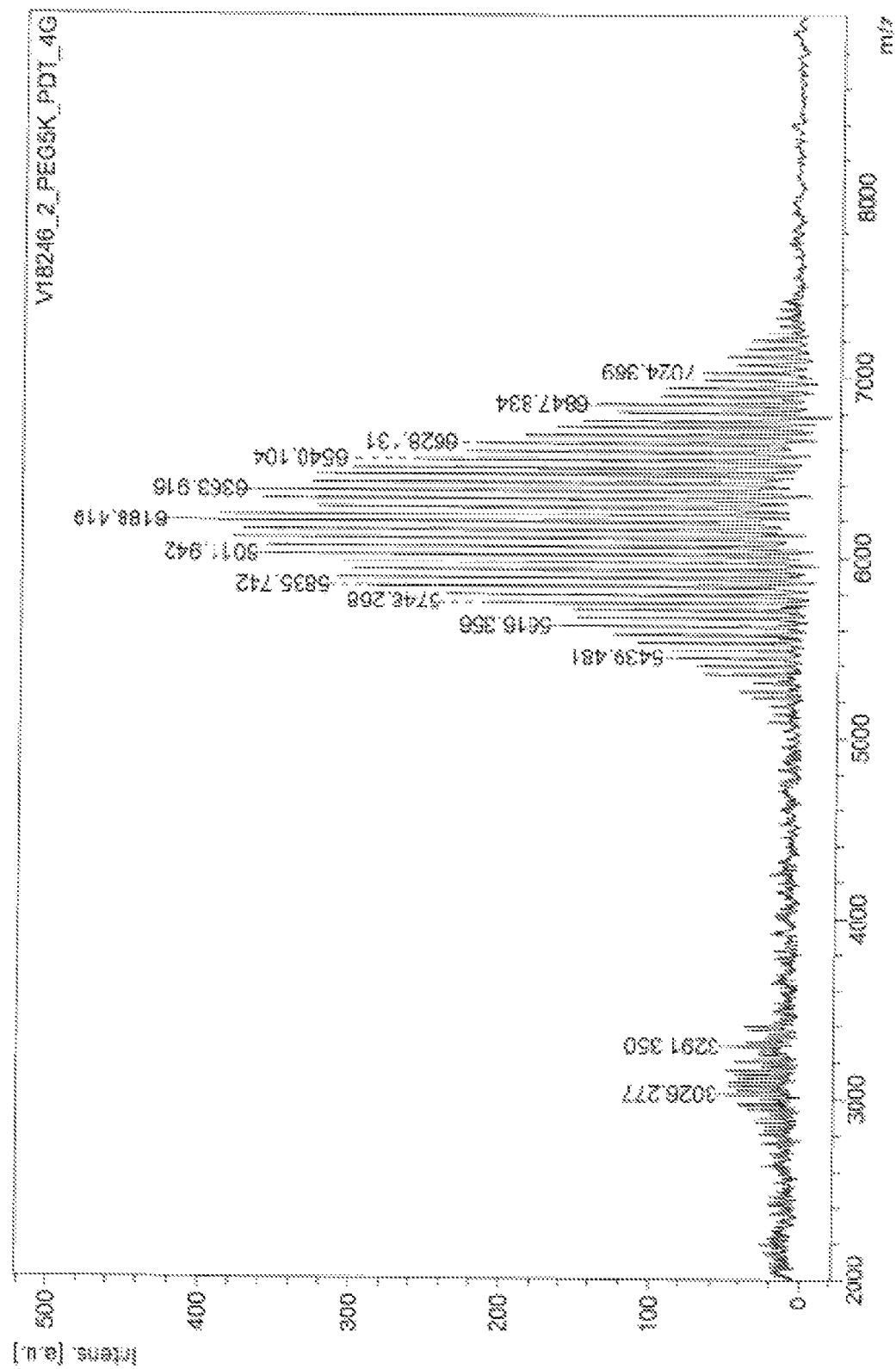
FIG. 49 shows a MALDI-MS spectrum of purified PEG2k-PDT4G showing expected product mass.
Figure 50:
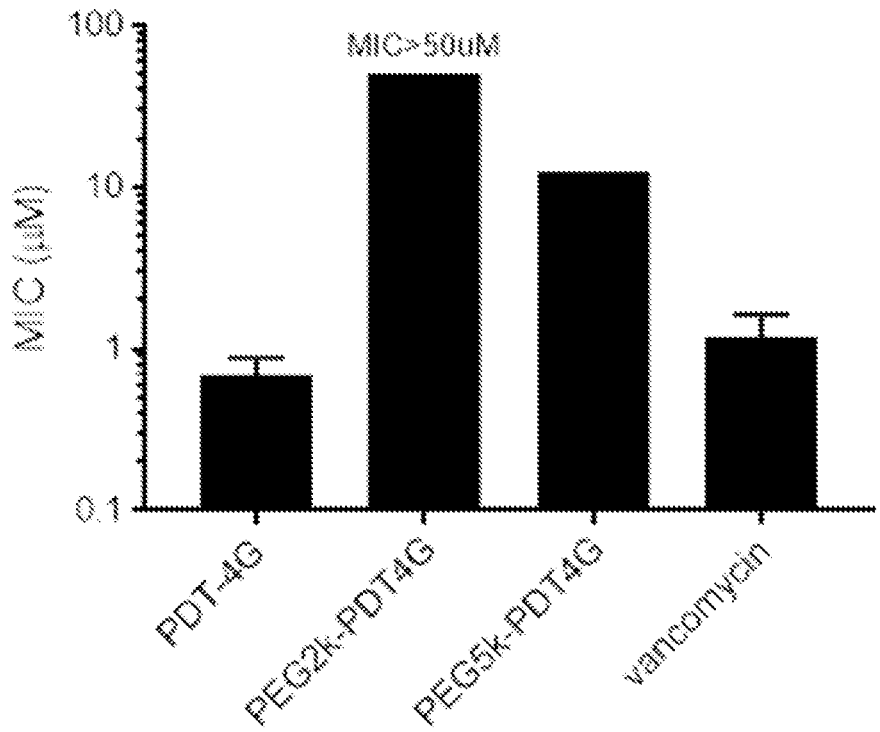
FIG. 50 shows results of a MIC assay of PEGylated and unmodified PDT-4G against MRSA in cation-adjusted tryptic soy broth. Bars represent averages of 2 technical and 2 biological replicates.
Figure 51:
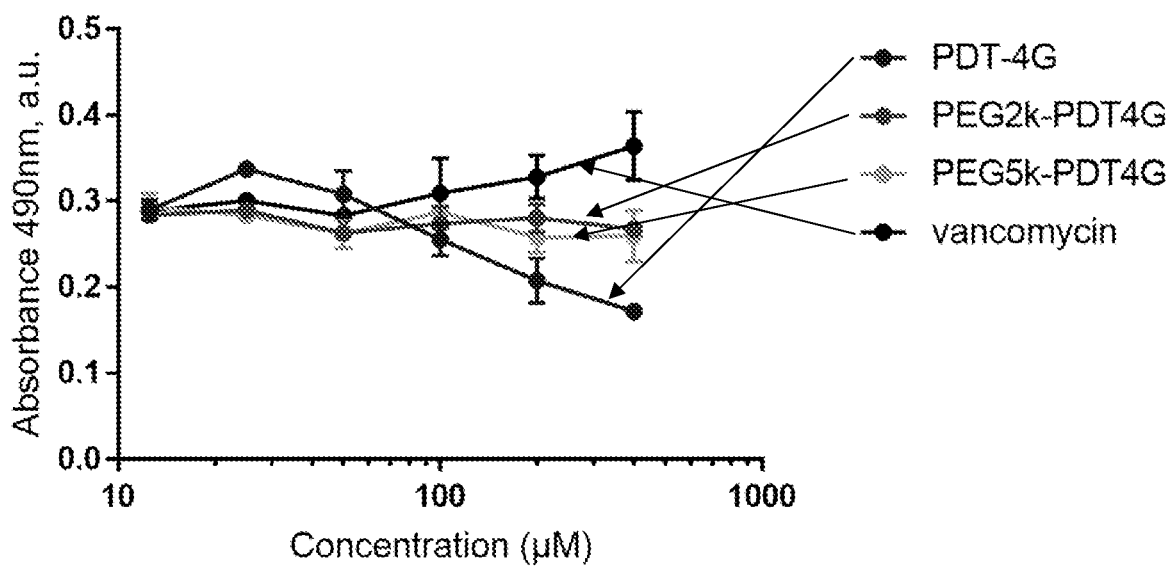
FIG. 51 shows results of an MTS assay of HEK293T cells incubated 1 hour with PEGylated or unmodified PDT-4G.
Figure 52:
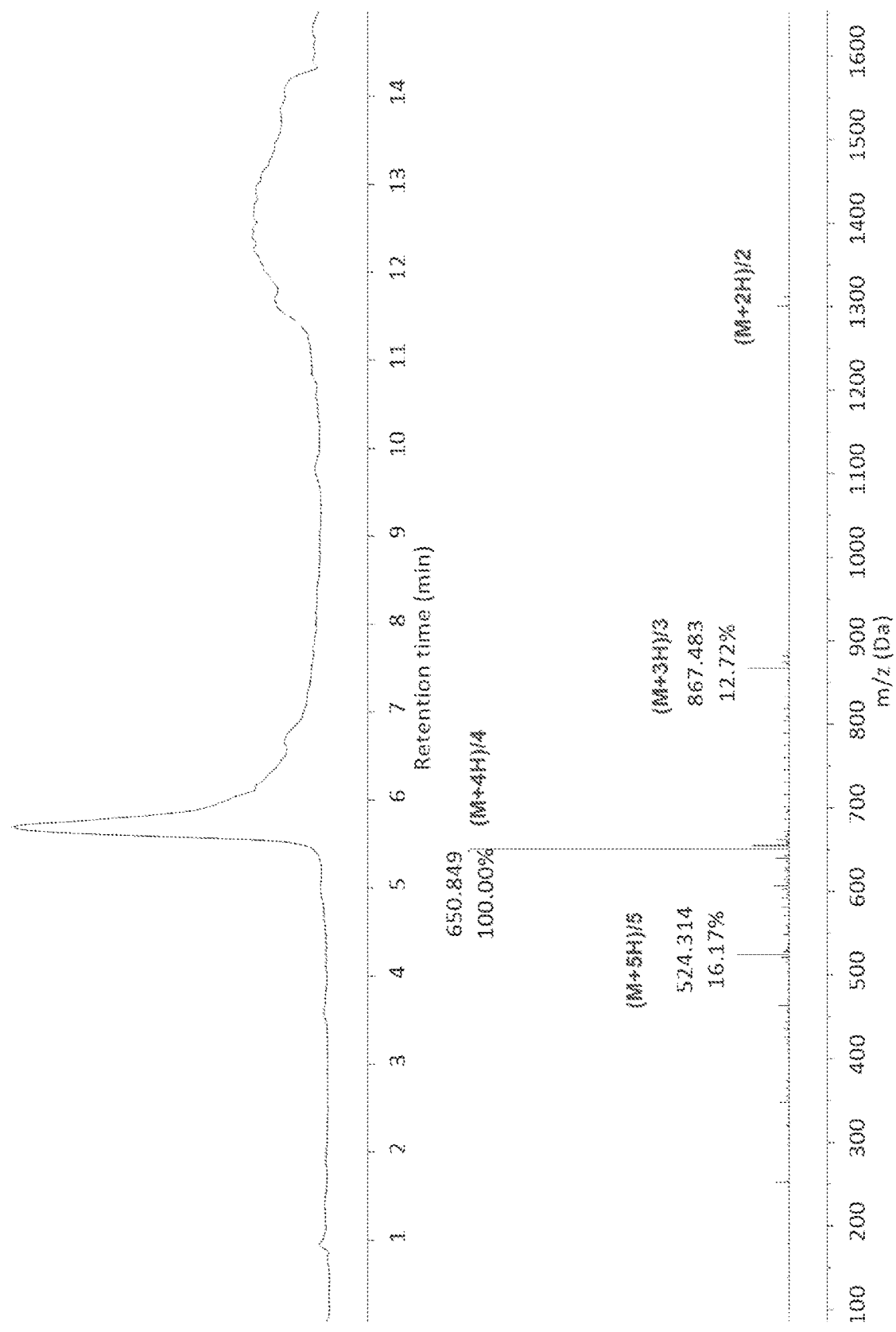
FIG. 52 shows an LCMS of PEG24-LL-PDT-4G.

For efficacy studies, mice were rendered neutropenic by administering cyclophosphamide 4 days and 1 day prior to infection and then inoculated with $10^6$ CFU/mL of MRSA on day 0 (FIG. 44). A single dose of PDT-4G was administered via the s.c. route 2 hours after primary infection at doses ranging from 5-20 mg/kg. At a single dose of 20 mg/kg, PDT-4G led to a 0.5 log CFU reduction of viable MRSA bacterial load (~70% bacterial cell reduction) after 24 hours (FIG. 44). These results illustrate the use of oligoTEAs for the development of viable antibacterial therapeutics that might help address the urgent need for new drug classes to combat antibiotic-resistant bacteria.

PEGylated OligoTEA Prodrugs for Bacterial Targeting. Reducing mammalian-cell toxicity while maintaining antibacterial activity is currently the most significant issue in the design of oligoTEA antibiotics. Developing a controlled method of oligoTEA release whereby the oligoTEA is only activated in the presence of bacteria is anticipated to help reduce systemic toxicity. A possible way to do this is by conjugating the oligoTEA with a bulky non-toxic group such as a large polyethylene glycol (PEG) via a cleavable linker. This linker will be selectively cleaved by bacterial proteases in the presence of bacteria, activating PDT-4G or BDT-4G. In the absence of bacteria, the linker will remain intact and the compound will be inactive and non-toxic. Alternatively, the oligoTEA could be conjugated with a PEG to reduce toxicity, and a peptide sequence that tethers the compound to the bacterial cell membrane. It is believed that either of these approaches will reduce systemic toxicity, and incorporate specificity for select pathogenic bacteria.

Other polymers that can be used in this prodrug strategy in addition to PEGs include hydrophilic polymers such as poly(vinyl alcohol), poly(N-vinylpyrrolidone), poly(2-oxazoline), zwitterionic polymers (polysulfobetaine, polycarboxybetaine, polyphosphorylcholine).

Synthesis of PEG-PDT-4G was performed as follows. 1 equivalent PEG-NHS (polydisperse PEG2k or PEG5k) was added to 2 equivalents PDT-4G and 10 equivalents TEA in dry DMSO for a final concentration of 4.76 mM PDT-4G (with PEG2k and PEG5k). The reaction mixture was incubated at room temperature overnight and purified in one of three ways: The PEG2k reaction was purified by HPLC, the PEG5k reaction was purified using a 2 kDa and 3.5 kDa dialysis cup dialyzed with water overnight. Conjugates were lyophilized, and product molecular weights were verified using MALDI-MS and LCMS.

Antibacterial activity of PEG2k-PDT4G and PEG5k-PDT4G was determined against MRSA (ATCC 33591) using a MIC assay in media supplemented with physiological concentrations of divalent cations (12.5 mg/L $Mg^{2+}$ and 25 mg/L $Ca^{2+}$). PEGylation significantly reduced the activity of PDT-4G, but PEG5k-PDT4G still retained some antibacterial activity with a MIC of 12.5 µM. Interestingly, PEG2k-PDT4G demonstrated no antibacterial activity up to 50 µM.

The mammalian cell toxicity of these compounds was then analyzed using an MTS assay with HEK293T cells on a gelatin-coated 96-wellplate. Neither PEG2k-PDT4G nor PEG5k-PDT4G demonstrated any toxicity against HEK293T cells up to 400 µM over a 1 hour incubation. This is in contrast with PDT-4G, which demonstrated toxicity at 100 µM.

Incorporating a Cleavable Linker in PEGylated Prodrug. A proof of concept PDT-4G was synthesized and conjugated to monodisperse 24-unit PEG (PEG24) and a Leu-Leu (LL) linker. The LL linker has been shown to cleave in the presence of *B. subtilis* proteases, but not *S. aureus*. PEG24-LL-PDT-4G was synthesized, purified using HPLC, and verified by LCMS and $^1$H NMR.

Figure 53:
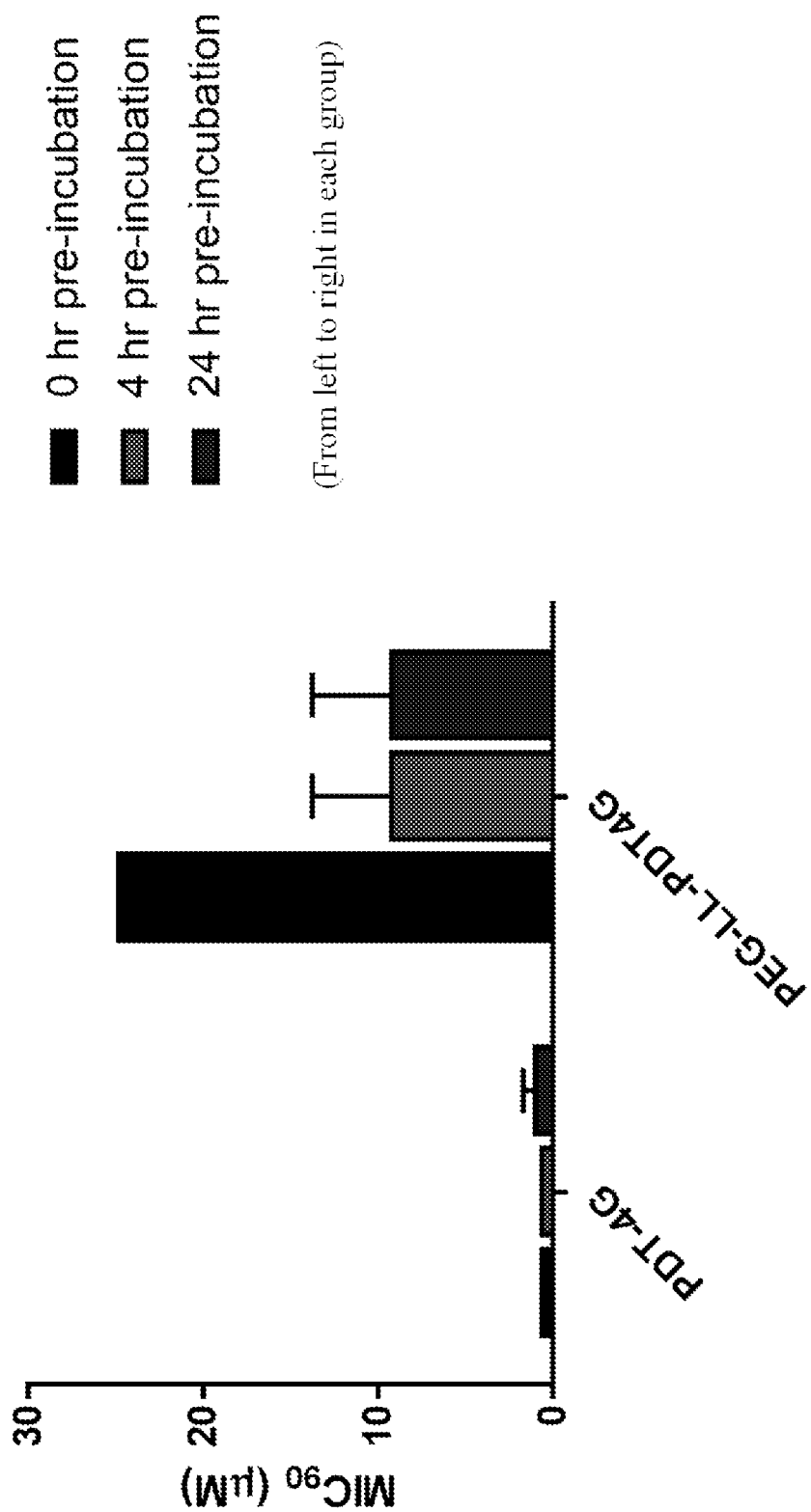
FIG. 53 shows results of an MIC assay of PEG24-Leu-Leu-PDT4G & PDT-4G with *B. subtilis* in cation-adjusted LB media.
Figure 54:
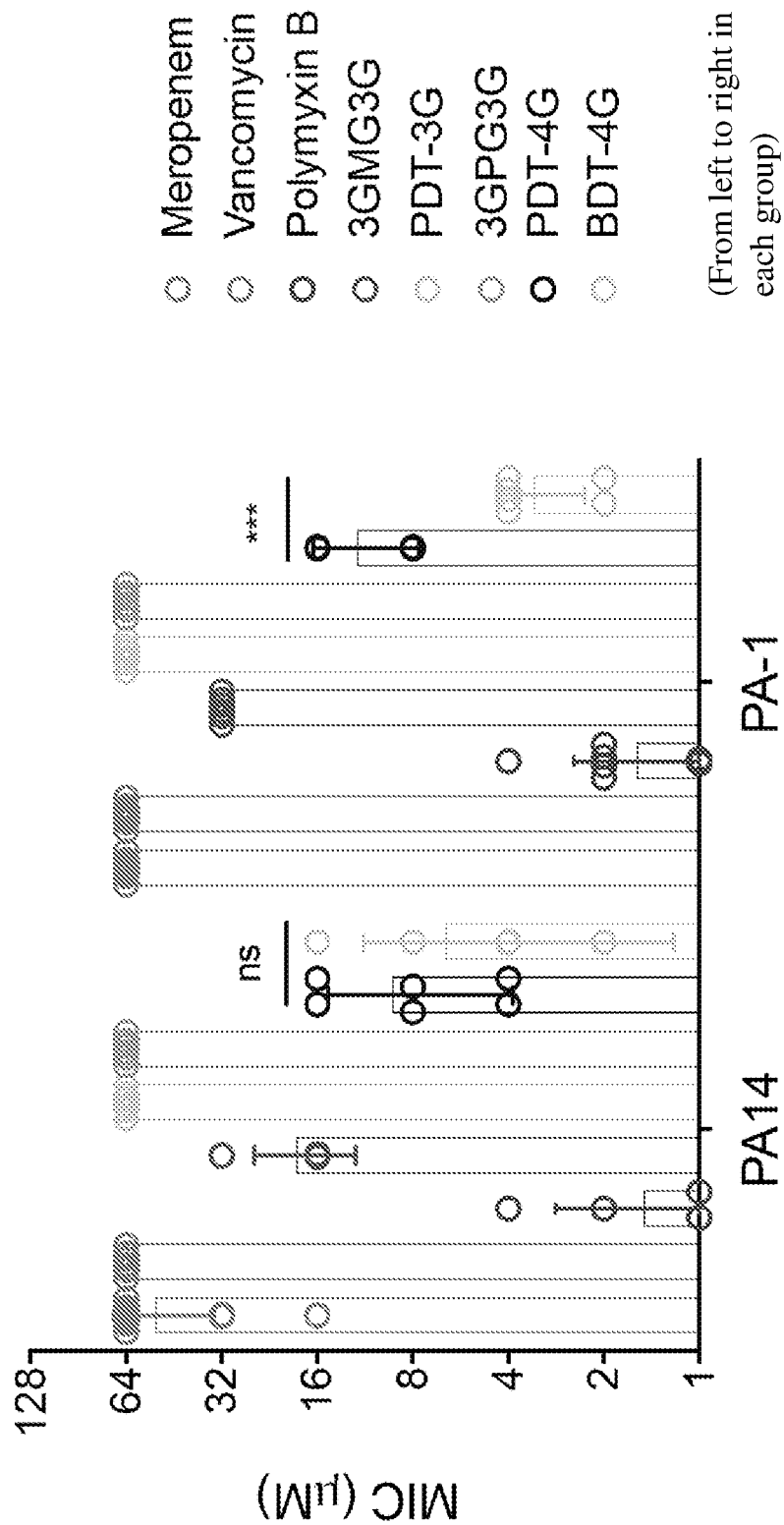
FIG. 54 shows results of an MIC assay of para and meta aromatic dithiol sequences.

The MIC of PEG24-LL-PDT4G against *B. subtilis* was compared with the MIC of unmodified PDT-4G. Both compounds were pre-incubated with *B. subtilis* supernatant for 0, 4, or 24 hours before the MIC assay to test cleavage kinetics (FIG. 53). PEG24-LL-PDT4G is less active than PDT-4G against *B. subtilis*, but results show partial recovery of MIC after preincubation with excess *B. subtilis* supernatant solution. This partial recovery of activity suggests that the LL linker cleaves, but that only partially. These initial results show that this method of oligoTEA prodrug development is promising.

Other Cleavable Linkers to Target Pathogenic Bacteria. Literature sources report a vast number of cleavable groups employed by prodrugs and antibody-drug conjugates. To target MRSA, a 5-residue peptide LPMTG can be used as a linker. Peptides with the general structure LPXTG, where X is any amino acid, are cleaved by the bacterial protease sortase A. Sortase A is a well-documented cell-sorting enzyme produced by *S. aureus* and cleaves LPXTG between the threonine and glycine residues. In particular, LPMTG has been shown cleave at low concentrations in the presence of sortase A.

Other peptide sequences shown to be cleaved by *S. aureus* proteases include Xaa-Leu cleaved by aureolysin or Glu-Arg and Glu-Val cleaved by glutamyl endopeptidase I.

Example 3

This example describes uses of compounds of the present disclosure.

PA-14 is a highly virulent *Pseudomonas aeruginosa* strain (Gram-negative) that is difficult to treat. PA-1 is a meropenem resistant clinical isolate of *Pseudomonas aeruginosa* that was obtained from a patient. Meropenem, vancomycin and polymyxin B are commercial antibiotics that are used as controls. Here, the meta compound (3GMG3G) is 2-4 fold more active than the para substituted compound (3GPG3G). The data shows that PDT-4G and BDT-4G are still the most potent oligoTEAs against these Gram-negative *Pseudomonas* strains.

3GPG3G has the following structure:

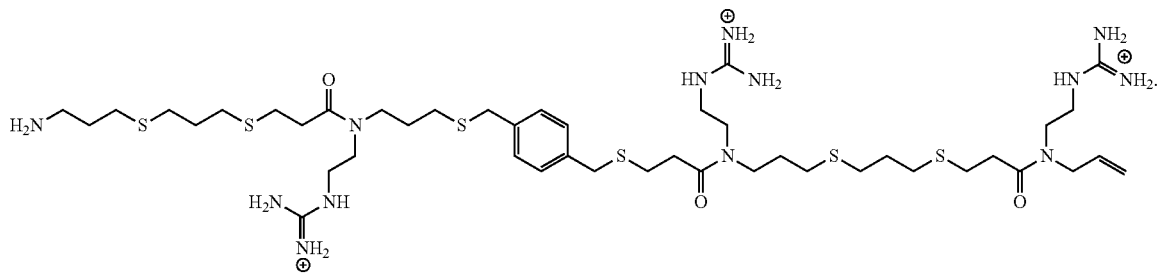

3GMG3G has the following structure:

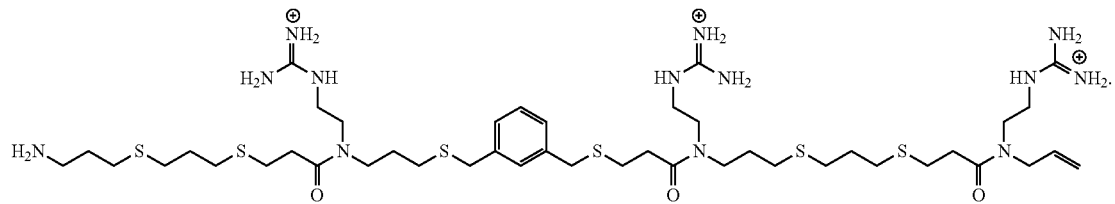

PDT-3G has the following structure:

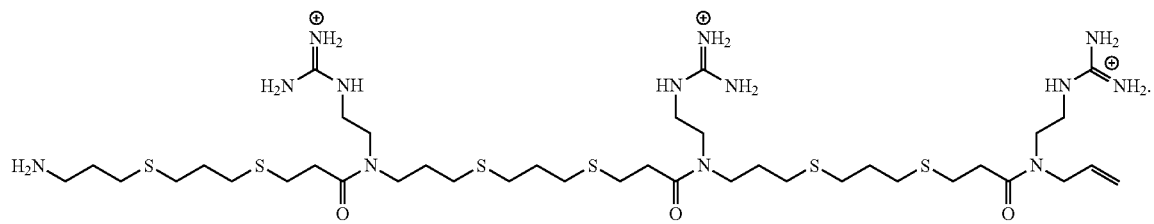

Although the present disclosure has been described with respect to one or more particular embodiments and/or examples, it will be understood that other embodiments and/or examples of the present disclosure may be made without departing from the scope of the present disclosure.

The invention claimed is:

1. A compound having the following structure:

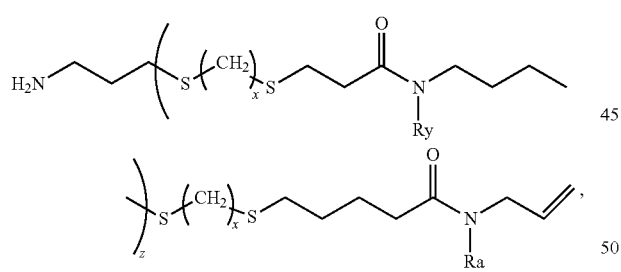

wherein x, independently at each occurrence, is 2 to 10;

Ra and Ry are

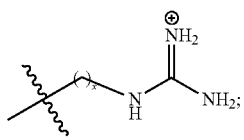 [SMILES: *CNC(N)=[NH2+]]

z is 2 to 7;

or

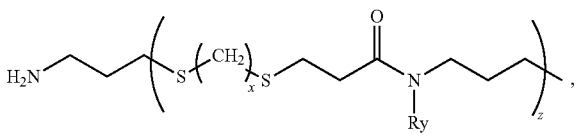

wherein x, independently at each occurrence, is 2 to 10;

Ry is

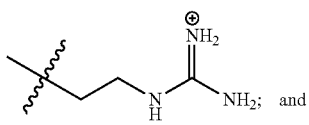 [SMILES: *CCNC(N)=[NH2+] ; "and"]

and z is 2 to 8.

2. The compound of claim 1, wherein the compound has the following structure:

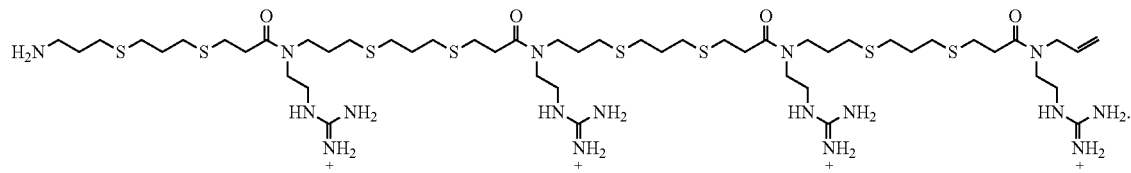 [SMILES: C=CCN(CCNC(=N)N)C(=O)CCSCCCSCCCN(CCNC(=N)N)C(=O)CCSCCCSCCCN(CCNC(=N)N)C(=O)CCSCCCSCCCN(CCNC(=N)N)C(=O)CCSCCCSCCCN]

3. The compound of claim 1, wherein the compound has the following structure:

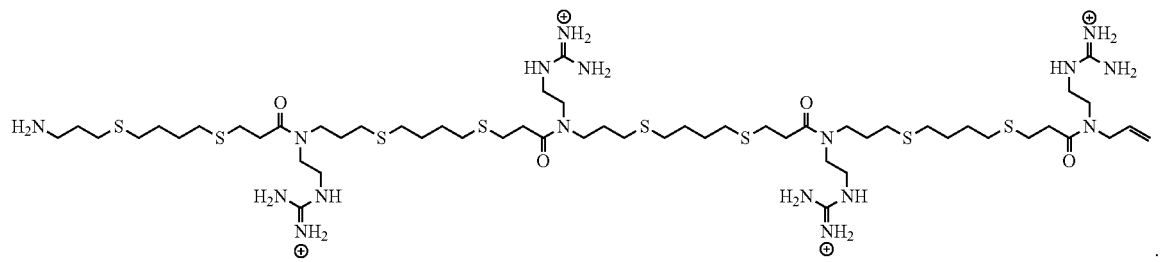 [SMILES: C=CCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN(CCNC(N)=[NH2+])C(=O)CCSCCCCSCCCN]

4. The compound of claim 1, wherein the compound has the following structure:

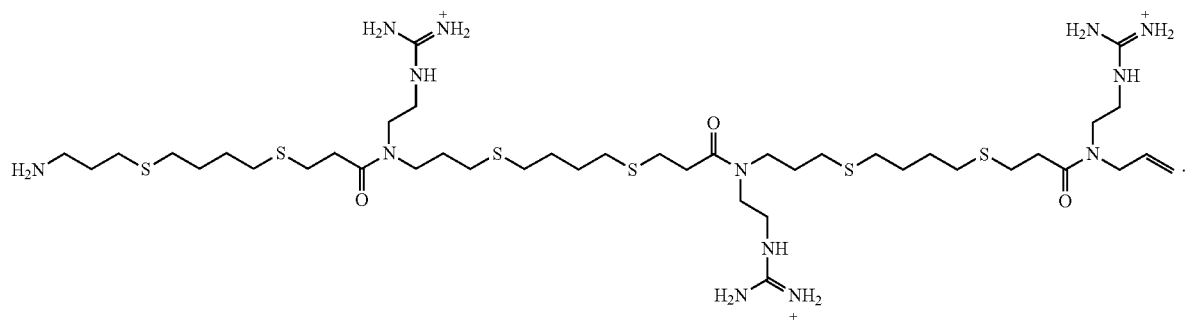 [SMILES: C=CCN(CCNC(=N)N)C(=O)CCSCCCCSCCCN(CCNC(=N)N)C(=O)CCSCCCCSCCCN(CCNC(=N)N)C(=O)CCSCCCCSCCCN]

5. A method of treating a subject in need of treatment with one or more compound(s) of claim 1.

6. The method of claim 5, wherein the subject in need of treatment has a bacterial infection and/or is in need of prophylaxis therefrom.

7. The method of claim 6, wherein the bacterial infection is caused by one or more gram-positive bacteria.

8. The method of claim 6, wherein the bacterial infection is caused by one or more gram-negative bacteria.

9. The method of claim 6, wherein the bacterial infection is caused by one or more gram-positive and one or more gram-negative bacteria.

10. The method of claim 7, wherein the one or more gram-positive bacteria is Methicillin-resistant *Staphylococcus aureus* (MRSA), *Staphylococcus epidermidis, Bacillus subtilis, Streptococcus, Enterococcus, Listeria monocytogenes, Clostridium difficile*, or a combination thereof.

11. The method of claim 8, wherein the one or more gram-negative bacteria is *Pseudomonas aeruginosa, Escherichia coli, Klebsiella pneumonia, Vibrio cholera, Acinetobacter baumannii*, or a combination thereof.

12. The method of claim 9, wherein the one or more gram-positive bacteria is Methicillin-resistant *Staphylococcus aureus* (MRSA), *Staphylococcus epidermidis, Bacillus subtilis, Streptococcus, Enterococcus, Listeria monocytogenes, Clostridium difficile*, or a combination thereof.

13. The method of claim 9, wherein the one or more gram-negative bacteria is *Pseudomonas aeruginosa, Escherichia coli, Klebsiella pneumonia, Vibrio cholera, Acinetobacter baumannii*, or a combination thereof.

14. The method of claim 5, wherein the one or more compound(s) is/are present in a composition comprising a pharmaceutically acceptable carrier.

* * * * *